(12) United States Patent
Plourde et al.

(10) Patent No.: US 11,946,886 B2
(45) Date of Patent: Apr. 2, 2024

(54) FLUID HEATING SYSTEM

(71) Applicant: WTS LLC, St. Paul, MN (US)

(72) Inventors: Brian Plourde, St. Paul, MN (US);
John Abraham, Minneapolis, MN (US); Douglas Plourde, Somerset, WI (US); Richard Pakonen, Birchwood, MN (US); Andy Gikling, St. Paul, MN (US); Noel Naughton, St. Paul, MN (US)

(73) Assignee: WTS LLC, St. Paul, MN (US)

( * ) Notice: Subject to any disclaimer, the term of this patent is extended or adjusted under 35 U.S.C. 154(b) by 0 days.

(21) Appl. No.: 14/954,292

(22) Filed: Nov. 30, 2015

(65) Prior Publication Data

US 2016/0153681 A1    Jun. 2, 2016

Related U.S. Application Data

(60) Provisional application No. 62/259,748, filed on Nov. 25, 2015, provisional application No. 62/085,699, filed on Dec. 1, 2014.

(51) Int. Cl.
*F24S 23/74* (2018.01)
*F24S 30/428* (2018.01)
(Continued)

(52) U.S. Cl.
CPC ............ *G01N 25/00* (2013.01); *F24S 23/74* (2018.05); *F24S 30/428* (2018.05); *F24S 50/40* (2018.05);
(Continued)

(58) Field of Classification Search
CPC .... F24J 2/14; F24J 2/402; F24J 2/5413; F24J 2/42; G01N 25/00; G01N 33/1826;
(Continued)

(56) References Cited

U.S. PATENT DOCUMENTS 3,153,403 A * 10/1964 Dobbs ...................... F01M 1/22
123/198 DB
3,464,402 A *  9/1969 Frank ........................ F24J 2/26
126/661
(Continued)

FOREIGN PATENT DOCUMENTS

CN    102308159 A    1/2012
CN    103370582 A    10/2013
(Continued)

OTHER PUBLICATIONS

Anderson, R, and Collier, K; 1996; "Solar Water Disinfection"; Proceedings of the 1996 Annual Conference ed. Campbell-Howe and B. Wilkins-Crowder, 184-188; Boulder, Colorado; American Solar Energy Society (Year: 1996).*

(Continued)

*Primary Examiner* — Jorge A Pereiro
*Assistant Examiner* — Logan P Jones
(74) *Attorney, Agent, or Firm* — Schwegman Lundberg & Woessner, P.A.

(57) ABSTRACT

A fluid heating system may include a solar collection system configured for focusing sunlight on a focal axis, an elongated flow element arranged and configured for transporting fluid along the solar collection system at the focal axis, and a flow-control assembly comprising thermostatic valves configured to control the flow of the fluid in the elongated flow element such that pathogens present in the fluid are substantially inactivated before the fluid exits the fluid heating system. A method of operating a fluid heating system wherein the fluid heating system comprises a parabolic solar collector and a support structure may also be provided.

13 Claims, 37 Drawing Sheets

(51) Int. Cl.
*F24S 50/40* (2018.01)
*G01N 25/00* (2006.01)
*G01N 33/18* (2006.01)

(52) U.S. Cl.
CPC .......... *G01N 33/1826* (2013.01); *Y02E 10/40* (2013.01); *Y02E 10/47* (2013.01)

(58) Field of Classification Search
CPC ........ Y02E 10/45; Y02E 10/47; Y02W 10/37; C02F 2303/04; C02F 1/14
See application file for complete search history.

(56) References Cited

U.S. PATENT DOCUMENTS

| | | | |
|---|---|---|---|
| 3,915,148 A | 10/1975 | Fletcher et al. | |
| 3,965,972 A * | 6/1976 | Petersen | F24F 5/0046 165/45 |
| 3,991,741 A * | 11/1976 | Northrup, Jr. | F24J 2/08 126/578 |
| 4,024,852 A * | 5/1977 | L'Esperance | F24J 2/10 126/646 |
| 4,032,068 A * | 6/1977 | Luchtenberg | G05D 23/1333 137/599.01 |
| 4,063,543 A * | 12/1977 | Hedger | F24J 2/16 126/579 |
| 4,070,870 A | 1/1978 | Bahel et al. | |
| 4,098,264 A | 7/1978 | Brokaw | |
| 4,269,263 A | 5/1981 | Yukimachi et al. | |
| 4,304,221 A * | 12/1981 | Trihey | F24J 2/10 126/581 |
| 4,735,174 A * | 4/1988 | Crump | F24H 1/205 122/14.3 |
| 4,794,909 A * | 1/1989 | Eiden | F24J 2/542 126/575 |
| 5,505,917 A * | 4/1996 | Collier, Jr. | A61L 2/04 422/307 |
| 5,560,216 A * | 10/1996 | Holmes | E04H 4/1209 62/161 |
| 5,647,531 A * | 7/1997 | Kline | G05D 23/134 236/12.14 |
| 6,410,071 B1 * | 6/2002 | Polster | A23L 3/003 426/521 |
| 6,959,993 B2 | 11/2005 | Gross et al. | |
| 7,339,739 B1 * | 3/2008 | Kinney | F21S 11/00 359/591 |
| 8,849,495 B2 | 9/2014 | Chundrlik et al. | |
| 8,895,836 B2 * | 11/2014 | Amin | G01S 3/7861 136/245 |
| 9,027,545 B2 | 5/2015 | DeVillier | |
| 9,476,611 B1 * | 10/2016 | Shbeeb | F24J 2/38 |
| 10,495,720 B2 | 12/2019 | Plourde et al. | |
| 10,890,645 B2 | 1/2021 | Plourde et al. | |
| 2002/0047814 A1 * | 4/2002 | Yeomans | F24J 2/14 343/912 |
| 2002/0179138 A1 * | 12/2002 | Lawheed | F24J 2/085 136/246 |
| 2006/0201498 A1 * | 9/2006 | Olsson | F24J 2/16 126/605 |
| 2007/0215199 A1 * | 9/2007 | Dold | F24J 2/5424 136/246 |
| 2007/0221362 A1 | 9/2007 | Stewart et al. | |
| 2008/0289334 A1 * | 11/2008 | Orosz | F03G 6/067 60/641.8 |
| 2008/0314322 A1 * | 12/2008 | Stellnert | A01J 7/04 119/14.02 |
| 2009/0032090 A1 | 2/2009 | Kats et al. | |
| 2009/0284018 A1 * | 11/2009 | Ellis | F03D 9/25 290/55 |
| 2009/0320829 A1 * | 12/2009 | Aitken | F24S 50/40 126/587 |
| 2010/0116895 A1 | 5/2010 | Kures | |
| 2010/0169062 A1 * | 7/2010 | Linn | B29C 45/7693 703/2 |
| 2010/0180884 A1 | 7/2010 | Oosting | |
| 2010/0185553 A1 | 7/2010 | Fischer et al. | |
| 2010/0206302 A1 * | 8/2010 | Cheung | F24J 2/14 126/694 |
| 2011/0021133 A1 | 1/2011 | Zwern | |
| 2011/0041784 A1 | 2/2011 | McAlister | |
| 2011/0048502 A1 | 3/2011 | Kikinis et al. | |
| 2011/0073161 A1 * | 3/2011 | Scanlon | F24J 2/38 136/246 |
| 2011/0114079 A1 * | 5/2011 | Heckendorn | F24J 2/38 126/574 |
| 2011/0126824 A1 * | 6/2011 | Conlon | F24S 20/20 126/601 |
| 2011/0308512 A1 * | 12/2011 | Nakasato | F24J 2/14 126/585 |
| 2012/0067338 A1 | 3/2012 | Funcheon | |
| 2012/0085340 A1 | 4/2012 | Hinderling et al. | |
| 2012/0227729 A1 * | 9/2012 | Lundahl | F24S 50/20 126/601 |
| 2012/0234771 A1 * | 9/2012 | Dyson | F24S 20/69 210/748.09 |
| 2012/0325201 A1 | 12/2012 | Deng | |
| 2013/0071527 A1 * | 3/2013 | Pesce | A23L 2/46 426/234 |
| 2013/0098425 A1 | 4/2013 | Amin et al. | |
| 2013/0340846 A1 | 12/2013 | Peel et al. | |
| 2014/0196761 A1 | 7/2014 | Tilley et al. | |
| 2014/0196767 A1 | 7/2014 | Tilley et al. | |
| 2014/0201109 A1 | 7/2014 | Tilley et al. | |
| 2015/0159914 A1 | 6/2015 | Michael | |
| 2015/0357970 A1 | 12/2015 | Mao et al. | |
| 2016/0153920 A1 | 6/2016 | Plourde et al. | |
| 2016/0154082 A1 | 6/2016 | Plourde et al. | |
| 2016/0274602 A1 | 9/2016 | Peel | |
| 2017/0025989 A1 | 1/2017 | Shaw | |
| 2018/0054186 A1 | 2/2018 | Chen et al. | |
| 2018/0142905 A1 | 5/2018 | Plourde et al. | |
| 2019/0107598 A1 | 4/2019 | Plourde et al. | |

FOREIGN PATENT DOCUMENTS

| | | | |
|---|---|---|---|
| CN | 107250687 A | 10/2017 | |
| CN | 107429945 A | 12/2017 | |
| CN | 107429945 B | 7/2020 | |
| CN | 114838511 | 8/2022 | |
| DE | 102008040028 | 7/2010 | |
| DE | 102012021106 | 8/2013 | |
| EP | 2293378 | 3/2011 | |
| EP | 3227618 A1 | 10/2017 | |
| EP | 3227619 A1 | 10/2017 | |
| EP | 3227618 B1 | 3/2021 | |
| GB | 2469321 | 10/2010 | |
| JP | 59081446 A * | 5/1984 | F24J 2/14 |
| WO | 9313396 | 7/1993 | |
| WO | 2008092195 | 8/2008 | |
| WO | 2011035037 | 3/2011 | |
| WO | WO-2013190381 A1 | 12/2013 | |
| WO | 2016089885 | 6/2016 | |
| WO | WO-2016089875 A1 | 6/2016 | |

OTHER PUBLICATIONS

FDA; "Kinetics of Microbial Inactivation for Alternative Food Processing Technologies"; Jun. 2, 2000 (Year: 2000).*
FDA; "Kinetics of Microbial Inactivation for Alternative Food Processing Technologies"; 2000; p. 16 (Year: 2000).*
International Search Report and Written Opinion for related PCT Application No. PCT/US2015/063196 dated May 6, 2016 (19 pages).
International Search Report and Written Opinion for related PCT Application No. PCT/US2015/063208 dated May 6, 2016 (16 pages).
International Search Report and Written Opinion for related PCT Application No. PCT/US2017/062558 dated Mar. 29, 2018 (19 pages).
Invitation to Pay Additional Fees for related PCT/US2018/022826 dated Jun. 27, 2018 (13 pages).

(56) References Cited

OTHER PUBLICATIONS

Stroup et al., "Two-Phas Slug Flow Heat Exchanger for Microbial Thermal Inactivation Research" 18(5) Applied Microbiology 889-892 (1969) (4 pages).
Zenker et al., "Application of Ultrasound-Assisted Tehrmal Processing for Preservation and Quality Retention of Liquid Foods" 66(9) Journal of Food Protection 1642-1649 (2003) (8 pages).
Koutchma et al., "Comparative Experimental evaluation of microbial destruction in continuous-flow microwave and conventional heating systems" 43 Canadian Biosystems Engineering 3.1-3.8 (2001) (8 pages).
International Search Report and Written Opinion for related PCT Application No. PCT/US2018/022826 dated Aug. 20, 2018 (20 pages).
Invitation to Pay Additional Fees for related PCT/US2017/062558 dated Feb. 5, 2018 (14 pages).
International Written Opinion for related PCT Application No. PCT/US2017/062558 dated Oct. 10, 2015 (10 pages).
"U.S. Appl. No. 14/954,383, Final Office Action dated Feb. 25, 2019", 14 pgs.
"U.S. Appl. No. 14/954,383, Non Final Office Action dated Oct. 5, 2018", 14 pgs.
"U.S. Appl. No. 14/954,383, Response filed Jan. 4, 2019 to Non Final Office Action dated Oct. 5, 2018", 10 pgs.
"U.S. Appl. No. 16/196,251, Preliminary Amendment filed Nov. 20, 2018", 5 pgs.
"Chinese Application Serial No. 201580075218.6, Office Action dated Oct. 31, 2018", w/ English translation, 19 pgs.
"Chinese Application Serial No. 201580075218.6, Response filed Mar. 15, 2019 to Office Action dated Oct. 31, 2018", w/ English Claims, 13 pgs.
"Chinese Application Serial No. 201580075224.1, Office Action dated Oct. 31, 2018", w/ English translation, 20 pgs.
"Chinese Application Serial No. 201580075224.1, Response filed Mar. 15, 2019 to Office Action dated Oct. 31, 2018", w/ English Claims, 14 pgs.
"European Application Serial No. 15808528.2, Communication Pursuant to Article 94(3) EPC dated Feb. 28, 2019", 5 pgs.
"European Application Serial No. 15808528.2, Response filed Feb. 14, 2018 to Communication pursuant to Rules 161(2) and 162 EPC dated Aug. 4, 2017", 10 pgs.
"European Application Serial No. 15816974.8, Communication Pursuant to Article 94(3) EPC dated Aug. 22, 2018", 5 pgs.
"European Application Serial No. 15816974.8, Response filed Jan. 10, 2018 to Communication pursuant to Rules 161(2) and 162 EPC dated Jul. 7, 2017", 11 pgs.
"International Application Serial No. PCT/US2015/063196, International Preliminary Report on Patentability dated Jun. 15, 2017", 13 pgs.
"International Application Serial No. PCT/US2015/063208, International Preliminary Report on Patentability dated Jun. 15, 2017", 10 pgs.
"European Application Serial No. 15808528.2, Response Filed Jul. 10, 2019 to Communication Pursuant to Article 94(3) EPC dated Feb. 28, 2019", 9 pgs.
"Chinese Application Serial No. 201580075218.6, Office Action dated Jun. 25, 2019", w English translation, 9 pgs.
"Application Serial No. 14 954,383, Response filed Jul. 25, 2019 to Final Office Action dated Feb. 25, 2019", 12 pgs.
"Chinese Application Serial No. 201580075224.1, Office Action dated Jun. 25, 2019", W English Translation, 6 pgs.
U.S. Appl. No. 14/954,091 U.S. Pat. No. 10,168,412, filed Nov. 30, 2015, Dual Axis Tracking Device.
U.S. Appl. No. 16/196,251, filed Nov. 20, 2018, Dual Axis Tracking Device.
U.S. Appl. No. 14/954,383, filed Nov. 30, 2015, Method of Calculating Pathogen Inactivation For a Fluid Heating System.
"U.S. Appl. No. 14/954,383, Non Final Office Action dated Oct. 1, 2019", 11 pgs.

"U.S. Appl. No. 14/954,383, Response filed Feb. 3, 2020 to Non Final Office Action dated Oct. 1, 2019", 9 pgs.
"Chinese Application Serial No. 201580075218.6, Office Action dated Dec. 2, 2019", w/ English Translation, 15 pgs.
"Chinese Application Serial No. 201580075218.6, Response Filed Sep. 10, 2019 to Office Action dated Jun. 25, 2019", w/English Claims, 15 pgs.
"Chinese Application Serial No. 201580075224.1, Office Action dated Dec. 2, 2019", w/ English Translation, 7 pgs.
"Chinese Application Serial No. 201580075224.1, Response Filed Sep. 10, 2019 to Office Action dated Jun. 25, 2019", w/English Claims, 14 pgs.
"European Application Serial No. 15816974.8, Communication Pursuant to Article 94(3) EPC dated Oct. 8, 2019", 8 pgs.
"Indian Application Serial No. 201737018679, First Examination Report dated Dec. 10, 2019", w/ English Translation, 11 pgs.
"U.S. Appl. No. 14/954,383, Examiner Interview Summary dated Jun. 23, 2020", 3 pgs.
"U.S. Appl. No. 14/954,383, Final Office Action dated Mar. 9, 2020", 13 pgs.
"U.S. Appl. No. 16/196,251, Notice of Allowance dated May 20, 2020", 12 pgs.
"Chinese Application Serial No. 201580075218.6, Decision of Rejection dated Mar. 23, 2020", w/ English Translation, 20 pgs.
"Chinese Application Serial No. 201580075218.6, Response filed Feb. 17, 2020 to Office Action dated Dec. 2, 2019", w/ English Claims, 14 pgs.
"Chinese Application Serial No. 201580075224.1, Response filed Feb. 17, 2020 to Office Action dated Dec. 2, 2019", w/ English Claims, 12 pgs.
"European Application Serial No. 15816974.8, Response filed Feb. 11, 2020 to Communication Pursuant to Article 94(3) EPC dated Oct. 8, 2019", 9 pgs.
"Indian Application Serial No. 201737018676, Response filed Jun. 10, 2020 to First Examination Report dated Dec. 10, 2019", w/ English Claims, 117 pgs.
"Indian Application Serial No. 201737018679, Response filed Jun. 10, 2020 to First Examination Report dated Dec. 10, 2019", 120 pgs.
"U.S. Appl. No. 14/954,383, Non Final Office Action dated Aug. 17, 2020", 13 pgs.
"U.S. Appl. No. 14/954,383, Response filed Jul. 7, 2020 to Final Office Action dated Mar. 9, 2020", 8 pgs.
"U.S. Appl. No. 16/196,251, Notice of Allowance dated Sep. 17, 2020", 7 pgs.
"U.S. Appl. No. 16/196,251, Supplemental Notice of Allowability dated Oct. 9, 2020", 4 pgs.
"Chinese Application Serial No. 201580075218.6, Response filed Jul. 7, 2020 to Decision of Rejection dated Mar. 23, 2020", w/ English Claims, 15 pgs.
"U.S. Appl. No. 14/954,383, Final Office Action dated Jan. 22, 2021", 15 pgs.
"U.S. Appl. No. 14/954,383, Notice of Allowance dated Apr. 5, 2021", 10 pgs.
"U.S. Appl. No. 14/954,383, Response filed Mar. 18, 2021 to Final Office Action dated Jan. 22, 2021", 10 pgs.
"U.S. Appl. No. 14/954,383, Response filed Nov. 17, 2020 to Non Final Office Action dated Aug. 17, 2020", 8 pgs.
"Chinese Application Serial No. 201580075218.6, Notice of Reexamination dated Jul. 22, 2021", W/English Translation, 16 pgs.
"European Application Serial No. 15816974.8, Communication Pursuant to Article 94(3) EPC dated Apr. 6, 2021", 5 pgs.
"European Application Serial No. 15816974.8, Response filed Aug. 12, 2021 to Communication Pursuant to Article 94(3) EPC dated Apr. 6, 2021", 8 pgs.
"Application Serial No. 14 954,383, Notice of Allowance dated Oct. 15, 2021", 9 pgs.
"Chinese Application Serial No. 201580075218.6, Notice of Reexamination dated Oct. 27, 2021", with English translation, 4 pages.
"Chinese Application Serial No. 201580075218.6, Response filed Dec. 13, 2021 to Notice of Reexamination dated Oct. 27, 2021", with English claims, 14 pages.

(56) References Cited

OTHER PUBLICATIONS

"European Application Serial No. 15816974.8, Communication Pursuant to Article 94(3) EPC dated Nov. 2, 2022", 6 pgs.

* cited by examiner

| PARAMETER | VALUE |
|---|---|
| FLUID DENSITY | 1000 kg/m$^3$ |
| FLUID HEAT CAPACITY | 4200 J/kg-°C |
| PIPE DENSITY | 8900 kg/m$^3$ |
| PIPE HEAT CAPACITY | 385 J/kg-°C |
| PIPE OD/ID | 0.02/0.01 m |
| PIPE LENGTH | 4 m |
| $K_{inlet}$ | 1 |
| $K_{valve}$ | 10 |
| VALVE OPERATING TEMPERATURE | 70 °C |
| TANK WATER TEMPERATURE | 25 °C |
| MIRROR DIAMETER | 1 m |
| SOLAR LOSS FACTOR | 0.5 |
| AMBIENT TEMPERATURE | 25 °C |
| PIPE EMISSIVITY | 0.9 |
| HEAT EXCHANGER EFFECTIVENESS | 0.5 |

FLUID HEATING SYSTEM

CROSS-REFERENCE TO RELATED APPLICATIONS

The present application claims priority to U.S. Provisional Patent Application No. 62/085,699 filed on Dec. 1, 2014, entitled Mathematical Model for the Inactivation of Biological Contaminates Using Solar Heating and U.S. Provisional Patent Application No. 62/259,748 filed on Nov. 25, 2015, entitled Fluid Heating System, the contents of which are hereby incorporated by reference herein in their entireties. In addition, the present application is related to U.S. Non-Provisional patent application Ser. No. 14/954,091 filed on Nov. 30, 2015, entitled Dual Axis Tracking Device, U.S. Non-Provisional Patent Application No. 14/954,318 filed on Nov. 30, 2015, entitled Control Valve Assembly for a Fluid Heating System, and U.S. Non-Provisional Application No. 14/954,383 filed on Nov. 30, 2015 entitled Method of Calculating Pathogen Inactivation for a Fluid Heating System, the contents of each of which are hereby incorporated by reference herein in their entireties.

FIELD OF THE INVENTION

The present application relates to a fluid heating system and associated mechanisms and devices. More particularly, the present application relates to a solar fluid heating system for use in heating, thermally pasteurizing, or otherwise treating water or other fluid. Still more particularly, the present application relates to a passive or substantially passive solar tracking and fluid heating system for heating, thermally pasteurizing, or otherwise treating water or other fluid. Several of the associated mechanisms and devices have applicability outside the context of fluid heating or solar fluid heating. Accordingly, while several systems and devices are described in the context of solar collection and fluid heating, it is to be understood that applicability in other situations and for other purposes applies.

BACKGROUND

Thermal pasteurization may refer to raising water or other fluid temperature to make the water or fluid safe. In the case water, the water may be safe to drink, for example, after it is pasteurized. The pasteurization may not result in all pathogens being killed or inactivated, but may reduce the pathogen level to a level suitable and/or safe for human consumption. Accordingly, pasteurization may not be the same as sterilization. Moreover, pasteurization may not remove particulates or turbidity from water. However, in comparison to other pasteurization processes such as slow/rapid sand filters, chemical treatments, and use of ultraviolet light, thermal pasteurization is not negatively impacted by turbidity. This feature makes thermal pasteurization particularly advantageous for water or fluid that may be less than clear.

Thermal pasteurization has been thought of as a batch or flow-through process. In a batch process, water or fluid containers may be heated by burning fuels or by exposure to sunlight. For a flow-through process, the water or fluid may be heated while it passes through a pipe or duct and emerges as pasteurized. Batch processes may be less expensive to manufacture, but they may be more expensive to operate due to the need to bring the system up to a suitable temperature each time a new batch is started.

Inactivation and rates of inactivation of various pathogens vary based on the type of pathogen and, while it is common to bring water to a boil to assure inactivation of pathogens, most pathogens may be inactivated at temperatures below boiling. However, it remains that inactivation rates increase rapidly as temperatures increase.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

In one or more embodiments, a fluid heating system may include a solar collection system configured for focusing sunlight on a focal axis, an elongated flow element arranged and configured for transporting fluid along the solar collection system at the focal axis, and a flow-control assembly comprising thermostatic valves configured to control the flow of the fluid in the elongated flow element such that pathogens present in the fluid are substantially inactivated before the fluid exits the fluid heating system. The system may also include a preheat heat exchanger configured to utilize fluid exiting the fluid heating system to heat fluid entering the fluid heating system. The preheat heat exchanger may include a first tortuous pathway and a second tortuous pathway, the first and second tortuous pathways being in substantial alignment with one another such that heat may be exchanged between the pathways. The system may also include a water collecting reservoir configured to collect water to be pasteurized. The solar collection system may include a reflective element including a solar film laminated to a flexible substrate. The solar collection system may also include a frame defining a parabolic shape and the reflective element may be held in shape by the frame.

In one or more embodiments, the system may include a housing arranged about a non-exposed side of the elongated flow element. The housing may include an insulating material. In one or more embodiments, the hood may be configured to resist convective flow of air by the elongated flow element. The system may also include a return line, the return line being positioned in the housing. The return line may be insulated from the elongated flow element. The elongated flow element may be secured to the control valve assembly at a first end and to the preheat heat exchanger at a second end and the elongated flow element may be secured at each end with an expansion joint.

The system may also include a treated fluid collection tank. The system may also include a tracking system configured for directing the solar collection system at the sun. In one or more embodiments, the collection tank may include a fluid level sensor in communication with the tracking system and the tracking system may be configured to direct the solar collection system away from the sun when the fluid level sensor indicates that the treated fluid collection tank is full.

The tracking system may include a dual axis tracking system configured for directing the solar collection system at the sun. The dual axis tracking system may be configured to pivot the solar collection system about two axes. The system may also include a support structure including an upright support member, an arm portion extending laterally from the upright support member, and a spine portion offset from the arm portion and extending substantially parallel to the arm portion. The arm portion may be pivotable about a seasonal axis extending perpendicular to the upright support member and perpendicular to the arm portion. The spine portion may be pivotable about a day axis extending longitudinally along the spine portion. The system may also include two actuation assemblies for pivoting the solar collection system about the seasonal and day axes.

In one or more embodiments, a method of operating a fluid heating system wherein the fluid heating system comprises a parabolic solar collector and a support structure may be provided. The method may include arranging the fluid heating system along a North/South axis on the surface of the earth and directing the parabolic solar collector at a sun. Directing the parabolic solar collector may include activating a control module comprising a GPS communication device, wherein the control module receives GPS data from satellites including coordinate data defining the location of the fluid heating system on the surface of a planet, date data, and time data and automatically directs the solar collector at a sun. Automatically directing the solar collector at the sun may include pivoting the solar collector about a day axis and a seasonal axis. The seasonal axis may be a substantially horizontal axis relative to the surface of the planet. The day axis may be an axis arranged substantially parallel to a longitudinal length of the solar collector.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure, in some embodiments, relates to a fluid heating system for heating and/or thermal pasteurization of water. In particular, the fluid heating system may include an elongate parabolic mirror for focusing sunlight on a focal point or focal axis. A fluid heating tube may be arranged along the mirror and along the focal axis of the minor. Water may be controllably passed through the heating tube at a calibrated rate, dependent on time and temperature, to inactivate pathogens and create potable water. The fluid flow may be controlled by a thermally actuated valve particularly adapted to control pulsing flow and prevent contaminated water from passing through the valve. Still further, the system may include a unique solar tracking system allowing for tracking of the sun or other tracking processes with very low power usage and high precision.

The systems, devices, and mechanisms described herein may allow for thermal heating and/or thermal pasteurization of water in remote areas of the world or in conditions of power loss, catastrophic event, war, or other situations. The system may do so substantially automatically, with little to no human interaction and little to no reliance on public utilities, networks, or other utility, electrical, information, or other infrastructure. The system may include its own power source that may be capable of sustaining the operation of the system for extended periods of time, and without connection to exterior power sources. The tracking system provided on the system may be used for solar tracking, such as for the present device, or it may be used to track other items such as satellites, planets, or other objects having known or identifiable positions relative to the position of the device. Various purposes may exist for tracking of these or other devices or objects. Still other implementations of the present system or one or more of its devices or mechanisms may be provided.

Figure 1:
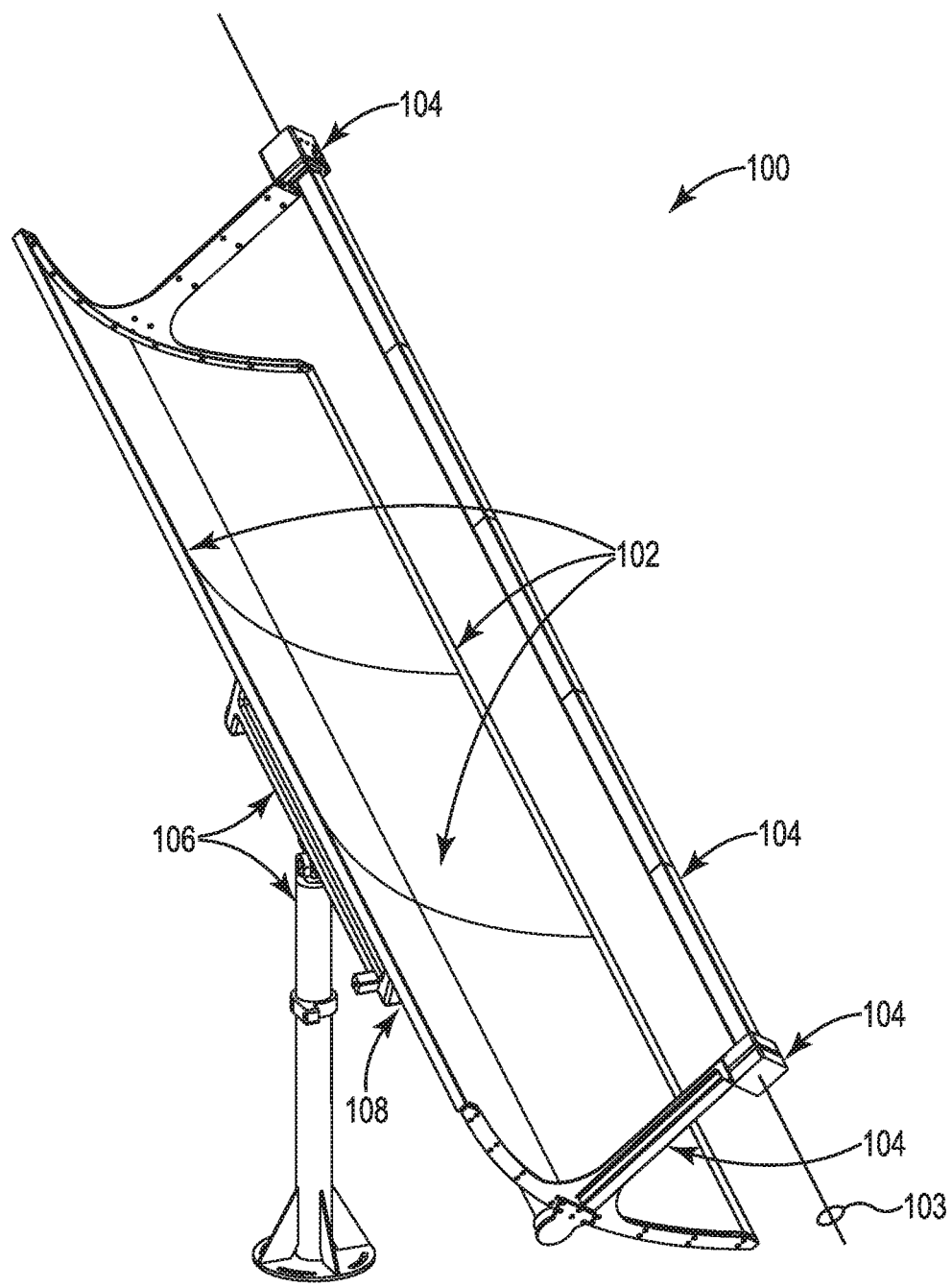
FIG. 1 is a perspective view of a fluid heating system, according to one or more embodiments.

Referring to FIG. 1, a perspective view of a fluid heating system 100 is shown. On a system level, the fluid heating system 100 may include a solar collection system 102, a fluid control system 104, a support structure 106, and a tracking system 108. The solar collection system 102 may be configured for collecting and focusing solar energy at a focal point or a focal axis 103. The fluid control system 104 may be configured for storing fluid to be treated, treating the fluid by transporting the fluid along the focal axis 103, and storing the treated fluid. The support structure 106 may be configured for operably supporting the solar collection system and one or more portions of the fluid control system. The tracking system 108 may be configured for manipulating the support structure 106, or portions thereof, thereby adjusting the position and orientation of the solar collection system 102 and one or more portions of the fluid control system 104 in a manner that allows for efficient collection of solar energy and efficient heating of fluid.

Solar Collection System

Figure 2:
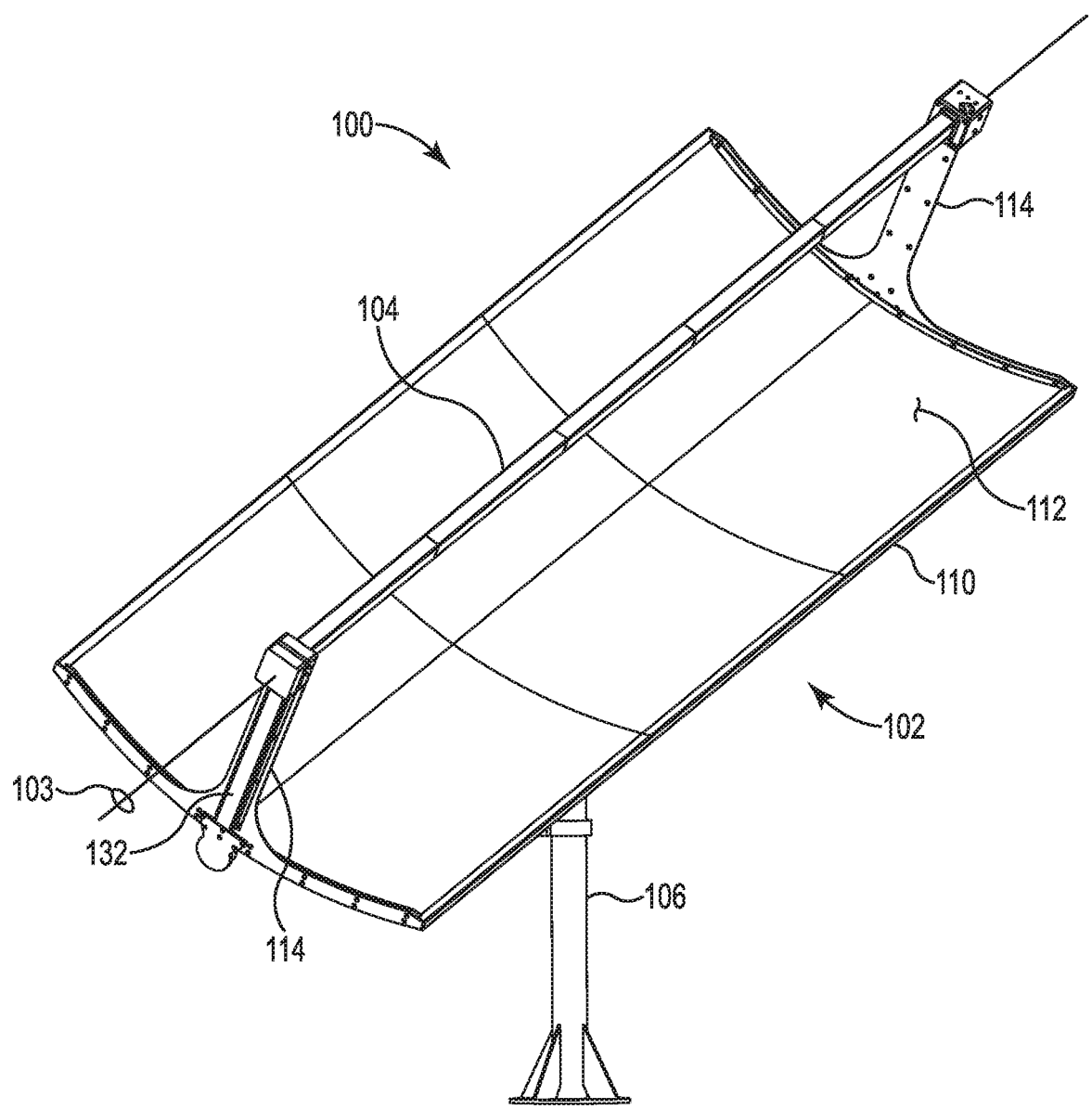
FIG. 2 is a perspective view of a solar collection system portion of the fluid heating system, according to one or more embodiments.
Figure 3:
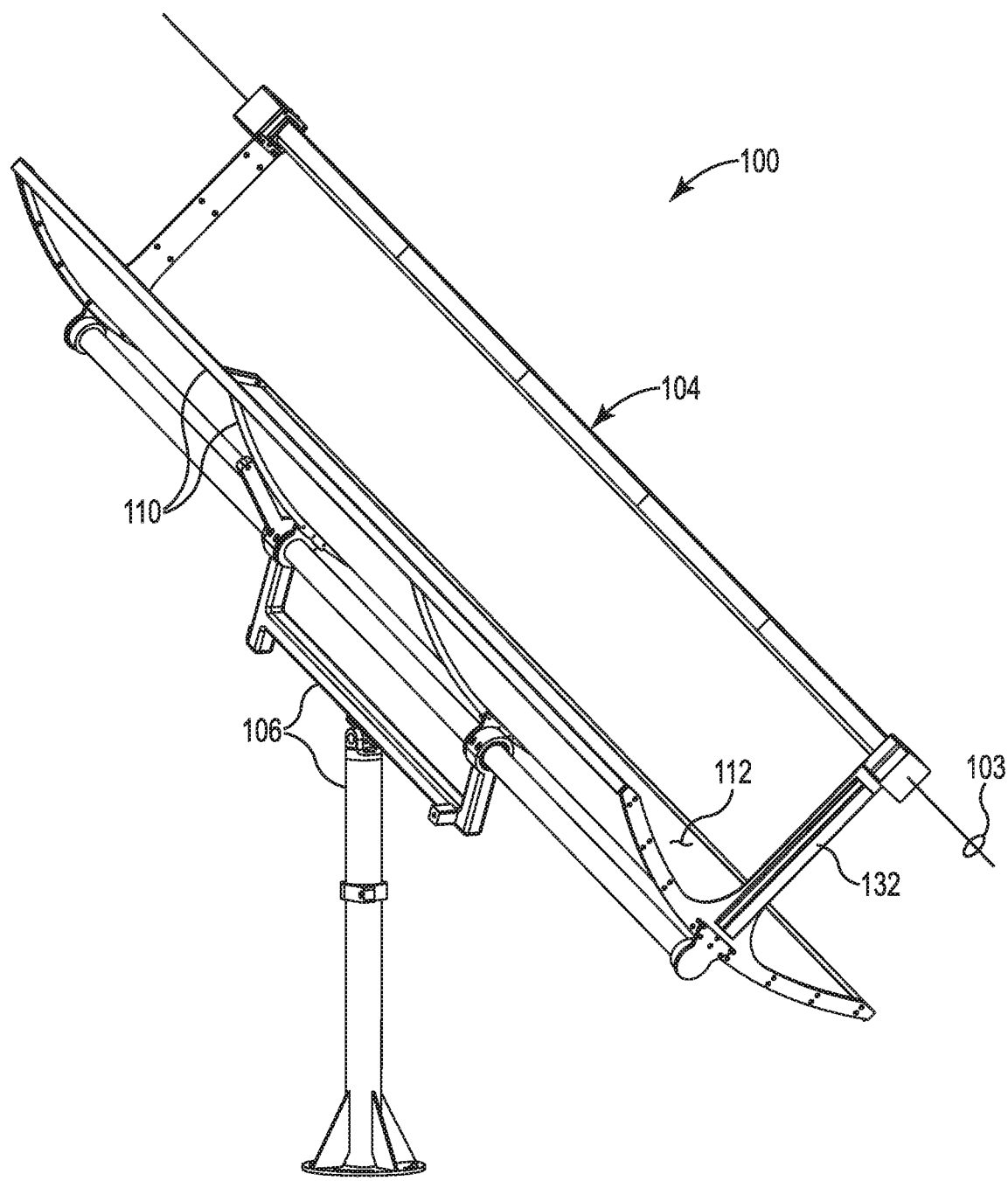
FIG. 3 is a side and back view thereof, according to one or more embodiments.

With reference to FIGS. 2 and 3, the solar collection system 102 may include a frame 110, a reflective element 112, and one or more upright fluid control support elements 114. The frame 110 may be configured to define the size and shape of the solar collection system 102 and to provide a framework for the reflective element 112. The reflective element 112 may be configured to receive sunlight or other radiation and reflect that sunlight or other radiation toward a common focal point or axis 103. The upright fluid control support elements 114 may be configured for supporting the fluid heating element of the fluid control system 104 at a substantially rigid position relative to the reflective element 112 and, in particular, at the focal point or along the focal axis 103. Each of the particular elements of the solar collection system 102 may be described in more detail below.

Figure 4:
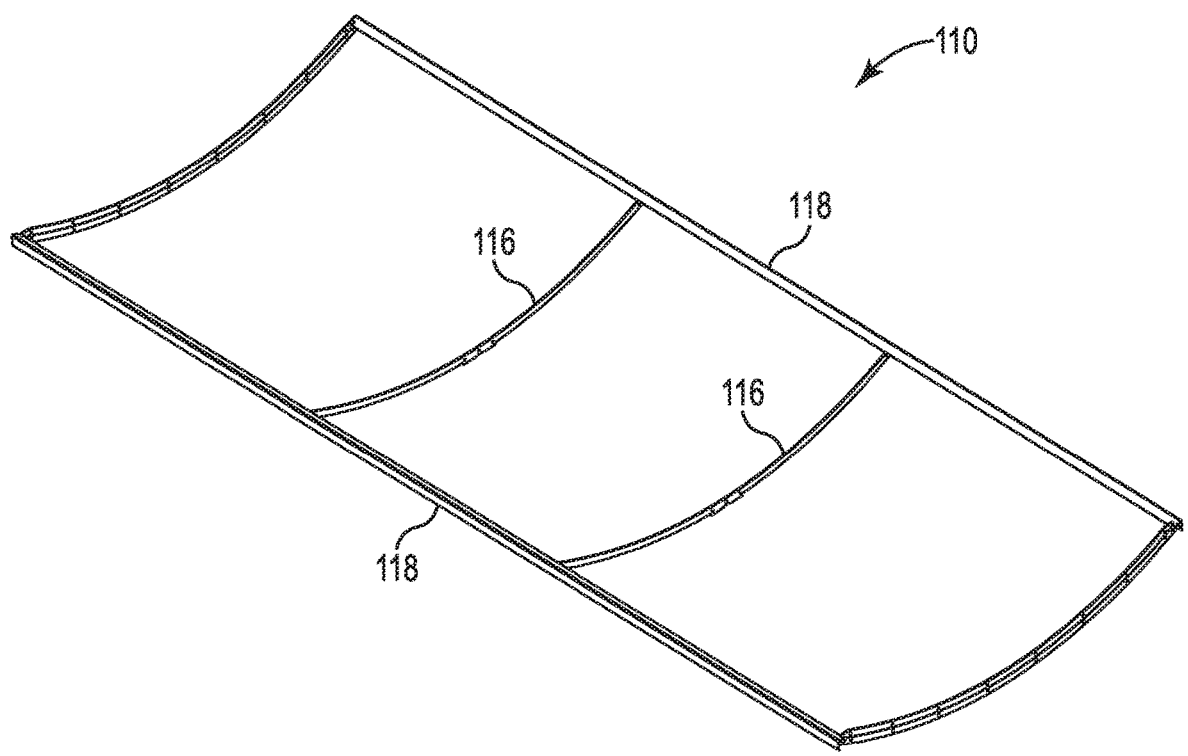
FIG. 4 is a perspective view of a frame portion of the solar collection system, according to one or more embodiments.

Referring now to FIG. 4, the frame 110 may include a plurality of laterally extending ribs 116 and a pair of longitudinally extending rails 118. The ribs 116 may be configured to define a parabolic or other shape and provide spaced apart support of the reflective element 112 along its length. The rails 118 may be configured to provide support and inward acting resistance along the edges of the reflective element 112.

Figure 5:
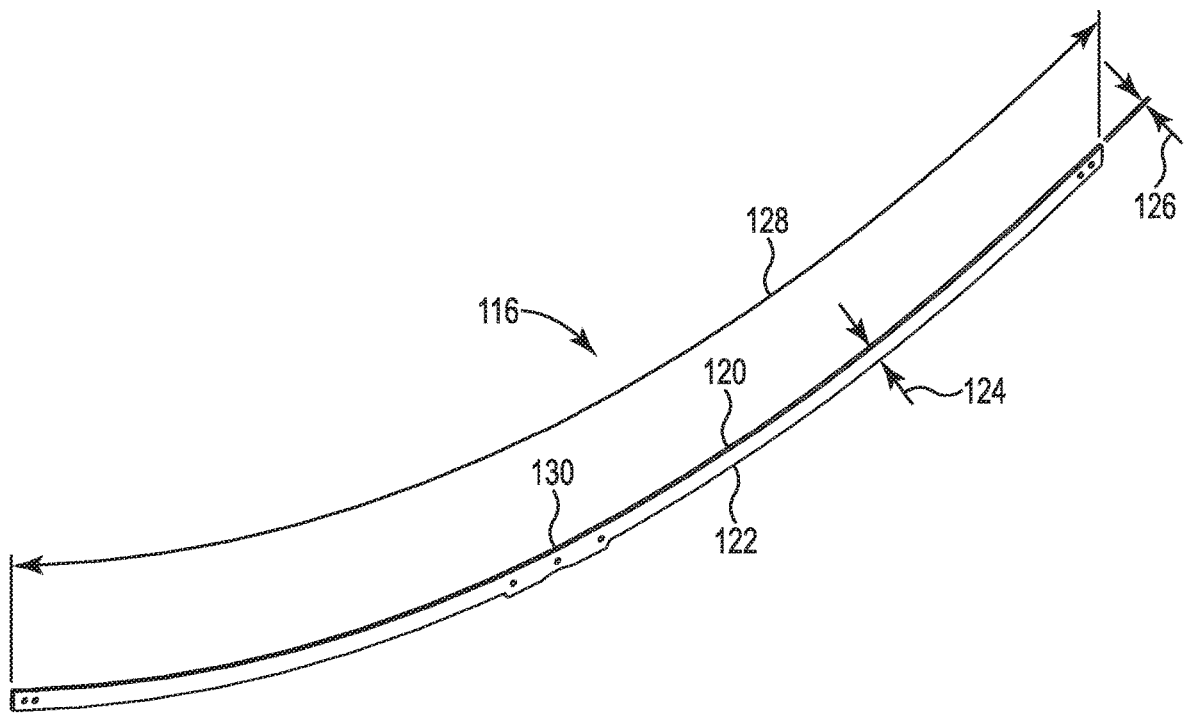
FIG. 5 is a perspective view of a rib of the frame portion, according to one or more embodiments.

Referring to FIG. 5, the ribs 116 may be in the form of a bar, plate, angle, tube, pipe, or other substantially elongate element having a curved shape or surface for defining the shape of the reflective element. In one embodiment, the ribs may include a top surface 120 having a parabolic or other curved shape. In some embodiments, the top surface 120 may be due to the rib being formed or shaped. In other embodiments, the top surface 120 may be created by cutting the shape into the rib. In some particular embodiments, the ribs 116 may be plate elements configured to be arranged on edge and the top surface 120 and bottom surface 122 may be defined by substantially parallel curves offset from one another defining a rib depth 124. The ribs 116 may have a thickness 126 of approximately 1/16 inch to approximately 1/4 inch, or approximately 1/8 inch to approximately 3/16 inch. Still other thicknesses may be provided. The ribs 116 may have a depth 124 ranging from approximately 1/4 inch to approximately 4 inches, or approximately 1/2 inch to approximately 2 inches, or approximately 3/4 inch to approximately 1 inch. The ribs 116 may have a length 128 dependent on the size of the solar collection system 102 and may range from approximately 6 inches long to approximately 10 feet long, or approximately 1 foot to approximately 6 feet, or from approximately 2 feet to approximately 4 feet.

The curvature of the top surface 120 or the portion engaging the back side of the reflective element 112 may be parabolic. In some embodiments, the curvature may be based on a function such as $f(x)=x^2$. In other embodiments, the curvature may be based on a function such as $f(x)=x^2-mx$. The focal axis 103 of the reflective element 112 may be based on the curvature of the ribs 116 and may range from approximately 6 inches to approximately 8 feet, or approximately 1 foot to approximately 4 feet, or approximately 2 feet to approximately 3 feet, or approximately 24 inches to approximately 26 inches above the vertex 130 of the ribs, for example.

Referring to FIGS. 3 and 4, the ribs 116 may be arranged along the back side of the reflective element 112, may engage and be supported by the support structure 106, and may support the reflective element 112 in spaced apart relation. In particular, the ribs 116 may be spaced along and secured to the spine element of the support structure 106 with a bracket, tab, or other connecting element suitable for bolting the ribs 116 to the spine or a welded connection may be used.

Figure 6:
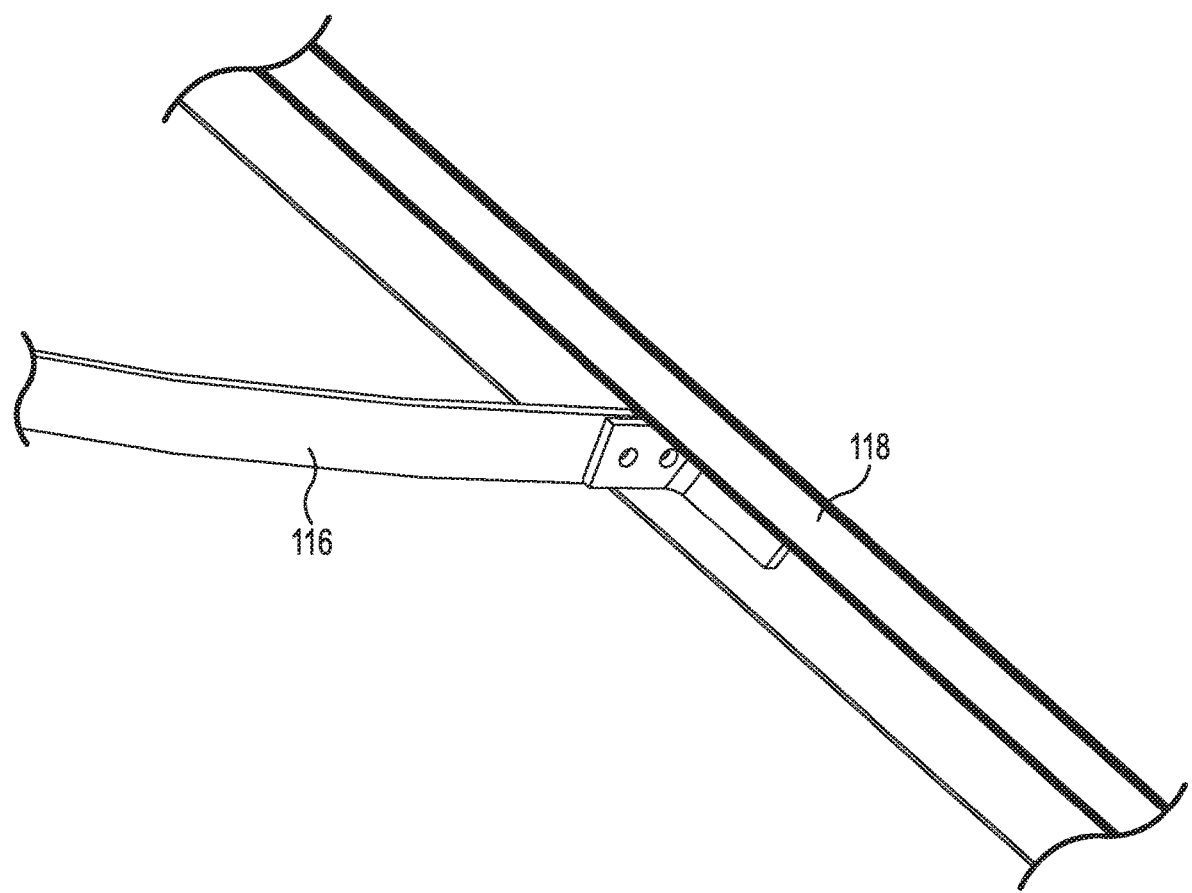
FIG. 6 is a perspective view of a connection of a rib and a longitudinal rail, according to one or more embodiments.

With reference to FIG. 6, like the ribs 116, the longitudinal extending rails 118 may be in the form of a bar, plate, angle, tube, pipe, or other substantially elongate element. However, in contrast to the ribs 116, the rails 118 may have a substantially straight shape for extending along the side of the reflective element 112, for resisting lateral and outward motion of the reflective element 112, and for protecting the edge of the reflective element 112. In some particular embodiments, the rails 118 may be angle elements having an angle-shaped cross-section. The angle may be arranged with one leg of the angle directed inwardly toward the reflective element 112 and the other leg of the angle directed downwardly alongside the edge of the reflective element 112. That is, for example, the inwardly extending leg may be placed along the edge of the reflective element 112 and on the top surface of the reflective element 112 and the downwardly extending leg may extend down past the reflective element 112. As the rail 118 extends along the reflective element 112 and passes by the ends of the ribs 116 spaced along the structure, the rails 118 may be secured to the ribs 116. As such, any outward force from the compressively shaped reflective element 112 may be resisted by abutment with the downwardly extending leg of the rail 118 and its securement to the ribs 116.

The legs of the angle-shaped rail may have a thickness of approximately 1/16 inch to approximately 1/4 inch, or approximately 1/8 inch to approximately 3/16 inch. Still other thicknesses may be provided. The legs of the angle may range from approximately 1/2 inch to approximately 8 inches, or approximately 3/4 inch to approximately 2 inches, or approximately 1 inch to approximately 1½ inch. Still other angle sizes may be provided and the legs of the angle may be the same or different.

Figure 7:
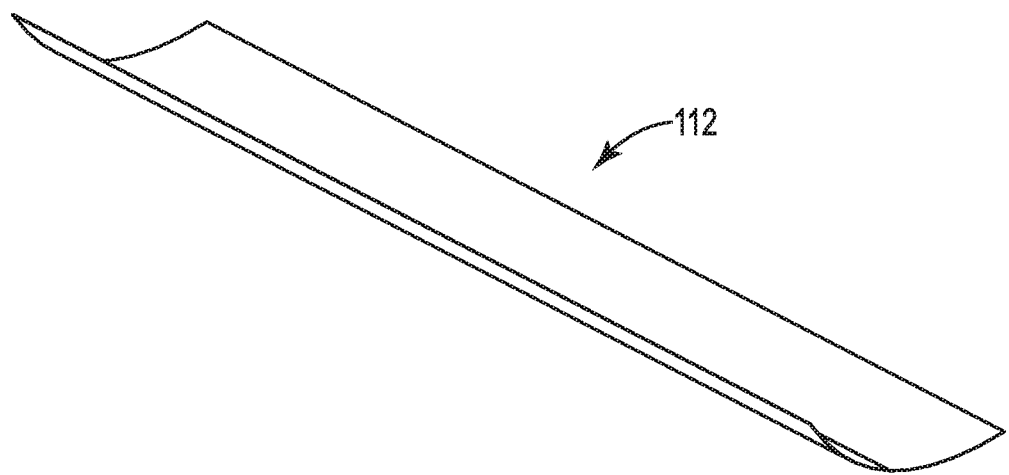
FIG. 7 is a perspective view of a reflective element of the solar collection system, according to one or more embodiments.

Referring now to FIG. 7, the reflective element 112, which may be substantially flat in an unassembled condition, may be placed, positioned, or arranged on top of the frame 110 and it may be pressed downwardly into the trough-shaped frame 110. Along the ends of the reflective element 112, keeper strips may be placed on top of the reflective element 112. Fasteners may extend through the keeper strips and into one or more ribs 116 arranged below the end of the reflective element 112. These keeper strips, together with adhesive between the back of the reflective element 112 and the ribs 116, and the resistance from the rails 118 may all function together to secure the reflective element 112 in position on the frame 110.

The reflective element 112 may include a membrane, film, sheet, or other relatively flat element having an upper and a lower surface where the upper surface is relatively, substantially, or highly reflective. In some embodiments, the reflective element 112 may include a series of plies or layers adhered together to form the reflective element. In some embodiments, the reflective element may be a generally flat element in an unassembled condition and the relatively flat element may be held in a substantially curved and/or parabolic shape by the frame portion 110. In other embodiments, the reflective element 112 may be fabricated to have a curved and/or parabolic shape on its own without the frame portion.

In some embodiments, the reflective element may include a plurality of layers. In some embodiments, one layer may be a reflective film or layer such as a 3M solar film or other all-polymeric mirror film or partial polymeric mirror film. In some embodiments, the film may be wavelength selective. In embodiments, the film may be a high reflectivity, no scatter type film. Still other reflective films may be used.

The film may be laminated onto a backing material to provide an increased level of rigidity and/or uniformity and to provide scratch resistance and other protection during shipping. That is, the reflective film material may be relatively thin and flexible and may be akin to a paper, plastic film, or other relatively flexible and foldable material. In contrast, while remaining formable, the backing material be a more rigid and yet flexible material. In some embodiments, the backing material may include a relatively thin gauge material such as a plastic, metal such as aluminum, steel, stainless steel, or other metal, or another thin gauge material may be provided. In some particular embodiments, the backing material may include stainless steel material having a gauge ranging from approximately 36 gauge to approximately 1/4 inch, or from approximately 30 gauge to approximately 1/8 inch, or from approximately 28 gauge to approximately 20 gauge, or a thickness of approximately 21, 22, 23, 24, 25, 26, or 27 gauge may be used. The gauge selected may be selected to arrive at a low weight system that also provides for a substantially flat surface for the reflective film that is also substantially dent resistant.

The several layers of the reflective element 112 may be laminated together to form the reflective element 112. In some embodiments, the several layers may be laminated as a flat or substantially flat sheet. In some embodiments, the layers may be laminated with an adhesive such as a pressure sensitive adhesive or other adhesive.

Figure 8:
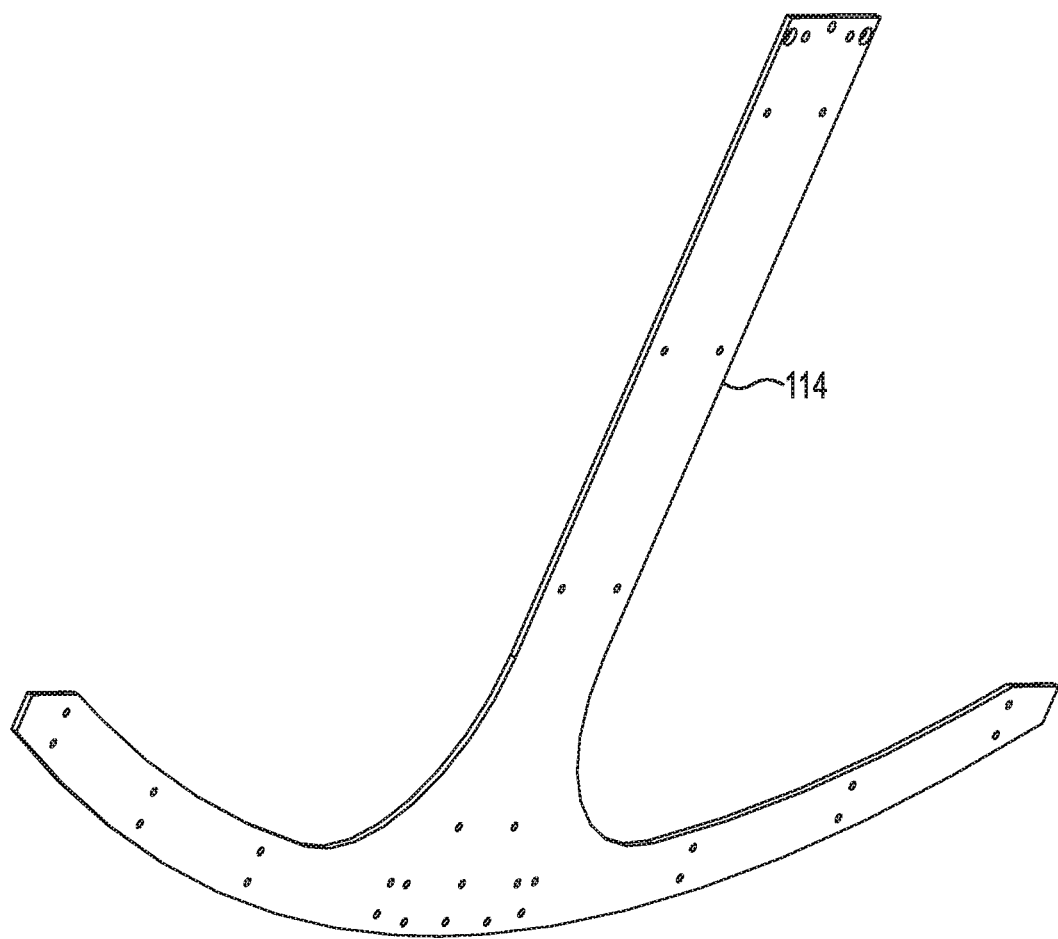
FIG. 8 is a perspective view of a fluid portion support element of the solar collection system, according to one or more embodiments.

Turning now to the upright fluid control support elements 114, as shown in FIG. 8, these elements may be positioned on each end of the frame 110 and may be configured to support a portion of the fluid control system 104. In particular, these elements may be configured to support the fluid heating element and position the fluid heating element along the focal axis 103 of the reflective element 112.

The upright fluid control support elements 114 may be secured to the ribs 116 of the frame 110 at the end of the frame 110 or may serve as a rib 116 at each end. That is, one or more upright fluid control support elements 114 may be positioned at each end and may extend upwardly at or near the vertex of the curvature of the reflective element 112 and up to or near the position of the focal axis 103. The upright fluid control support element 114 may be a plate, pipe, tube, angle, or other shape. In some embodiments, as shown in FIGS. 2 and 3, the upright fluid control support element 114 may include a tube guide 132 for incoming and effluent lines at the end of the system where the untreated water is entering the system and where the potable water is exiting. In some embodiments, the tube guide 132 may begin near the bottom of the upright element 114 and extend to a position at or near the top. In some embodiments, the tube guide 132 may be insulated to as to protect against user injury and/or exposure to relatively hot lines due to exiting hot water.

The above-described solar collection assembly 102 may include substantially flat elements, which may be useful for purposes of shipping. That is, the frame 110 including the ribs 116 and the longitudinal rails 118, the reflective element 112, and the upright fluid support elements 114, may include substantially flat, plate-like or substantially plate-like elements. For example, the ribs 116, while curved, may be plate-like and, as such, when unassembled and laid on their side, may be substantially flat. Similarly, the longitudinal rails 118 may also be plate-like or substantially plate-like in the form of angles, for example. The reflective element 112 may be a laminated film and, as such, without support by the frame, the reflective element 112 may be substantially flat. In addition, the upright fluid support elements 114 may also be plate-like or substantially plate-like allowing them to lay substantially flat when disconnected from the frame 110.

When the solar collection system 102 arrives at its location, it may be assembled to form the solar collection system 102 as shown in FIGS. 1-3. The solar collection system 102 may be positioned atop or supported by the support structure 106 described in more detail below.

Fluid Control System

As mentioned, the fluid control system 104 may be configured for storing fluid to be treated, treating the fluid by transporting the fluid along the focal axis 103, and storing the treated fluid. It should be appreciated that while the fluid control system 104 is being described in conjunction with the solar collection system 102, the fluid control system 104 may be used with alternative sources of heat. For example, the fluid control system 104 may be arranged for exposure to burning fuels such as coal, wood, propane, natural gas, or other fuels. In still other embodiments, the fluid control system 104 may be arranged for exposure to electrical sources of heat, such as electric heaters, heat traces, or other sources of electrical heat. The fluid control system 104 may be used with any source of heat and functions to control the flow of fluid through the system based on the temperatures the fluid reaches. As such, the amount or type of heat supplied, while relevant to the rate at which the system may supply potable water or other treated fluid, is not limited to the solar collection system 102 mentioned.

Figure 9:
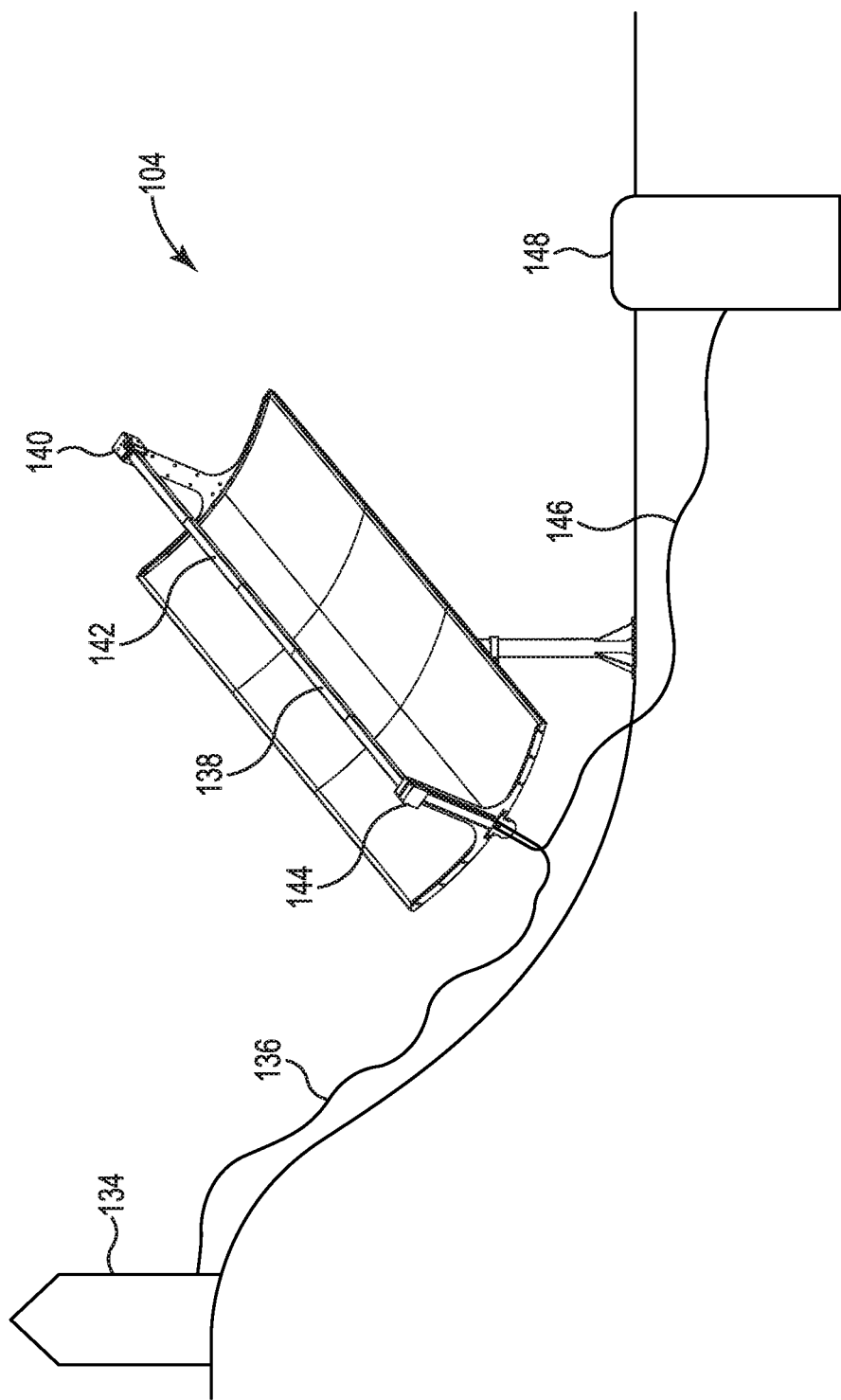
FIG. 9 is a perspective view of a fluid control system of the fluid heating system, according to one or more embodiments.

As shown in FIG. 9, the fluid control system 104 may include a collection reservoir 134, a feed line 136, a fluid heating element 138, a flow control assembly 140, a return line 142, a preheat heat exchanger 144, an effluent line 146, and a treated fluid reservoir 148. The collection reservoir 134 may be configured to collect water or other fluid from one or more sources and hold the fluid until the system is available to treat the fluid. The feed line 136 may be configured to carry the fluid from the collection reservoir to the fluid heating element. The fluid heating element 138 may be configured to expose and/or hold the fluid in position relative to a heat source. The flow control assembly 140 may control the flow of the fluid through the fluid heating element 138 such that the fluid is sufficiently exposed to the heat source. The return line 142 may be configured to receive the fluid from the control valve 140 and carry the fluid along the fluid heating element 138 toward the entrance to the fluid heating element 138. The preheat heat exchanger 144 may be configured to thermally expose the treated fluid from the return line 142 to the incoming fluid from the feed line 136 so as to preheat the incoming fluid as it enters the fluid heating element 138 and to simultaneously cool the treated fluid. The effluent line 146 may carry the fluid away from the system to the treated fluid reservoir 148. The treated fluid reservoir 148 may be configured to collect treated fluid and store the treated fluid until it is used.

With continued reference to FIG. 9, the collection reservoir 134 may be in the form of a tank. The tank may include most any type of tank including pre-fabricated tanks or tanks constructed on site. In the case of on-site constructed tanks, the tank may be a flat bottom concrete tank or a steel tank of bolted or welded construction and the tank may include a liner. In some other embodiments, the tank may be an elevated concrete tank, an elevated steel tank of bolted or welded construction, or a composite elevated tank, for example, may be provided. In other embodiments, the collection reservoir 134 may be a polypropylene, polyethylene or other polymeric material suitable for collecting and storing water or other fluid. In still other embodiments, the collection reservoir 134 may be a fiberglass material, wood material, or other material. Still other types of tanks may be contemplated and used.

The collection reservoir 134 may collect water or other fluid from one or more sources. For example, the reservoir 134 may collect water from lakes, rivers, public reservoirs, public or private distribution systems and the like. In some embodiments, the collection reservoir 134 may be gravity fed by these systems and may include a shutoff or other valve for avoiding overflow situations. In other embodiments, the collection reservoir 134 may include a pump arranged in a water or fluid source that may pump the water to the collection reservoir 134 when the reservoir is low on water or fluid. In some embodiments, the collection reservoir 134 may collect rain water and may be used in conjunction with a land basin or other basin configured to collect rainwater and/or other runoff.

The reservoir 134 may be a single tank or multiple tanks may be provided. For example, where multiple sources of fluid or water are available, but are not conducive to feeding a single tank, multiple tanks may be used. In some embodiments, multiple systems may rely on a centralized or community tank. For example, a city, township, village, or other group of users may rely on a single tank or a series of tanks all of which may be positioned to take advantage of a particular source of water or fluid.

In some embodiments, the collection reservoir 134 may be positioned relative to the system so as to gravity feed the system. As such, the collection reservoir 134 may be located at an elevated position relative to the system such as up on a hill, on a structural pedestal, on a roof, or on another elevated structure or land formation. Where the location of collection is not in an elevated position relative to the system treating the water, multiple tanks may be provided. For example, a first collection reservoir 134 may be provided at the location conducive to collection and a pump may be provided to pump the water to a second tank or reservoir 134 conducive to feeding the system. In some embodiments, the pump may be run at off peak hours or otherwise used in a manner to reduce costs incurred by using the system.

It should be appreciated that while a tank or series of tanks have been mentioned, the collection reservoir 134 may also take several other forms such as a basin, a lake, a river, an open pit, an open trough, or other container, structure, or land formation that is capable of at least temporarily holding water or other fluid. That is, in addition to other types of tanks, where the system is being used at or near a relatively continuous either static or flowing source of water or fluid, the collection reservoir 134 may take the form of such source of water or fluid.

A feed line 136 is also shown in FIG. 9. The feed line 136 may be in fluid communication with the collection reservoir 134 so as to provide a continuous, substantially continuous, or periodic supply of fluid or water to the fluid heating element 138. The feed line 136 may be tapped into the collection reservoir at or near the bottom, for example, so as to receive water or fluid from the collection reservoir 134 unless or until the collection reservoir 134 is nearing an empty condition. The feed line 136 may be tapped in slightly above the bottom to allow an area in the collection reservoir 134 for sediment or other debris to settle out without flowing into the system. The feed line 136 may extend from the collection reservoir 134 to the fluid heating element 138 via the preheat heat exchanger 144. The feed line 136 may be a polypropylene, polyethylene, or other polymeric material or another material may be used. The feed line 136 may be sized to accommodate the flow of fluid or fluid to the system without overly constraining flow and, as such, the feed line 136 may have a diameter and/or cross-sectional flow area reasonably similar to the diameter or cross-sectional flow area of the fluid heating element 138. In some embodiments, the feed line 136 may be a ½ inch, ¾ inch, 1 inch, 1½ inch, 2 inch, or 3 inch line, for example. In still other embodiments, other size feed lines 136 may be used.

Figure 10:
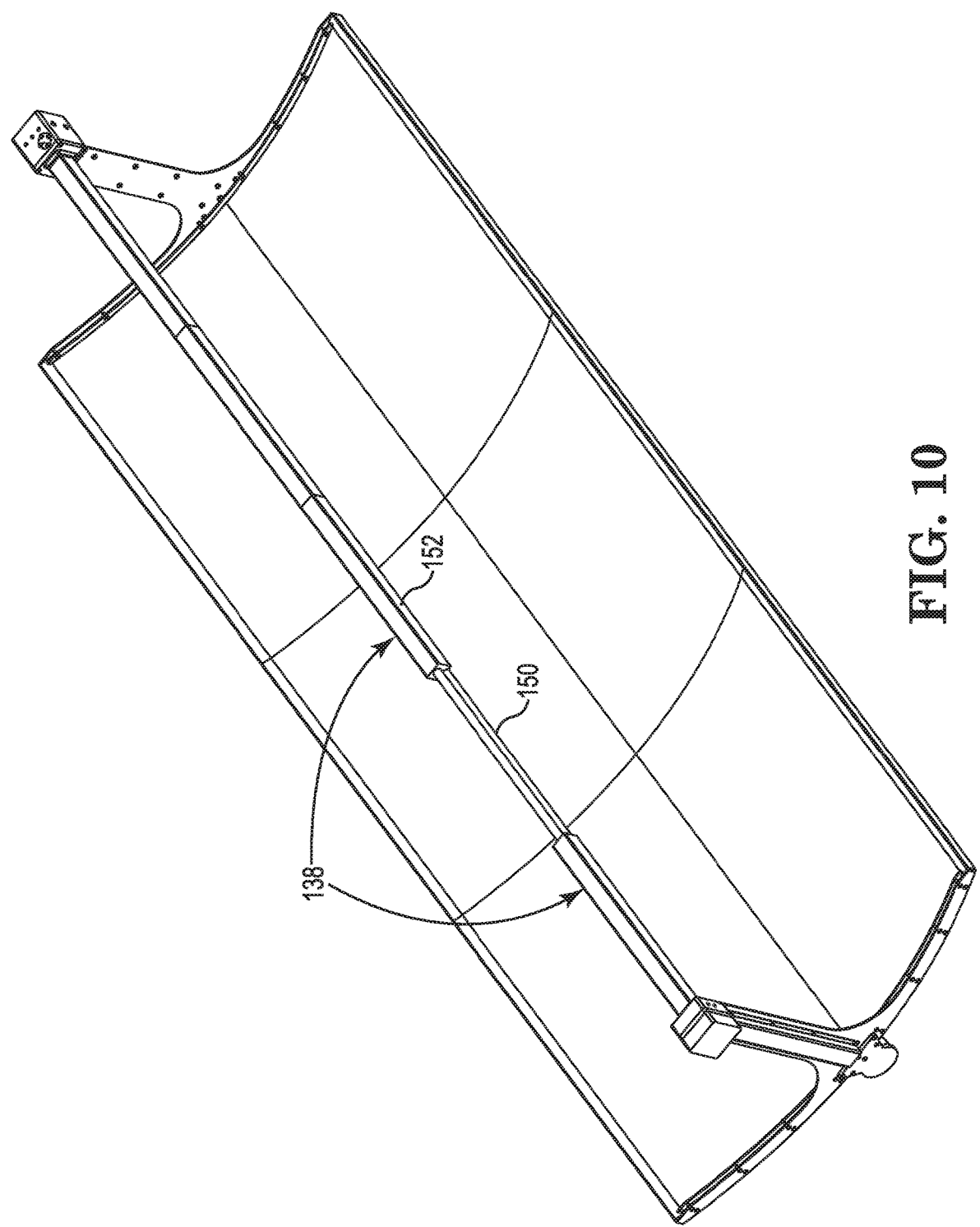
FIG. 10 is a close-up perspective view of portions of the fluid control system, according to one or more embodiments.

Referring now to FIG. 10, the fluid heating element 138 is shown. The fluid heating element 138 may include an elongated flow element 150 and a housing 152. The elongated flow element 150 may be configured to transport the water or fluid along the focal axis 113 of the solar collection system 102 or along another heat source and cause the water or other fluid to be heated. The housing 152 may be configured for insulating a portion of the elongated flow element 150. The housing 152 may also be configured for controlling or reducing convective flow of air relative to the elongated flow element 150.

Figure 11:
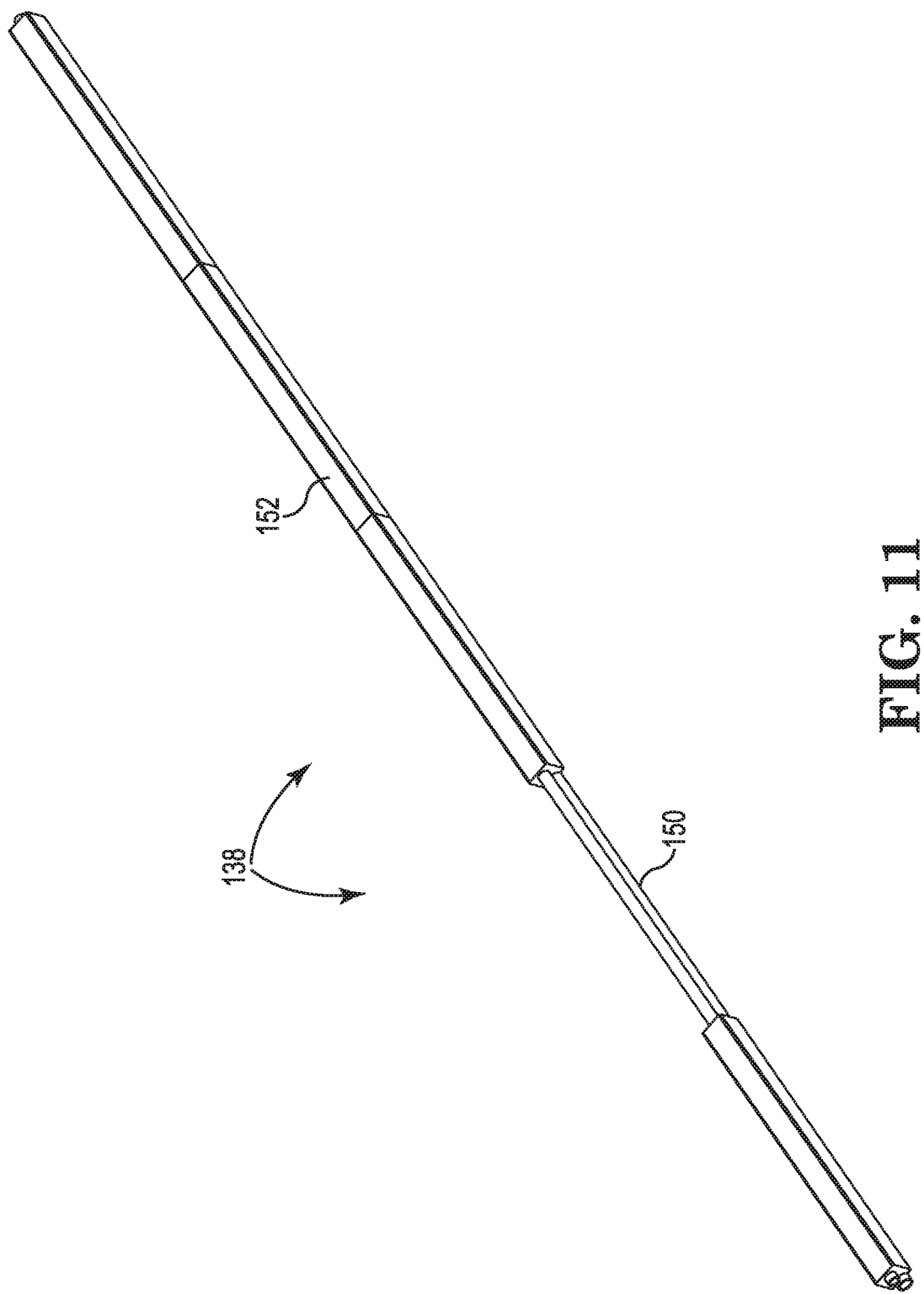
FIG. 11 is a perspective view of a fluid heating element of the fluid control system, according to one or more embodiments.

As shown in FIG. 11, the elongated flow element 150 may be in the form of a pipe, tube, or other lumen providing shape. The elongated flow element 150 may include an exposed side and a non-exposed side where the exposed side is the side exposed to the heat source and the non-exposed side is the side opposite the heat source. In some embodiments, the elongated flow element 150 may be a symmetrical shape having a wall thickness that is substantially consistent around its perimeter. In other embodiments, the exposed side may have a wall thickness less than the non-exposed side. The elongated flow element 150 may be constructed of a conductive material so as to conduct the heat from the heat source and transfer that heat to the water or fluid flowing therethrough. While conductive, the elongated flow element 150 may also be constructed of a material that can withstand exposure to extreme heat without excessive levels of deformation, elongation, and the like. In some embodiments, the elongated flow element 150 may include a coefficient of thermal expansion ranging from approximately $10 \times 10^{-6}$ 1/C to $200 \times 10^{-6}$ 1/C. In some embodiments, the elongated flow element may include a melting point ranging from approximately 160 degrees C. to approximately 1500 degrees C. In some embodiments, the elongated flow element 150 may include a steel, stainless steel, lead, copper, or other pipe, for example. The elongated flow element 150 may be coated with a high emissivity coating to allow the elongated flow element 150 to effectively absorb the energy focused on it by the solar collector 102.

Figure 13A:
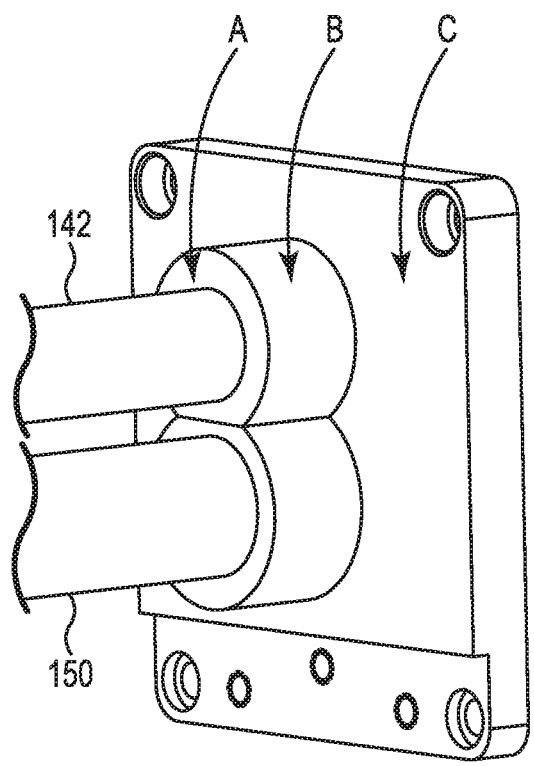
FIG. 13A is a perspective view of an engagement detail of the elongated flow element and the return line, according to one or more embodiments.
Figure 13B:
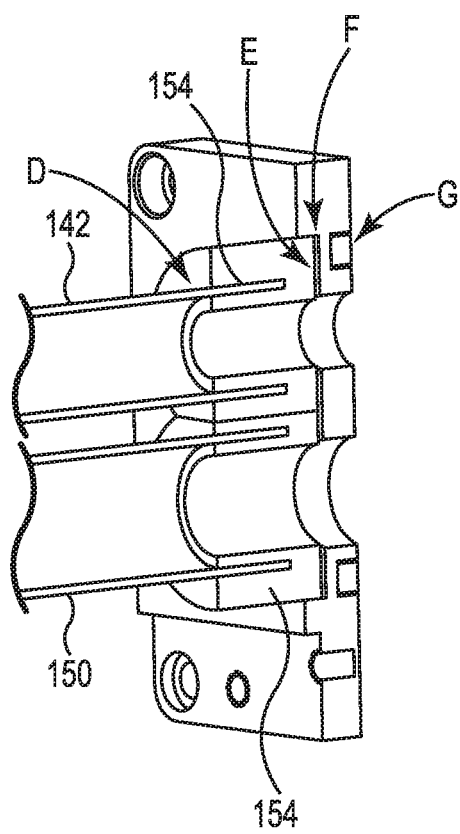
FIG. 13B is a cross-sectional view thereof, according to one or more embodiments.

The elongated flow element 150 may engage the preheat heat exchanger 144 at an inlet end of the elongated flow element 150. The elongated flow element 150 may engage the flow control assembly 140 at an outlet end of the elongated flow element 150. At each of these connections, an expansion joint 154 may be provided to allow for at least some of the expansion of the elongated flow element 150 relative to the upright support elements 114 that are supporting the system the preheat heat exchanger 144 and the flow control assembly 140. As shown in FIGS. 13A and 13B, the expansion joint 154 may include an annular resilient washer or o-ring seated in an annular space where the annular washer has an outer and inner diameter that is the same or similar to the outer and inner diameter, respectively, of the elongated flow element 150. As such, the annular washer may abut each end of the elongated flow element 150 and maintain a seal against the end of the elongated flow element 150 while allowing fluid to flow therethrough. The resilient washer may be constructed from a temperature resistant material that maintains its resiliency under extreme temperature conditions. In some embodiments, the resilient washer may include high temperature Viton or other fluorocarbon elastomer. Still other materials for the resilient washer or other expansion joint elements may be provided. A same or similar detail may be provided for each end of the return line 142.

Figure 12:
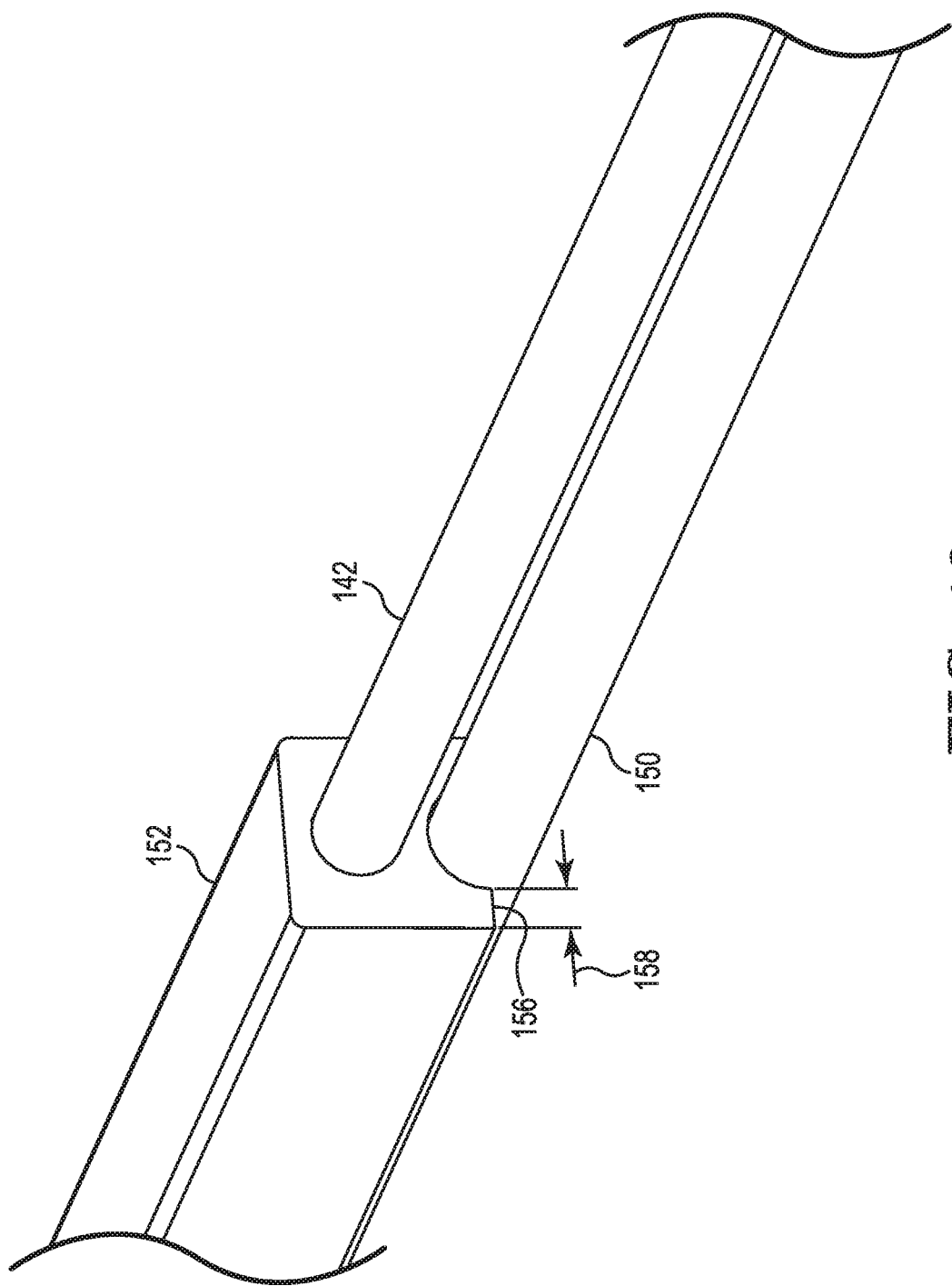
FIG. 12 is a close-up perspective view of the fluid heating element, according to one or more embodiments.

The housing 152 is shown in FIG. 12 and may be arranged on the elongated flow element 150 and may extend substantially along the full length of the elongated flow element 150. As mentioned, the housing 152 may be configured to insulate a portion of the elongated flow element 150 and may be configured to control convective air flow around the elongated flow element 150. That is, the housing 152 may be configured to reduce heat losses from the elongated flow element 150 that may occur were the elongated flow element 150 to be unprotected in this regard. In addition, the housing 152 may cover or protect portions of the elongated flow element 150 (i.e., sides and top) such that exposed surfaces that could be touched by users or otherwise contacted by living tissue are not as hot, thereby reducing burn risk.

The housing 152 may be arranged on the non-exposed side of the elongated flow element 150. As shown, the housing 152 may encapsulate, engulf, or otherwise substantially fully cover the non-exposed side of the elongated flow element 150. The housing 152 may extend partially or substantially fully along the length of the elongated flow element 150. That is, portions of the elongated flow element 150 may extend beyond the housing 152 to engage the preheat heat exchanger 144 at the inlet end or the control valve assembly 140 at the outlet end, but other areas of the elongated flow element 150 may be fully covered by the housing 152. The housing 152 may be adhered to the elongated flow element 150 with a heat resistant adhesive, such as, for example, a two-part epoxy or high temperature silicon.

In some embodiments, as shown, the housing 152 may extend around the sides of the elongated flow element 150 to about the mid-depth of the element 150. In the case of a pipe, for example, the housing 152 may extend half way around the pipe thereby exposing the bottom half of the pipe to the heat source while protecting the upper half of the pipe against heat loss and providing protection against burns. The housing 152 may include a substantially insulating material such as, for example, a ceramic material or a glass pipe with evacuated interior. Other materials useful as a housing material may include insulating fibers, composite materials, or high temperature plastics. Still other materials may also be used. The housing 152 may have a substantially round, rectangular or other shape. That is, the bottom portion of the housing 152 may conform to the outside surface shape of the elongated flow element 150 and the remaining portion of the housing 152 may have a particular shape such as a round or rectangular shape as suggested. In some embodiments, the housing 152 may be sized so as to encapsulate or include the return line 142 as well as the non-exposed side of the elongated flow element 150. In some embodiments, insulating material may be arranged between the return line 142 and the elongated flow element 150 so as to reduce the escape of energy from the elongated flow element 150 into the return line 142.

In some embodiments, in addition to insulating the elongated flow element 150, the housing 152 may extend laterally away from the sides of the elongated flow element 150 to provide a sort of hood or awning 156 adjacent the elongated flow element 150. The hood or awning 156 may be configured to resist or prevent flow of air or other fluid upward from a bottom side of the elongated flow element 150. This resistance to air flow may reduce the amount of energy that is lost from the elongated flow element 150 due to convective air currents. In some embodiments, the hood or awning 156 may extend laterally away from the elongated flow element 150 a distance related to the size of the elongated flow element 150. For example, the hood or awning 156 may extend laterally away from the elongated flow element 150 an awning distance 158 ranging from approximately ¼ of the diameter of the elongated flow element to 4 times the diameter. In other embodiments, the distance may range from approximately ½ the diameter to 2 times the diameter, or from approximately 1 times the diameter to 1½ times the diameter. The awning or hood 156 may extend substantially horizontally (i.e., along the lateral centerline of the elongated flow element 150 or pipe) away from the elongated element 150 or the awning or hood 156 may be angled slightly upward or downward relative to the horizontal.

Figure 14:
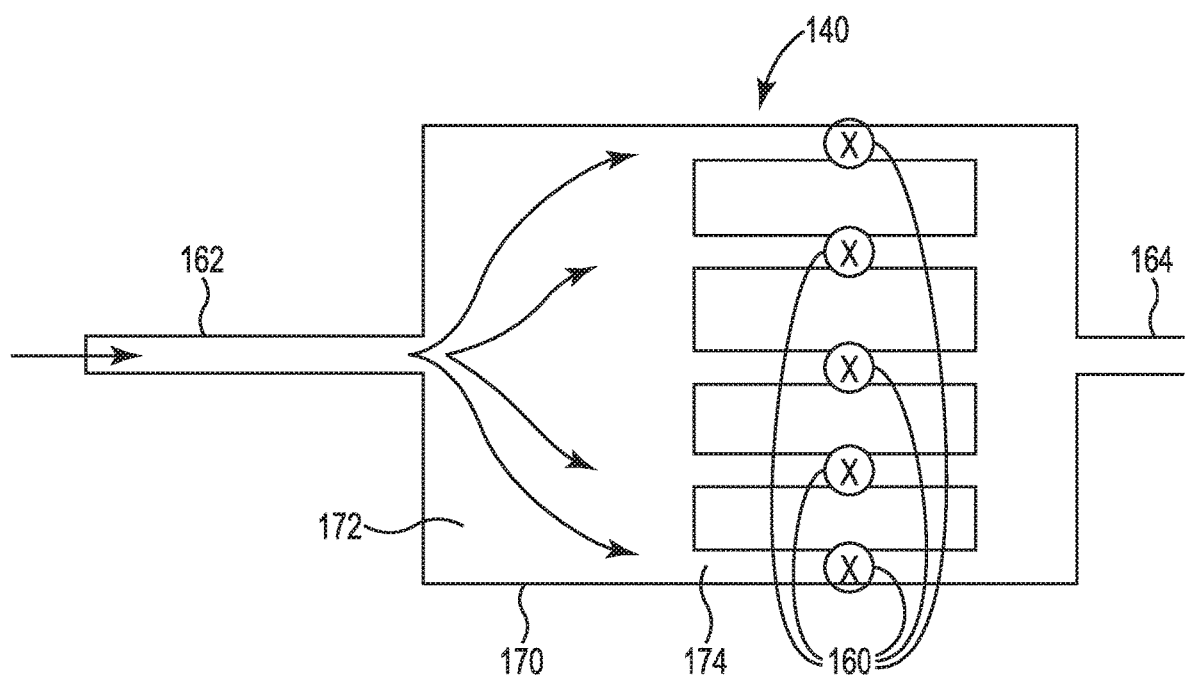
FIG. 14 is a schematic diagram of a flow control assembly, according to one or more embodiments.
Figure 15:
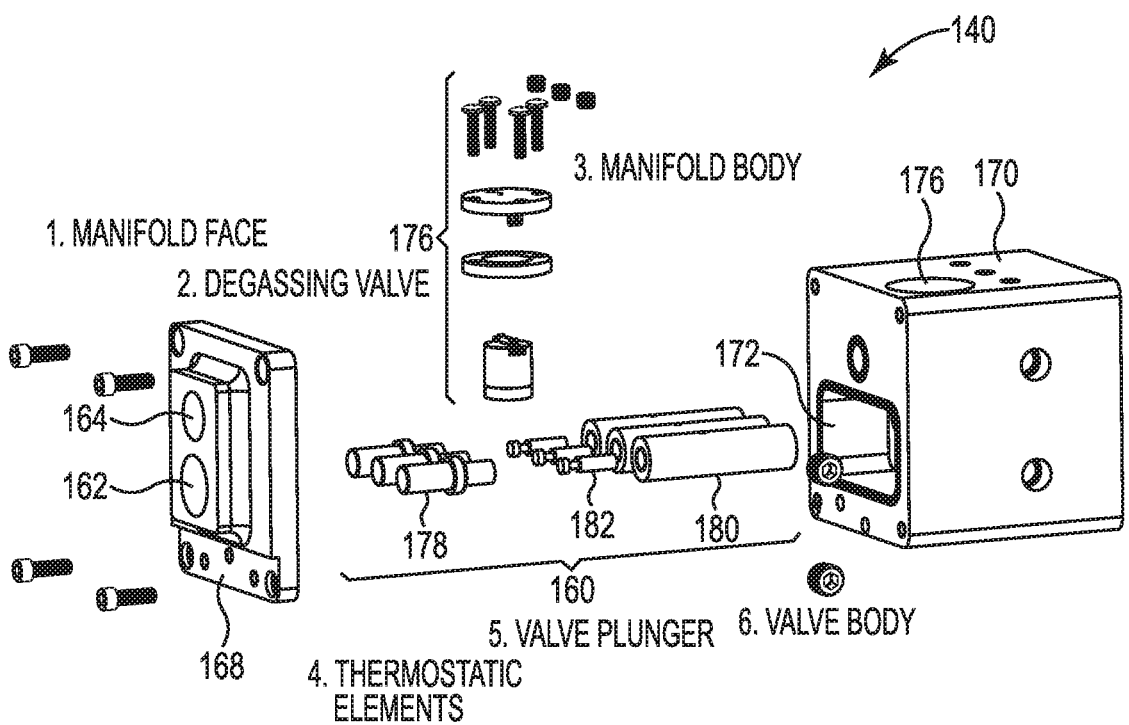
FIG. 15 is an exploded view of a flow control assembly, according to one or more embodiments.
Figure 16:
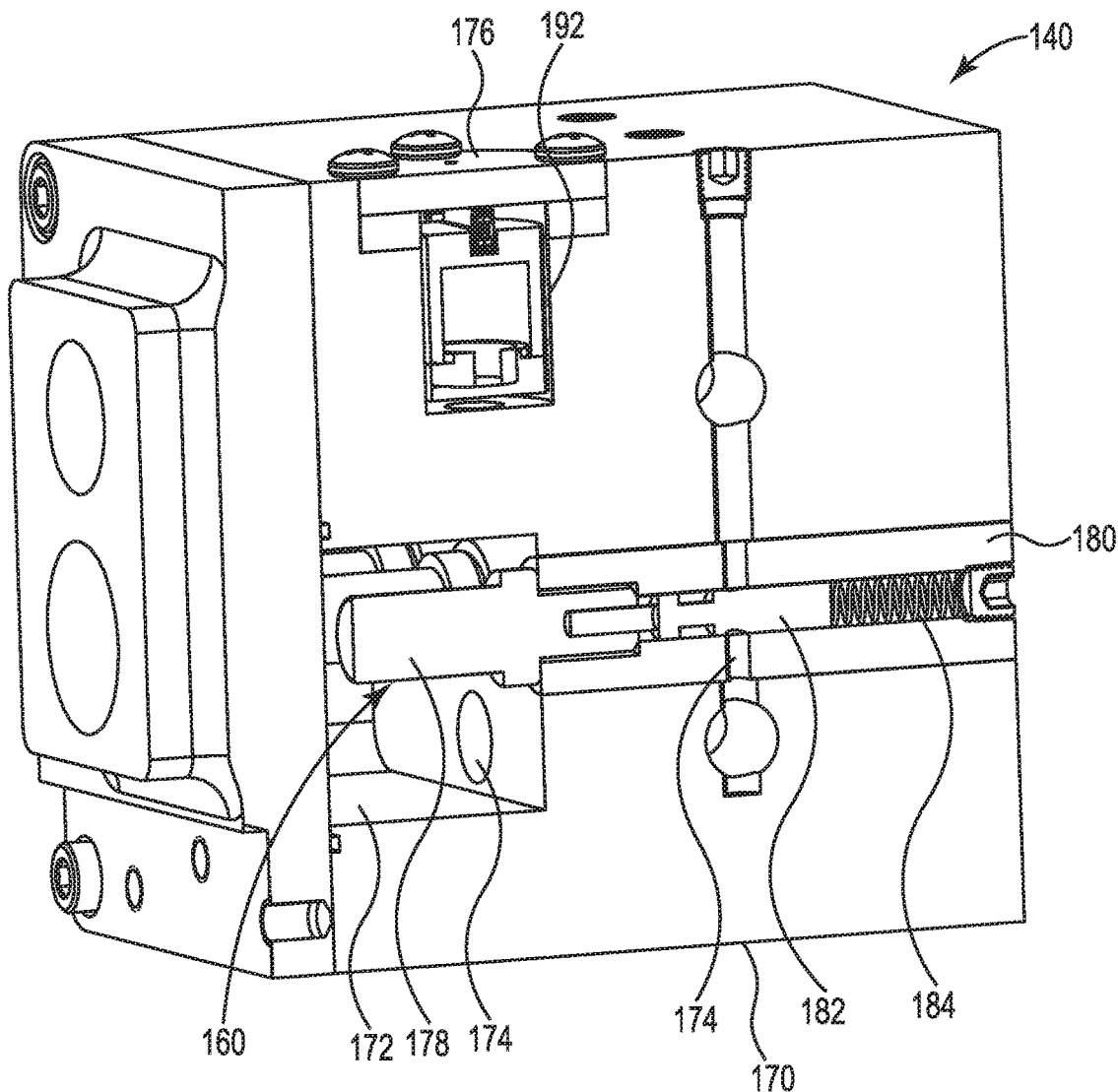
FIG. 16 is a cross-sectional view thereof, according to one or more embodiments.

Turning now to FIGS. 14-16, the flow control assembly 140 may provide controlled flow of treated fluid from the elongated flow element 150 to the return line 142. In some embodiments, the flow control assembly 140 may be positioned downstream of the fluid heating element 138 and upstream of the treated water reservoir 148. In one embodiment, the flow control assembly 140 may be positioned at an end of the solar collector opposite the entry end. The flow control assembly 140 may be configured to allow pasteurized fluid to pass through the assembly 140 and may help to prevent unpasteurized fluid from passing through, thereby avoiding contamination of fluid present in the treated water reservoir 148. Such controlled flow of the treated fluid is desirable in order to regulate fluid pressures in the system and also to monitor temperature of the fluid entering the return line 142 in order to reduce, and most preferably prevent, the chance of unpasteurized fluid being passed into the treated water reservoir 148.

The flow control assembly 140 may comprise at least one thermostatic flow control valve 160 disposed between the elongated flow element 138 and the return line 142. Each thermostatic flow control valve 160 may comprise an operation temperature and a flow rate (i.e., the flow rate being dependent on the pressure in the system and the valve opening size). The thermostatic flow control valve 160 may be biased in a closed position. In the closed position, fluid may be prevented from passing from the elongated flow element 150 to the return line 142 through the thermostatic flow control valve 160. When the temperature of the fluid meets or exceeds the operating temperature of the thermostatic flow control valve 160, the valve 160 may open to allow fluid to pass through the valve 160. In some embodiments, the valve 160 may begin to open at the operating temperature and may continue to open further as temperatures increase. When the valve 160 is open fully, fluid may flow through or passed the valve 160 at the valve flow rate from the elongated flow element 150 through the thermostatic flow control valve 160 to the return line 142 and ultimately into the treated water reservoir 148.

Use of a single thermostatic flow control valve may, in some embodiments, create a risk of introducing unpasteurized fluid into the treated water reservoir 148. That is, when a thermostatic valve opens, water that has been heated in the elongated flow element 150 passes through the valve and, as such, water in the elongated flow element 150 continues to flow and spend less time in the elongated flow element 150. The flowing water may have a reduced temperature than the water or fluid initially providing the operating temperature because of the lesser amount of time the now flowing fluid spent in the elongated flow element 150. As the valve is exposed to the cooler water, the valve may begin to close or fully close. However, the reaction time of the valve in conjunction with the flow rate of the water may be such that unpasteurized water passes through the thermostatic valve before it can close. This type of pulsed flow for a single thermostatic valve may provide risk of contaminating the downstream aspects of the system and the treated water.

In order to provide a system with flexibility to accommodate several flow rates and temperatures while lowering the risk that untreated fluid will escape through the system, some embodiments may include a plurality of thermostatic valves 160. The plurality of thermostatic control valves 160 may include different operation temperatures and may also have differing flow rates. This arrangement may include valves that have operating temperatures that are lower having lower flow rates while valves that have higher operating temperatures may have higher flow rates. The several valves acting in concert may reduce the risk of unpasteurized fluid passing through the control valve assembly 140 and contaminating the downstream elements and the treated water reservoir 148.

FIG. 14 shows a schematic view of one embodiment of flow control assembly 140. The flow control assembly of FIG. 14 comprises a plurality of flow control valves 160, an inlet 162 at a first end of the flow control assembly 140, and an outlet 164 at a second end of the flow control assembly 140. In at least one embodiment, as shown in FIG. 14, the flow control assembly 140 comprises five flow control valves 160, although any number of suitable valves for the assembly may be used. The number of valves 160 may depend on the average or median flow rate of the system, the solar heating rate, and the range of pasteurization temperatures. Each flow control valve 160 may have an operation temperature and a flow rate, and in at least one embodiment the operation temperature may differ from at least one other flow control valve 160 in the assembly 140. Each flow control valve 160 may be biased in the closed position. In some embodiments, as shown, the flow control valves 160 may be disposed relative to one another in a parallel configuration. In other embodiments, at least one flow control valve 160 may be disposed relative to another flow control valve in a series configuration. The inlet 162 may be in fluid communication with the elongated flow element 150, and the outlet 164 may be in fluid communication with the return line 142. Fluid may enter the flow control assembly 140 from the inlet 162. Based on the temperature of the fluid, one or more of the flow control valves 160 may open based on their respective operating temperatures, and the fluid may pass through the outlet 164. If the fluid entering the flow control assembly 140 is below the operating temperature of all of the flow control valves 160, all of the control valves 160 may remain closed such that fluid does not pass through the outlet 164. The plurality of valves 160 and the operating temperature of each may be selected to ensure that the temperatures experienced by the fluid as it passes through the elongated flow element 150 and the time it remains at those temperatures is sufficient to pasteurize the fluid. A model relating to inactivation of pathogens and the temperatures and times created by the present system is discussed below. This system may allow for the flow of the fluid in the system to be relatively constant over time and reduce or even eliminate pulsed flow.

FIG. 15 shows an exploded view of one embodiment of a flow control assembly 140. FIG. 16 shows a cross-sectional view thereof. The flow control assembly 140 of FIGS. 15-16 may include a housing which may comprise a face 168 and a body 170 defining a chamber 172 and one or more flow channels 174. The assembly may also include a plurality of flow control valves 160 disposed at least partially within the chamber 172. In some embodiments, as shown, the flow control assembly 140 may further comprise a degassing valve 176 for releasing any excess fluid pressure that may build up within the assembly. In some embodiments, as shown, the flow control assembly 140 may further comprise flush ports within the body 140 for cleaning any contamination within the chamber 172 or the flow channels 174 and plugs that seal the flush ports. As shown in the embodiment of FIG. 15, the flow control assembly 140 may include three flow control valves 160 disposed within the body 170 of the housing. However, any number of suitable valves for the assembly may be used. The three flow control valves 160 may be arranged in parallel within the housing 170. The housing may protect the flow control valves 160 from the elements. In addition to protecting the flow control valves 160, the housing may provide insulation so as to prevent or reduce heat loss from the fluid within the flow assembly 140. In at least the embodiment shown, the face 168 may be removably connected to the body 170. In some embodiments, the face 168 of the housing mates directly with the fluid heating element 138. In at least the embodiment shown, the face 168 may include a first opening defining the inlet 162, and the face 168 may include a second opening defining the outlet 164. The inlet 162 may provide fluid communication between the chamber 172 and the elongated flow element 150, and the outlet 164 may provide fluid communication between the one or more flow channels 174 and the return line 142. In at least one embodiment, the housing may include a pressure drop hole for each flow control valve 160 where the position and size of the pressure drop hole may be dependent upon the temperature setting of the flow control valve 160.

In some embodiments, the flow control valves 160 may comprise thermostatic control valves 160 or other mechanically actuated flow control valves 160. In at least the embodiment shown in FIGS. 15-16, each flow control valve 160 comprises a thermostatic element 178, a valve tube 180, a valve plunger 182, and a spring 184. In at least one embodiment, the thermostatic element 178 is disposed within the chamber 172 and mechanically connected to the plunger 182, and the valve plunger 182 is disposed within the valve tube 180. The thermostatic element 178 may have an operating temperature, and the thermostatic element 178 may be activated when the thermostatic element 178 comes into contact with fluid in the chamber 172 that meets or exceeds the operating temperature. The valve tube 180 and the valve plunger 182 work together to thermally actuate and allow fluid passage when a fluid reaches the operating temperature of the valve 178. In at least one embodiment, the plunger 182 has an indentation which moves in a first direction as the respective thermostatic element 178 warms and in a second direction as the respective thermostatic element 178 cools. The spring 184 biases the valve plunger 182 into a closed position. In at least one embodiment the valve tube 180 has a hole disposed within the sidewall of the valve tube, the hole being in fluid communication with the flow channel 174. When the indentation of the plunger 182 is aligned with the hole on the valve tube sidewall, fluid passes from the chamber 172 into through the flow channel and passed the valve to the outlet 164. When the plunger 182 is positioned so that the indentation is not aligned with the hole, fluid cannot pass from the chamber 172 into the flow channel 174. In some embodiments, as the valve plunger 182 moves in either the first direction or the second direction, a portion of the hole may be aligned with the indentation of the plunger 182 such that flow is restricted.

Each flow control valve 160 may have its own operating temperature and flow rate. In a preferred embodiment, the operating temperature for all flow control valves 160 within the flow control assembly is below the boiling point of the fluid (e.g. for water, 100 degrees C.). In one embodiment, the flow control valves 160 may all have the same operating temperature setting such that when the fluid reaches that temperature the valves are open, which may result in a pulsed flow of the fluid. In a preferred embodiment, the operating temperature and/or flow rate for each flow control valve 160 differs from at least one other flow control valve 160 in the assembly. This may provide for more stable flow of the fluid within the system as opposed to a pulsed flow. In at least one embodiment, a first control valve 160 may have a first operating temperature. The first control valve 160 may also have a first flow rate. The first control valve 160 may be biased in the closed position. A second control valve 160 may have a second operating temperature greater than the first operating temperature of the first control valve 160. In some embodiment, the second control valve 160 may also have a second flow rate greater than or different from the first flow rate. In embodiments having a third control valve 160, the third control valve 160 may have a third operating temperature greater than the second operating temperature of the second temperature control valve 160 and greater than the first operating temperature of the first temperature control valve 160. In at least one embodiment, the third operating temperature may be below the boiling point of the fluid (e.g. for water 100 degrees C.). In some embodiments, the third control valve 160 may have a third flow rate greater than or different from the second flow rate and greater than or different from the first flow rate. The flow rates through the system may be dictated by the valve settings and the supplied pressure (or height of the fluid supply tank). For residential applications with roof-top water vessels, for example, and high incident solar energy, the flow rates may be approximately one gallon per minute, for example, or more. In some embodiments, the operating temperatures of the control valves may include 78 degrees C., 85 degrees C., and 90 degrees C. In still other embodiments, the operating temperatures of the control valves may include 50 degrees C., 55 degrees C., and 60 degrees C. In still other embodiments, the operating temperatures of the control valves may include 60 degrees C., 70 degrees C., and 80 degrees C. As may be appreciated, the higher temperature settings of the control valves may reduce the flow rate of the system overall, but may increase the treatment temperature. The model discussed below with knowledge of the pathogens that are present may be used to select suitable operating temperatures for the valves so as to ensure suitable treatment and to also give consideration to efficient use of the solar energy by providing relatively fast flow rates.

In at least one embodiment, the flow control valves 160 may be arranged to act additively. That is, when a first control valve 160 opens and then a second one opens, the flow rate of the first valve 160 may be supplemented by the second valve 160 such that the flow rate increases based on the additional flow allowed by the second valve 160. In some embodiments, when the temperature of the fluid reaches the first operating temperature, the first control valve 160 may open to allow fluid to pass through the chamber 172 to the flow channel 174 at the first flow rate. When the temperature of the fluid reaches the operating temperature of the second control valve 160, the second control valve 160 may open to allow fluid to pass through the chamber 172 to the flow channel 174 at a second flow rate. With fluid flowing through both the of the first and second valves 160, the resulting flow to the return tube 142 may be a combination of the flow rate of the first and second valves 160. Where the system has at least three control valves 160, when the temperature of the fluid reaches the operating temperature of the third control valve 160, the third control valve 160 may open to allow fluid to pass through the chamber 172 to the flow channel 174 at the third flow rate. As the temperature of the fluid declines below the third operating temperature, the third valve 160 may close and less fluid may be allowed to flow. As the temperature of the fluid further declines below the second operating temperature, the second valve 160 may close and less fluid may be allowed to flow. If however, the temperature falls below a threshold temperature, all of the control valves 160 may then return to their biased closed position.

In still other embodiments, the distance between the temperature chamber 172 and the flow control portion of the valve 160 may be determined in an effort to protect against untreated water flowing through the system. That is, this distance may be selected together with flow rates and valve closing times such that when temperatures drop below the operating temperature of a given valve 160, the valve 160 has sufficient time to close before fluid or water below the operating temperature reaches the flow control.

As mentioned, the flow control assembly 140 may also include a degassing valve 176. As shown in FIG. 16, the degassing valve 176 may be arranged within the flow control assembly 140 at an upper location where gases in the system will work their way to the valve location. The degassing valve 176 may be configured to purge air, steam, or other gas in the system on startup, when there is an intermittent water source, and as gas develops within the system such as when water vapor builds up during boiling, for example. As shown, the degassing valve 176 may be arranged on the control valve 160 assembly, for example.

Figure 18C:
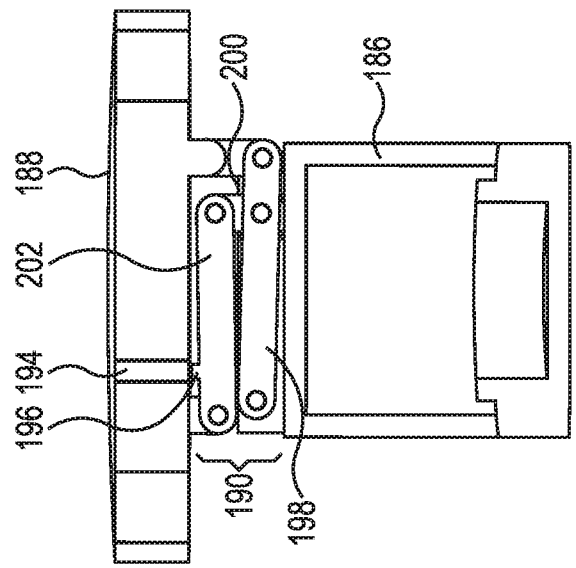
FIG. 18C is a cross-sectional view thereof, according to one or more embodiments.
Figure 18B:
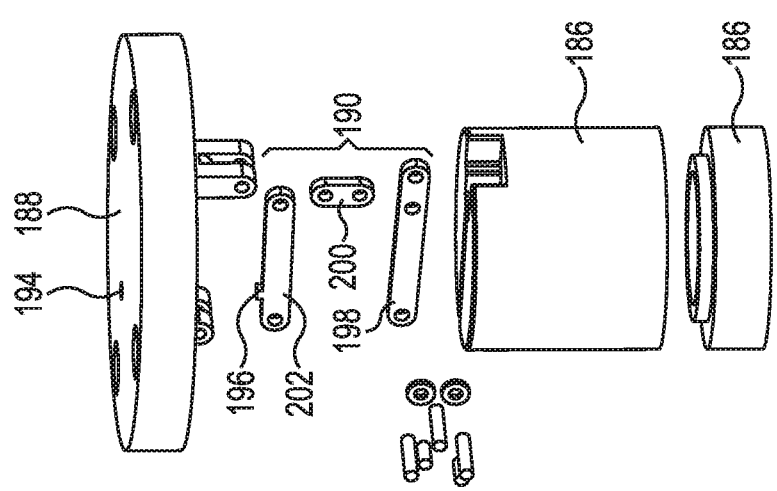
FIG. 18B is an exploded view thereof, according to one or more embodiments.
Figure 18A:
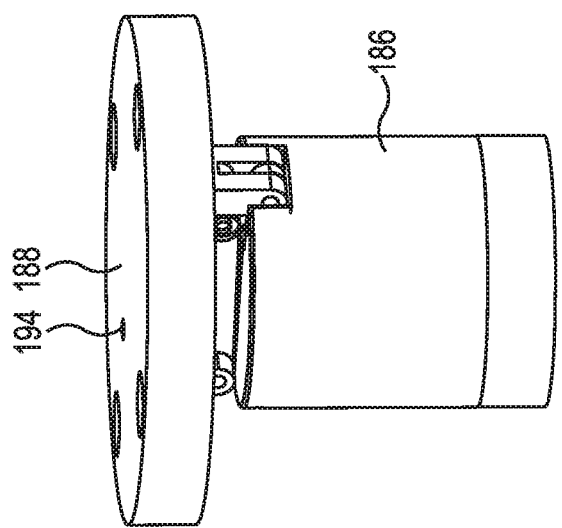
FIG. 18A is a perspective view of a degassing valve, according to one or more embodiments.

As shown in more detail in FIGS. 18A-18C, the degassing valve 176 may include a float 186, a cap 188, and a linkage 190. The cap 188 may be a relatively rigid element configured for sealingly securing to the fluid control assembly 140 over an opening. That is the control valve assembly 140 may have an opening on its surface that is in fluid communication with the fluid pathway extending through the control valve assembly 140. The opening in the control valve assembly 140 may be arranged substantially near the top of the assembly 140 in a position where gases may naturally propagate, for example. The cap 188 of the degassing valve 176 may be configured to be secured over the opening in a sealed fashion to prevent leakage of fluid from the control valve assembly 140. When the cap 188 is secured over the opening, a chamber 192 may be defined in the control valve assembly 140 over which the cap 188 is arranged. The cap 188 may include an orifice 194 for allowing the release of gases from the system.

The float 186 of the degassing valve 176 may be configured for arrangement in the chamber 192 formed by the control valve assembly 140 188 and the cap 188. The float 186 may be sized and shaped such that it may move substantially freely upward and downward within the chamber 192 below the cap 188. In some embodiments, the float 186 may be shaped like a piston, for example, and may be substantially cylindrical. The float 186 may be a two piece assembly as shown having a main body portion and a base portion or the float 186 may be a single piece float 186. The float 186 may be constructed of substantially light-weight material and when assembled with the internal cavity shown, may have a weight and volume that provide for a density less than water so that it floats when water or other fluid is present in the chamber 192.

Figure 17:
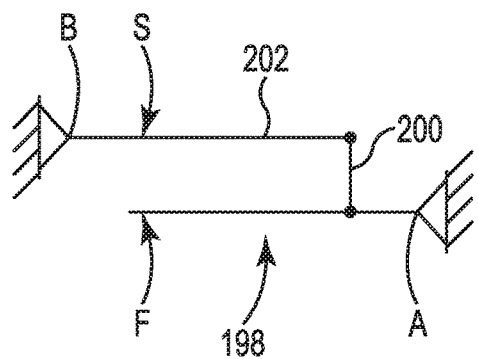
FIG. 17 is a free-body diagram of a linkage of a degassing valve, according to one or more embodiments.

The float 186 may be operable relative to the cap 188 by way of a linkage 190. As shown, a linkage 190 may be provided that secures the float 186 to the cap 188 and articulates between the float 186 and the cap 188 as the float 186 moves upward and downward in the chamber 192. It is to be appreciated that when water is present in the chamber 192, the float 186 will rise in the water causing the float 186 to move upward in the chamber 192. As shown in FIGS. 18B and 18C, the linkage 190 may include a seal 196 for sealing the orifice 194 in the cap 188 when the float 186 is moved to an upper position in the chamber 192 and relative to the cap 188. The present linkage 190 may provide a particularly strong sealing force on the cap orifice 194 due to the linkage arrangement. That is, as shown in FIGS. 18B and 18C, when the float 186 is in the upper most position in the chamber 192, further upward motion of the float 186 may be resisted by the sealing stopper 196 over the orifice. That is, when the float 186 is in the upper most position, the linkage 190 is in a fixed position forming a statically determinate structure. As shown in the free-body diagram of FIG. 17, the force on the end of the bottom linkage member 198 from the float 186 may create a compressive force in the strut 200. The compressive force in the strut 200, may be higher than the float force because the strut 200 is positioned along the bottom linkage 198 at a position closer to the pivot point A than the float connection. For example, the strut force may be approximately 4 times the upward force from the float. The strut 200 may push upwardly on the upper linkage 202, which may be resisted by the seal 196 being seated over the orifice 194. Once again, because the sealing stopper 196 is positioned along the upper linkage 202 at a position closer to the pivot point B than the strut force, the force applied at the sealing stopper 196 may be much higher than the strut force. For example, the force applied at the sealing stopper 196 may be approximately 4 or 5 times the strut force. Accordingly, the sealing force 196 in the degassing valve 176 may be approximately 16 to 20 times the force of the float 186. This type of linkage 190 may allow for a relatively small float 186 and/or a relatively high sealing force from the float 186.

Referring back to FIGS. 10 and 11, a return line 142 is shown. The return line 142 may be in fluid communication with the flow control assembly 140 and may redirect water or fluid back to the preheat heat exchanger 144. In some embodiments, the return line 142 may extend through the housing 152 of the fluid heating element 138 as shown and to take advantage of the insulating properties of the housing 152. In other embodiments an alternative route may be provided and alternative insulation may be provided. It is to be appreciated that the fluid exiting the flow control assembly 140 may be at relative and/or extremely high temperatures. As such, the return line 142 may be constructed from relatively heat resistant material such as metal, ceramic, composite materials, or high temperature plastic. Still other material may be used. In some embodiments, the return line 142 may be a tube, pipe, or other lumen-type element. In some other embodiments the return line 142 may lead to the housing 152 and terminate at a lumen formed in the housing 152 such that the lumen in the housing may carry the fluid to the preheat heat exchanger 144.

It is to be appreciated that where a heat exchanger is not being used (i.e., in the condition of water heating) the return line 142 may lead directly to the treated water or fluid reservoir 148 or to a point of use rather than returning to the preheat heat exchanger 144. That is, where the system is implemented in a situation where the fluid is being heated to produce hot water as opposed to being used to pasteurize water, the step of preheating of the water may be omitted because the heat exchange operation sacrifices heat from the outflowing fluid.

Figure 19A:
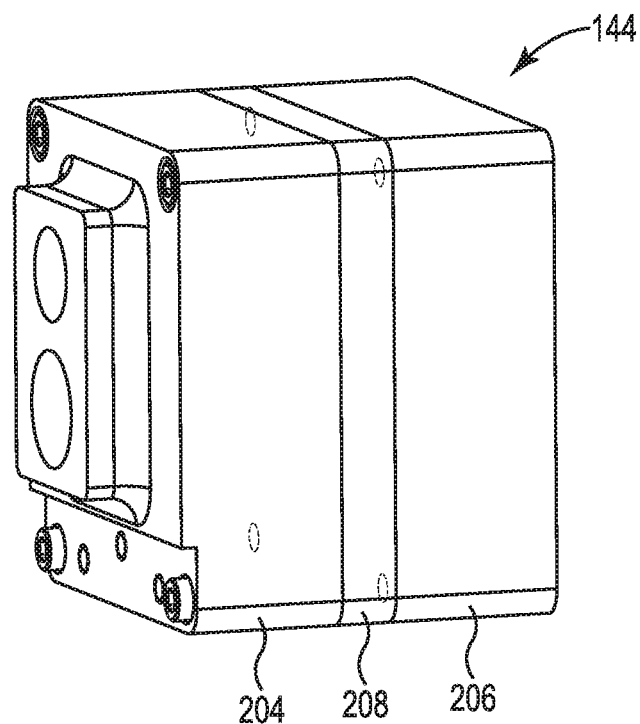
FIG. 19A is a perspective view of a heat exchanger, according to one or more embodiments.
Figure 19B:
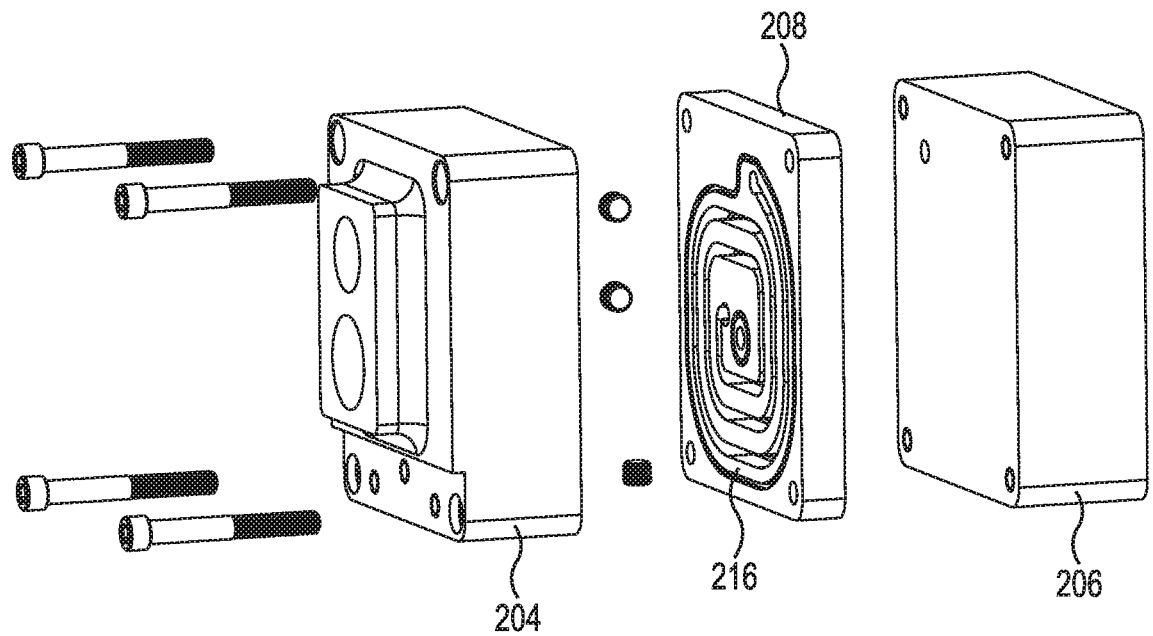
FIG. 19B is an exploded view thereof, according to one or more embodiments.

Turning now to FIGS. 19A and 19B, the return line 142 may return the water or fluid to the preheat heat exchanger 144. As shown, the preheat heat exchanger 144 may receive water or other fluid from the feed line 136 as well as water or fluid from the return line 142. The preheat heat exchanger 144 may be configured to provide thermal communication between these two fluids such that heat from the return line fluid may be used to increase the temperature in the feed line fluid. In the case of a water pasteurization process, once the water is pasteurized, the heat in the water may no longer be useful or helpful and, as such, it can be used to increase the temperature in the incoming water to give it a sort of head start on heating by utilizing otherwise wasted energy. That is, were the water in the return line 142 simply directed toward the treated water reservoir 148, such water would be placed in the reservoir 148 at an extremely high temperature only to sit in the treated fluid reservoir 148 and have the heat dissipate wastefully. Moreover, the effluent line 146 may be extremely hot if the treated fluid is not passed through the heat exchanger 144.

The heat exchanger 144 may include a front 204, back 206, and middle body 208. The front 204 and back 206 bodies may be configured to sandwich the middle body 208 between them and maintain a substantially constant and even sealing pressure on the middle body 208. The middle body 208 may be configured to receive the return line fluid and the feed line fluid and thermally expose them to one another to transfer the heat from the return line fluid to the feed line fluid.

The front and back bodies 204, 206 may be substantially block-like elements with a relatively large amount of mass. For example, in some embodiments, the front and back bodies 204, 206 may be substantially thick relative to the middle body 208. The front and back bodies 204, 206 may be substantially rectangular and may have a perimeter size and shape that is substantially the same or similar to the perimeter size and shape of the middle body 208. Accordingly, when the front and back bodies 206, 208 are assembled with the middle body 208, a block-like element having a thickness equal to the combined thicknesses of the several elements may be provided. In some embodiments, the plan view size of the front and back bodies 204, 206 may range from approximately 1 inch to approximately 12 inches, or from approximately 2 inches to approximately 8 inches or from approximately 4 inches to approximately 6 inches. The thickness of the front and back bodies 204, 206 may range from approximately ½ inch to approximately 4 inches or from approximately ¾ inch to approximately 2 inches or from approximately ¾ inch to approximately 1¼ inches.

The middle body 208 may include a substantially plate-like element configured for being sandwiched between the front and back bodies 204, 206. The middle body 208 may have formed in each face a fluid pathway 216 for routing fluid in a relatively or substantially tortuous pathway. In some embodiments, as shown, the fluid pathway 216 may include a round and/or spiral type of pathway. It is to be appreciated that the pathways on each face may be mirror images of one another such that fluid flowing through each of the pathways is substantially adjacent to the fluid on the opposing side of the middle body 208 and separated only by the thickness remaining between the formed pathways 216. In some embodiments, the thickness between fluid pathways 216 on each side of the middle body 208 may range from approximately 28 gauge to approximately ¼ inch or from approximately 21 gauge to approximately 1/16 inch or from approximately 17 gauge to approximately 19 gauge. Still other thicknesses may be provided and selected to reduce the thickness as much as possible while accommodating reasonable fabrication tolerances and considering effects of wear, corrosion, or other effects that may create holes or perforations in the thin wall. While a spiral pathway is shown, it is to be appreciated that several other pathways may be used such as a zigzag, switchback, or other arrangement. The pathway 216 may be effective to provide for a long length in a small amount of space so as to increase the amount of time that the two flowing fluids are thermally exposed to one another. Moreover, the tortuous path may have a relatively high fluid mixing effect such that each of the fluids on either side of the middle body 208 continually mix with themselves, thus allowing for a better distribution of heat within each fluid and, thus, better thermal exchange through the middle body. In some embodiments, the fluid on either side of the middle body 208 may be configured to flow in the same direction as the fluid on the other side or the fluid may flow opposite directions as compared to the fluid on the other side.

The front 204, back 206, and middle bodies 208 may be constructed from the same or different materials. In some embodiments, the front, back and middle bodies 204, 206, 208 may be constructed from a same or similar conductive material. In other embodiments, the front and back bodies 204, 206 may include substantially insulating materials so as to avoid dissipation of heat from the system. In contrast, the middle body 208 may be made from relatively or highly conductive material so as to conduct heat from the return line fluid and transfer the heat to the feed line fluid. In some embodiments, for example, the front and back bodies 204, 206 may include a ceramic or other insulating material and the middle body 208 may include a metal such as steel or other conductive material. In some embodiments, the middle body 208 may also include an insulating perimeter to resist heat loss out the sides of the middle body 208.

It is to be appreciated that while the heat exchanger 144 has been described as having three parts, manufacturing techniques may be used to manufacture the heat exchanger 144 as a single part. For example, injection molding or additive manufacturing such as 3D printing may allow for the heat exchanger 144 to be formed as a single piece. Still other manufacturing methods and approaches may be used.

Turning back now to FIG. 9, an effluent line 146 is shown. The effluent line 146 may be in fluid communication with the preheat heat exchanger 144 and the treated fluid collection reservoir 148. The effluent line 146 may be tapped into the collection reservoir 148 at or near the top, for example. Like the feed line 136, the effluent line 146 may be a polypropylene, polyethylene, or other polymeric material or another material may be used. The effluent line 146 may be sized to accommodate the flow of fluid from the system without overly constraining flow and, as such, the effluent line 146 may have a diameter and/or cross-sectional flow area reasonably similar to the diameter or cross-sectional flow area of the fluid heating element 138. In some embodiments, the effluent line 146 may be a ½ inch, ¾ inch, 1 inch, 1½ inch, 2 inch, or 3 inch line, for example. In still other embodiments, other size effluent lines may be used.

The treated fluid collection reservoir 148 may be a closed sanitary tank configured to remain in a sanitary condition so as to avoid contamination of the treated and/or pasteurized water or fluid. In some embodiments, for example, the treated water reservoir 148 may be a stainless steel tank, a coated steel tank, a polyethylene, polypropylene, or other polymeric material. The treated fluid collection reservoir 148 may be sized based on the output of the system and may be sized based on one or more systems where more than one system is directing treated fluid to the tank. The treated fluid collection reservoir 148 may include a pressure relief valve equalizing pressures within the tank and/or a breathing mechanism that allows air transfer, but resists and/or prevents entry of contaminants or pollutants, for example.

The treated fluid collection reservoir 148 may be in fluid communication with a potable water distribution or supply system such that the potable water may be used for drinking, cooking, or other purposes. In some embodiments, the collection reservoir 148 may include a spigot or other distribution mechanism such that potable water may be access or retrieved directly from the reservoir. Still other types of water retrieval systems or devices may be provided.

Support Structure and Tracking System

Figure 20:
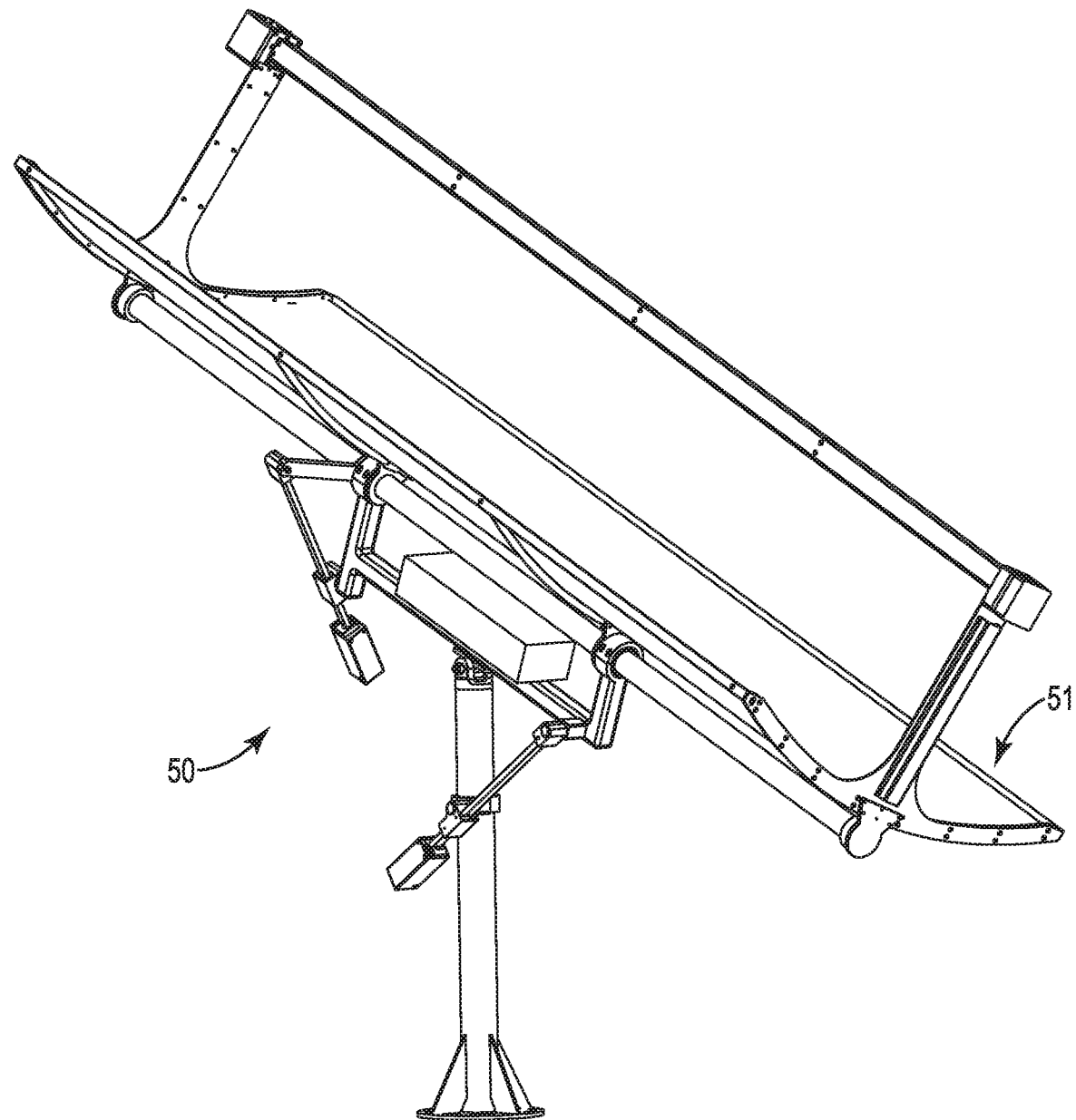
FIG. 20 is a perspective view of a tracking device and payload, according to one or more embodiments.

Turning now to FIG. 20, a dual axis tracking device 50 is shown. The tracking device 50 may generally be configured to track the location of an object in space, such as the sun, such that the device may direct a payload 51, such as solar panels, toward the object or at an angle relative to the object. The tracking device 50 may track the location of the object over the course of a day or night, for example, as the object moves across the sky, such that the device may substantially continuously direct its payload 51 at the appropriate angle.

Figure 21:
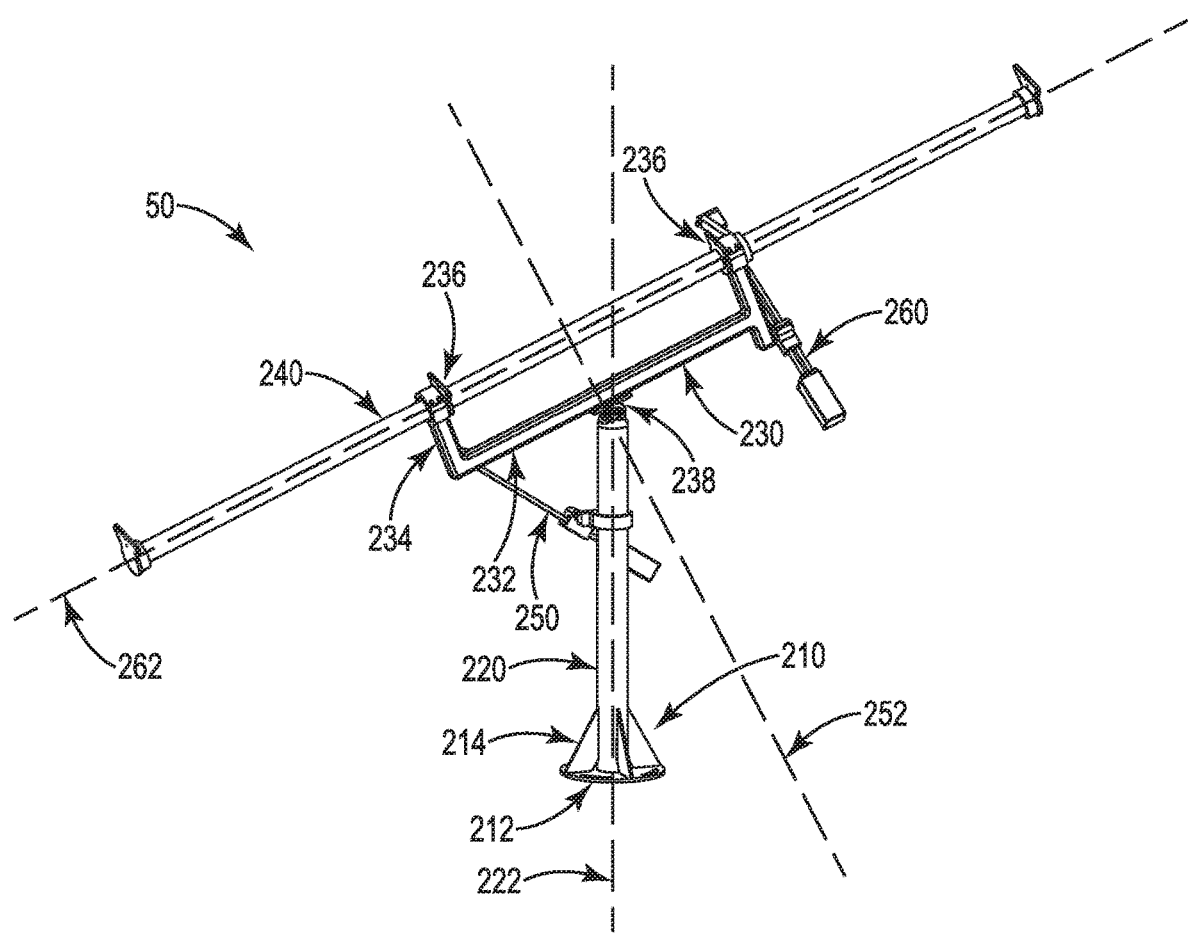
FIG. 21 is a perspective view of the tracking device of FIG. 20, according to one or more embodiments.

FIG. 21 illustrates the tracking device 50 that may support and direct the payload 51. The tracking device 50 may have a base 210, an upright portion 220, an arm portion 230, a spine portion 240, a first actuation assembly 250, and a second actuation assembly 260.

The upright portion 220 may generally support the weight of the tracking device 50 and any payload 51 the device may be carrying such as solar panels. The upright portion 220 may support the tracking device 50 high enough off of the ground surface so as to allow for a full range of movement of the payload 51 by the first 250 and second 260 actuation assemblies. In some embodiments, the upright portion 220 may generally be constructed of steel, aluminum, or other metals or metal alloys. In other embodiments, the upright portion 220 may be constructed of one or more plastics such as PVC, concrete, or any other suitable material. The upright portion 220 may generally have any suitable length. The upright portion 220 may have a rounded cross section as shown in FIG. 21, in some embodiments. In other embodiments, the upright portion 220 may have any suitable cross sectional shape. The upright portion 220 may have any suitable width or diameter. The upright portion 220 may connect with or to the ground surface via a base 210.

With continued reference to FIG. 21, the base 210 may provide lateral support for the upright portion 220. The base 210 may include a foot 212 and one or more angular supports 214. In some embodiments, the tracking device 50 may be positioned on the ground surface. In other embodiments, the tracking device 50 may be positioned on a foundation, such as a concrete foundation, or other surface. The foot 212 may be positioned between the upright portion 220 and ground surface, foundation, or other surface. The foot 212 may have a width or diameter that is larger than that of the upright portion 220, so as to provide lateral support to the upright portion. In some embodiments, the foot 212 may be bolted or otherwise coupled to the ground, foundation, or other surface. In other embodiments, the foot 212 may be positioned on the ground, foundation, or other surface without a coupling mechanism. Where the foot 212 is not bolted or otherwise coupled to the ground, foundation, or other surface, the foot may have a relatively large width or diameter, compared to the upright portion 220. However, where the foot 212 is bolted or otherwise coupled to the ground, foundation, or other surface, the foot may have a relatively smaller width or diameter, in some embodiments. In other embodiments, the foot 212 may have any suitable width or diameter. As shown in FIG. 21, in some embodiments, the foot 212 may have a circular shape. In other embodiments, the foot 212 may have any suitable shape. The foot 212 may generally have any suitable thickness. One or more angular supports 214 may strengthen the connection between the foot 212 and the upright portion 220. The one or more angular supports 214 may have any suitable thickness. In some embodiments, the base 220 may be constructed of steel, aluminum, or other metals or metal alloys. In other embodiments, the base 220 may be constructed of one or more plastics such as PVC, concrete, or any other suitable material.

With continued reference to FIG. 21, an arm portion 230 may couple to the upright portion 220 to provide rotational support to the spine portion 240. The arm portion 230 may have a lateral member 232 and one or more connector arms 234. In some embodiments, the lateral member 232 may be positioned parallel to the spine portion 240. In some embodiments, the lateral member 232 may have a length that is longer, shorter, or the same as the length of the spine portion 240. Generally, the lateral member 232 may have a length sufficient to provide enough support for the length of the spine portion 240, and the length of the lateral member may thus be proportion to the length of the spine portion. The one or more connector arms 234 may extend perpendicular from the lateral member 232 to connect to the spine portion 240. In some embodiments, as shown in FIG. 21, the arm portion 230 may have one connector arm 234 at each end of the lateral member 232. In other embodiments, the arm portion 230 may have any suitable number of connector arms 234. Each connector arm 234 may couple to the spine portion 240 via a connector 236. The connector 236 may be or include a clamp, bolts, screws, or any suitable coupling mechanism. In some embodiments, the connector 236 may allow the spine portion 240 to rotate or twist. In some embodiments, the spine portion 240 may connect directly to the lateral member 232. For example, in some embodiments, the spine portion 240 may pass through an opening in the lateral member 232. The lateral member 232 and connector arms 234 may have any suitable cross sectional shape, such as a rectangular shape for example. The arm portion 230 may be constructed of steel, aluminum, or other metals or metal alloys. In other embodiments, the arm portion 230 may be constructed of one or more plastics such as PVC, or any other suitable material.

In some embodiments, the arm portion 230 may couple to the upright portion 220 by a single axis support 238. The single axis support 238 may comprise a pivoted connection and may provide for rotational movement about one or more axes, and in some cases two axes. In some embodiments, the single axis support 238 may allow for the arm portion 230 to rotate about a first axis of rotation 252, which may be perpendicular to a longitudinal axis of the lateral member 232, and a second axis of rotation 262 orthogonal to the first axis. The first and second axes of rotation 252, 262 may each pass through the connection point between the arm portion 230 and the upright portion 220. In some embodiments, the spine portion 240 may connect directly to the upright portion 230 via the single axis support 238.

With continued reference to FIG. 21, the spine portion 240 may provide support and/or alignment for a payload 51 held by the tracking device 50. For example, the device may carry one or more solar panels, in which the spine portion 240 may provide a base for supporting and/or aligning the one or more solar panels. In this way, as the object is tracked across the sky, the spine portion 240 may serve to align the payload 51 with the object or with a point relative to the object. The spine portion 240 may be any suitable length and width or diameter so as to provide sufficient support to the payload 51. The spine portion 240 may have any suitable cross sectional shape, such as a circular shape for example. The spine portion 240 may be constructed of steel, aluminum, or other metals or metal alloys. In other embodiments, the spine portion 240 may be constructed of one or more plastics such as PVC, or any other suitable material.

With continued reference to FIG. 21, the tracking device 50 may have one or more actuation assemblies that facilitate movement of the device. Generally, one or more actuation assemblies may facilitate movement of the arm portion 230, spine portion 240, and/or payload 51 with respect to the upright portion 220 and base 210. In some embodiments, the tracking device 50 may have a first actuation assembly 250 and a second actuation assembly 260.

The first actuation assembly 250 may, in some embodiments, be positioned between the upright portion 220 and the arm portion 230. In other embodiments, the first actuation assembly 250 may be positioned between the spine portion 240 and the upright portion 220, or between the arm portion 230 and spine portion 240, for example. Other positioning arrangements of the first actuation assembly 250 are contemplated as well. The first actuation assembly 250 may facilitate movement of the arm portion 230, spine portion 240, and/or payload 51 with respect to the upright portion 220 and base 210 about a horizontal axis. The first actuation assembly 250 may couple to the upright portion 220 and arm portion 230 using clamps, bolts, screws, or any suitable coupling mechanism. In some embodiments, the first actuation assembly 250 may couple to the upright portion 220 and/or arm portion 230 with a pivoted, hinged, or other movable connection.

In some embodiments, the second actuation assembly 260 may be positioned between the arm portion 230 and the spine portion 240. In other embodiments, the second actuation assembly 260 may be positioned between the arm portion 230 and the upright portion 220, or between the spine portion 240 and the upright portion 220, for example. Other positioning arrangements of the second actuation assembly 260 is contemplated as well. The second actuation assembly 260 may facilitate movement of the arm portion 230, spine portion 240, and/or payload 51 with respect to the upright portion 220 and base 210 about the longitudinal axis of the spine. The second actuation assembly 260 may couple to the upright arm portion 230 and spine portion 240 using clamps, bolts, screws, or any suitable coupling mechanism. In some embodiments, the second actuation assembly 260 may couple to the arm portion 230 and/or spine portion 240 with a pivoted, hinged, or other movable connection.

Using the first and second actuation assemblies 250, 260, the tracking device 50 may operate to position the spine portion 240 to direct a payload 51 toward or relative to a moving object, such as the sun. In this regard, the first actuation assembly 250 may provide for movement of the arm portion 230, spine portion 240, and/or payload 51 about a first axis of rotation 252, as shown in FIG. 21. The first axis of rotation 252 may be perpendicular to a longitudinal axis of the spine portion 240 and may be generally horizontal. Additionally, in some embodiments, the second actuation assembly 260 may provide for movement of the payload 51 about a second axis of rotation 262, which may be the longitudinal axis of the spine. The two axes of rotation 252, 262 may allow for the tracking device 50 to direct its payload 51 at a moving object across the sky, in some embodiments, while the longitudinal axis of the spine portion 240 remains statically pointed in a direction. That is, where a third axis 222 aligns with the upright portion 220, the longitudinal axis of the spine portion 240 may remain fixed with respect to rotation about the third axis. For example, where the longitudinal axis of the spine portion 240 is directed North and South, the third axis 222 and rotation about the third axis may be static such that the longitudinal axis of the spine portion may continuously point North and South while movement about the first and second axes 252, 262 occurs.

Figure 22A:
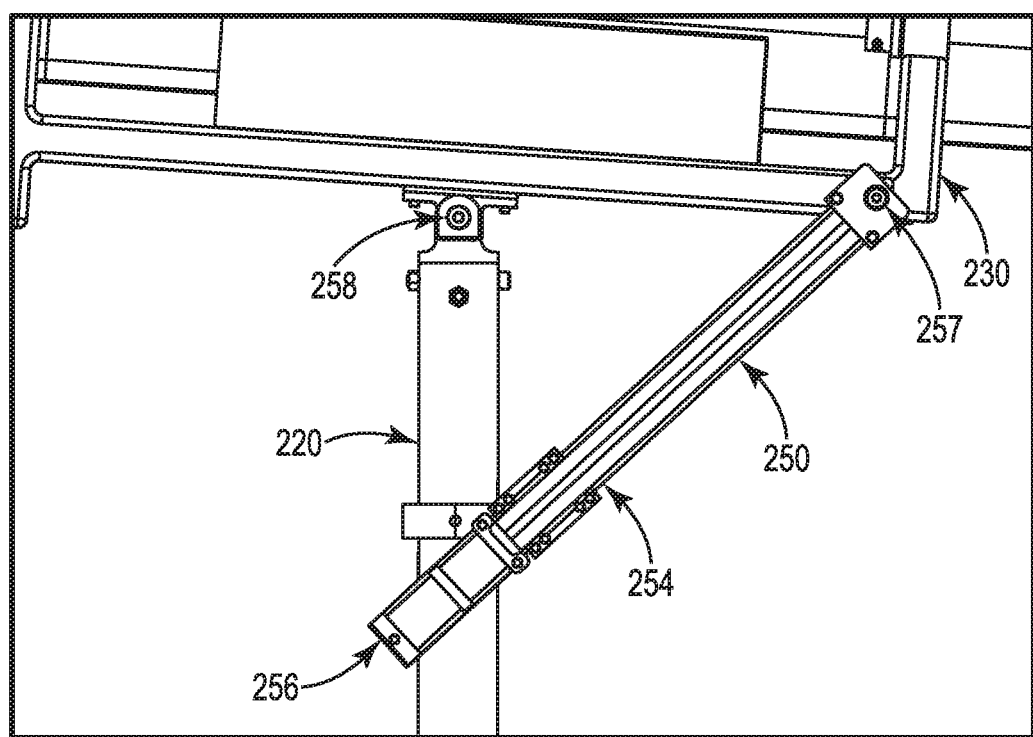
FIG. 22A is a detail view of a first actuation assembly, according to one or more embodiments.

FIG. 22A illustrates the first actuation assembly 250. The first actuation assembly 250 may rotate the arm portion 230, spine portion 240, and/or payload 51 about the first axis of rotation 252 with two pivot points 257, 258. The first pivot point 257 may be located where the first actuation assembly 250 couples to the arm portion 230. The second pivot point 258 may be located where the arm portion 230 connects to the upright portion 220 via the single axis support 238. The first actuation assembly may comprise a linear actuator 254, such as a linear slide, and a motor 256 that drives the linear actuator. A sliding element of the linear actuator 254 may couple to the upright portion 220 with a fixed connection. In this way, as the motor 256 drives movement along the linear actuator 254, the arm portion 230, spine portion 240, and/or payload 51 may pivot about the first and second pivot points 257, 258, and be rotated about the first axis of rotation 252. It may be appreciated that the orientation of the linear actuator 254 may be reversed in some embodiments, such that the sliding element may couple to the arm portion 230 and a pivot point may be located at the connection between the first actuation assembly 250 and the upright portion 220. The linear actuator 254 may have any suitable length and range of motion in various embodiments. In some embodiments, the length may depend on where along the arm portion 230 and upright portion 220 the first actuation assembly 250 connects, and may further depend on the range of motion provided about the first axis of rotation 252.

The motor 256 may be a relatively inexpensive motor in some embodiments. For example, the motor 256 may be a low cost stepper motor. In other embodiments, a DC motor or servo motor may be used. In other embodiments, the motor 256 may be any suitable motor. The motor 256 may rotate a gear screw or lead screw, for example, with each step. The gear screw or lead screw may operate to drive the sliding element along the linear actuator 254. In this way, the gear screw or lead screw may translate the rotational motion of the motor 256 into linear motion of the linear actuator 254. In some embodiments, the gear screw or lead screw may couple to a gearbox, which may operate to drive the sliding element along the linear actuator 254. The gearbox may provide for additional torque to the linear actuator 254 in some embodiments. A gearbox may include one or more gears arranged in any suitable configuration. In some embodiments, a planetary gearbox may be used. In other embodiments, any suitable gearbox may be used to assist with moving the sliding element along the linear actuator 254. In some embodiments, any suitable gear reduction of the gearbox may be used to increase the motor and gearbox output torque.

In some embodiments, the motor 256, linear actuator 254, and/or other components may be configured for use in harsh conditions or otherwise outdoor use. For example, mechanical components may be configured to operate without lubricating agents. In some embodiments, for example, the gear screw or lead screw may connect to the linear actuator 254 with a plastic bearing or other element that may function without lubrication, such as for example an IGUS DRYLIN bearing or other device to assist with movement. In some embodiments, the gear screw or lead screw or one or more other components may be constructed of a material such as that used in the IGUS DRYLIN devices. In other embodiments, similar materials or any suitable material may be used to provide for operation without lubricating agents.

Figure 22B:
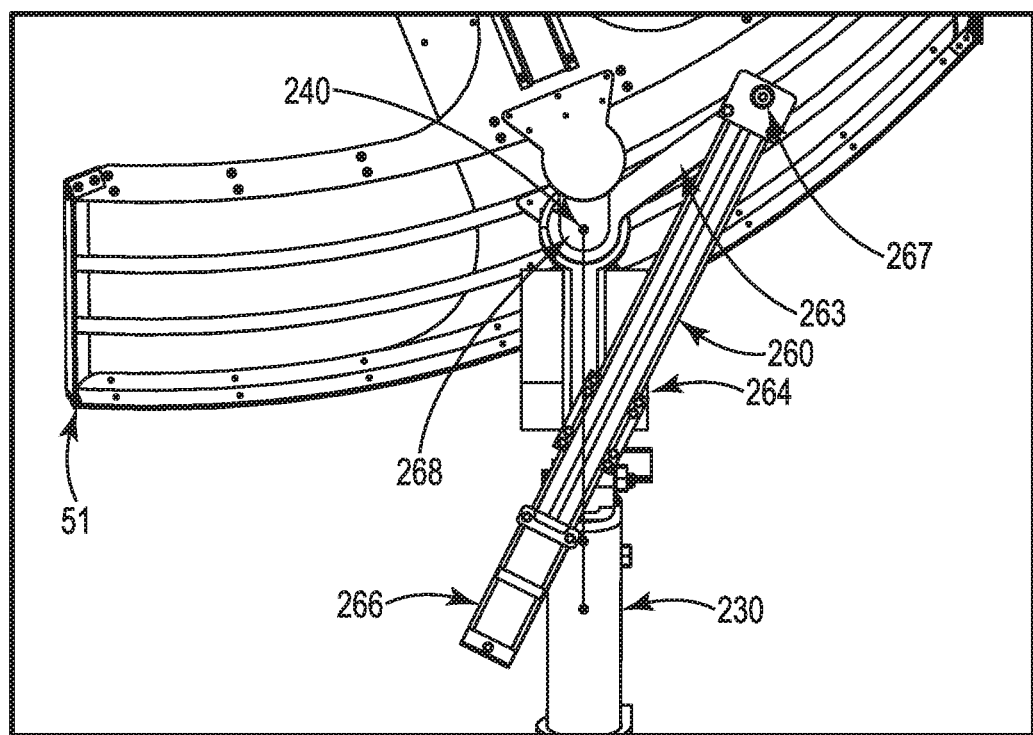
FIG. 22B is a detail view of a second actuation assembly, according to one or more embodiments.

FIG. 22B illustrates the second actuation assembly 260. The second actuation assembly 260 may twist the spine portion 240 so as to rotate the payload 51 about the second axis of rotation 262. Like the first actuation assembly 250, the second actuation assembly 260 may comprise a linear actuator 264 and a motor 266 that drives the linear actuator. The second actuation assembly 260 may further comprise a torque arm 263 in some embodiments. The torque arm may connect the linear actuator to the spine portion 240. The second actuation assembly may connect to the upright portion 220 with a fixed connection, in some embodiments. In this way, the second actuation assembly 260 may rotate the spine portion 240 and/or payload 51 about the second axis of rotation 262 with two pivot points 267, 268. The first pivot point 267 may be located where the second actuation assembly 260 couples to the torque arm 263. The second pivot point 268 may be located where the torque arm 263 couples to the spine portion 240. A sliding element of the linear actuator 264 may couple to the upright portion 220 with a fixed connection. In this way, as the motor 266 drives movement along the linear actuator 264, the spine portion 240 and/or payload 51 may pivot about the first and second pivot points 267, 268, and be rotated about the second axis of rotation 262. It may be appreciated that the orientation of the linear actuator 264 may be reversed in some embodiments, such that the sliding element may couple to the spine portion 240 and a pivot point may be located at the connection between the second actuation assembly 260 and the upright portion 220. The linear actuator 264 may have any suitable length and range of motion in various embodiments. In some embodiments, the length may depend on where along the spine portion 240 and upright portion 220 the second actuation assembly 260 connects, and may further depend on the range of motion provided about the second axis of rotation 262.

Like motor 256 of the first actuation assembly 250, the motor 266 of the second actuation assembly 260 may be a relatively inexpensive motor in some embodiments. For example, the motor 266 may be a low cost stepper motor. In other embodiments, a DC motor or servo motor may be used. In other embodiments, the motor 266 may be any suitable motor. The motor 266 may rotate a gear screw or lead screw, for example, with each step. The gear screw or lead screw may operate to drive the sliding element along the linear actuator 264. In this way, gear screw or lead screw may translate the rotational motion of the motor 266 into linear motion of the linear actuator 264. As with motor 256, in some embodiments, the gear screw or lead screw may couple to a gearbox, which may operate to drive the sliding element along the linear actuator 264. The gearbox may provide for additional torque to the linear actuator 264 in some embodiments. A gearbox may include one or more gears arranged in any suitable configuration. In some embodiments, a planetary gearbox may be used. In other embodiments, any suitable gearbox may be used to assist with moving the sliding element along the linear actuator 264. In some embodiments, any suitable gear reduction of the gearbox may be used to increase the motor and gearbox output torque.

In some embodiments, the motor 266, linear actuator 264, and/or other components may be configured for use in harsh conditions or otherwise outdoor use. For example, mechanical components may be configured to operate without lubricating agents. In some embodiments, for example, the gear screw or lead screw may connect to the linear actuator 264 with a plastic bearing or other element that may function without lubrication, such as for example an IGUS DRYLIN bearing or other device to assist with movement. In some embodiments, the gear screw or lead screw or one or more other components may be constructed of a material such as that used in the IGUS DRYLIN devices. In other embodiments, similar materials or any suitable material may be used to provide for operation without lubricating agents.

In some embodiments, the tracking device 50 may be connected to a power source. The power source may operate the motors 256, 266 of the first and second actuation assemblies 250, 260. The power source may consist of AC and/or DC power, such as battery power, or other power sources in some embodiments. The power source may additionally power a control module in some embodiments.

Figure 28:
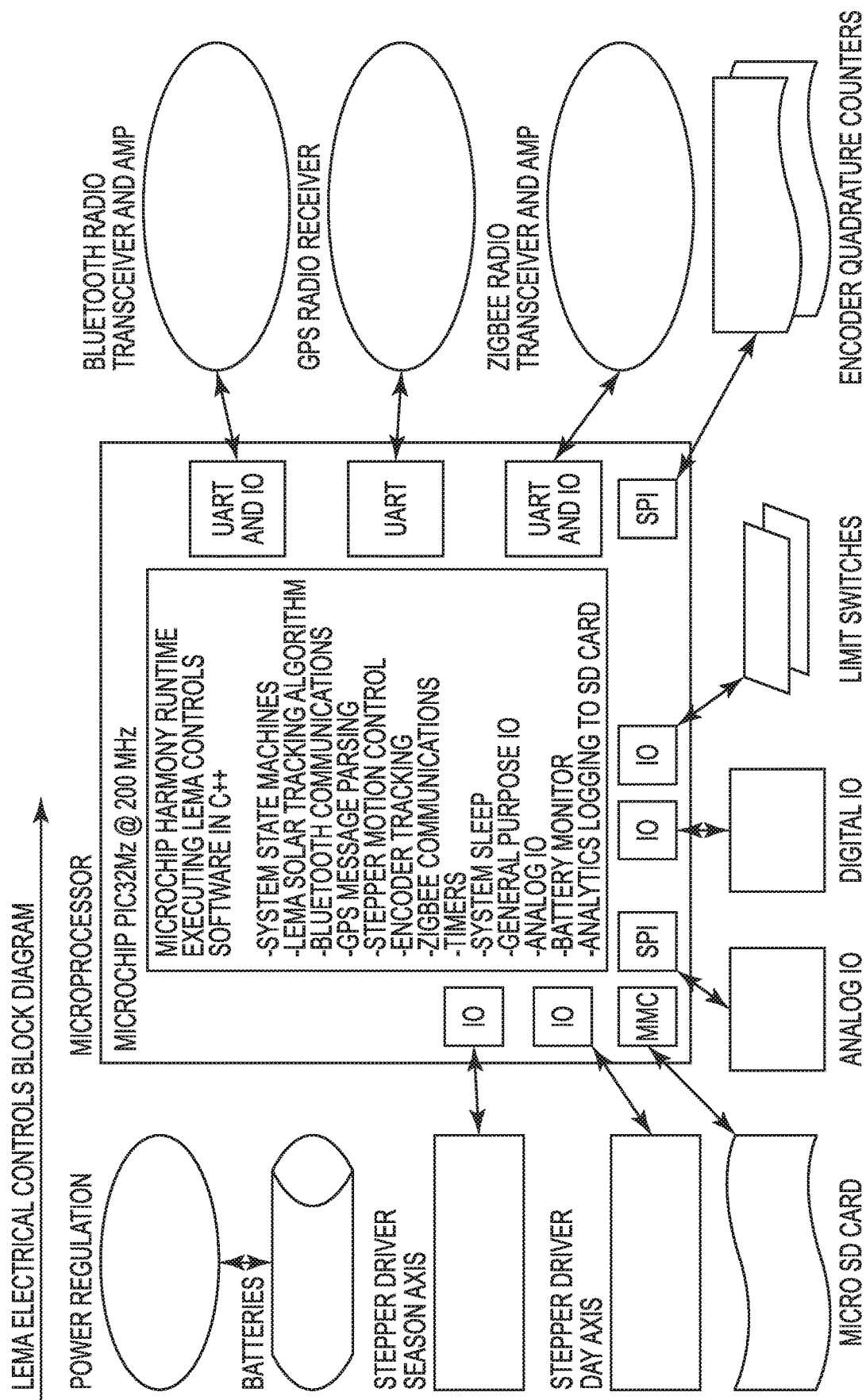
FIG. 28 is a block diagram depicting aspects of a control module, according to one or more embodiments.

In some embodiments, the tracking device 50 may be connected to a control module. The control module may consist of hardware and/or software components. The control module may be connected to the motors 256, 266 in some embodiments. In some embodiments, the control module may determine an approximate position of an object moving across the sky, such as the sun. The control module may include a GPS system in some embodiment, which may include hardware and/or software, such that the control module can determine where on the earth it is located and the local time of day and date. The control module may use hardware and/or software to determine the position of an object in space, such as the sun, from the GPS information. For example, the control module may be configured to determine the azimuth and altitude of the sun from the location of the tracking device 50, as discussed more fully below. The control module may additionally or alternatively be configured to send instructions to the motors 256, 266 to drive the first and second actuation assemblies 250, 260. For example, the control module may instruct the motors 256, 266 to position the payload 51 to be directed toward or relative to the moving object, such as the sun. In some embodiments, the control module may include any or all of the elements shown in FIG. 28. It should be understood that the particular elements shown in FIG. 28 are illustrated as examples. In other embodiments, the control module may include elements similar or related to those shown in FIG. 28 or other elements not depicted in FIG. 28.

Figure 23:
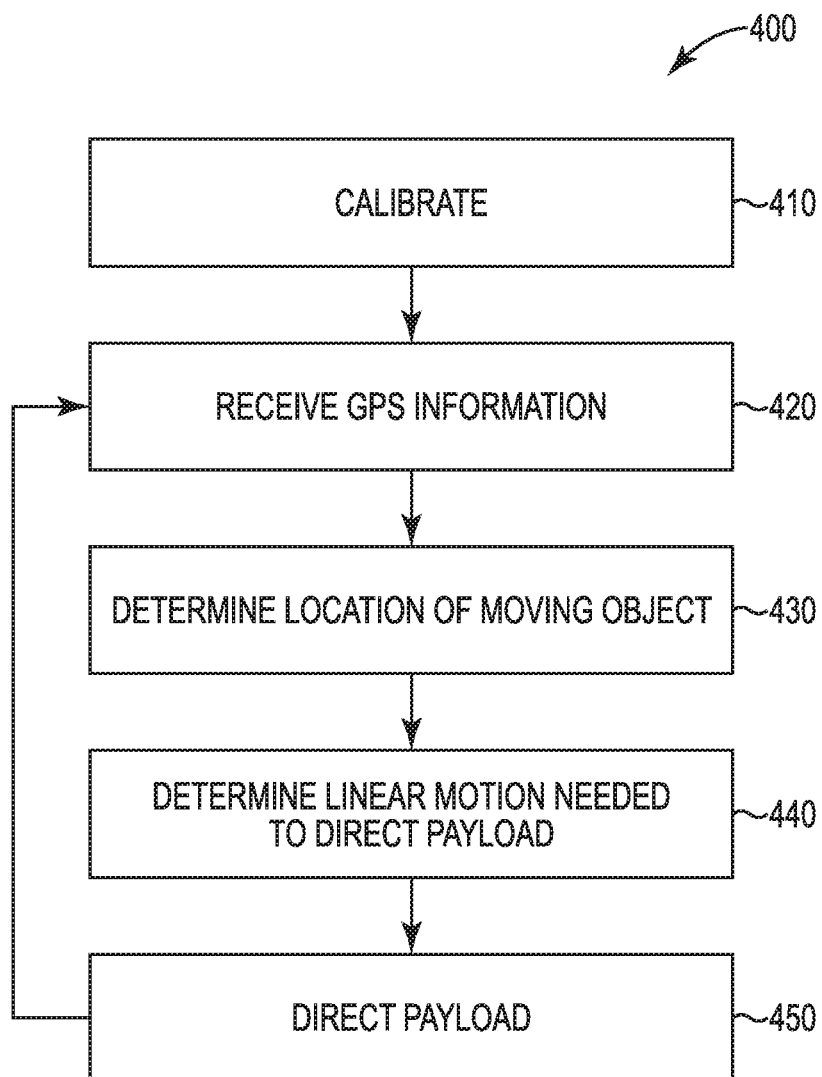
FIG. 23 is a flow diagram depicting a method of tracking a moving object and directing a payload toward the object, according to one or more embodiments.

In use, the tracking device may operate to track the location of an object and direct the payload toward or relative to that object. For example, in some embodiments, the tracking device may use GPS information to determine the location of the device, and from that information, the location of the sun. For example, the tracking device may use such GPS information as a triangulated location, time, and date to determine an altitude and azimuth of an object in space, such as the sun. The tracking device may additionally or alternatively operate to direct its payload, such as one or more solar panels, toward the determined location of the object in space by way of the first and second actuation assemblies. In other embodiments, the tracking device may operate to direct its payload toward a location or object relative to the determined location of the object ins pace by way of the first and second actuation assemblies. Various algorithms may be used to determine an altitude and azimuth based on GPS information. Once the azimuth and altitude are known, the location can be converted into a first motion path, performed by the first actuation assembly, and a second motion path, performed by the second actuation assembly. FIG. 23 illustrates a method 400 that the tracking device may perform in some embodiments. The method may include a calibration step (410), receiving GPS information (420), determining location of the object in space, such as the sun (430), determining positioning of the device (440), and positioning the device (450).

In some embodiments, the device may perform a calibration step (410). In some embodiments, the calibration step may be performed automatically. For example, the calibration step may be performed automatically when the tracking device initially powers on at a location. In other embodiments, the calibration may be performed based on some user input. In some embodiments, the calibration step may be performed partially or entirely manually. The calibration step may include determining one or more assumptions. That is, in some embodiments, the tracking device may operate, at least in part, based on one or more assumptions. For example, in some embodiments, an assumption may be that the longitudinal axis of the spine portion 240 is directed North at one end and directed South at an opposing end. Such assumptions may provide for more accurate positioning of the spine portion and/or payload in some embodiments. Based on these assumptions, the tracking device may be used to track the location of an object from any location on the earth's surface. A correct assumption (such as a first end of the longitudinal axis of the spinal portion is directed North in the Northern Hemisphere) may allow the tracking device to accurately track the location of a moving object and direct its payload accordingly. In this way, it may be appreciated that the tracking device may be able to track the location of an object from any location on the earth's surface merely by changing the assumption(s). For example, an assumption in the Northern Hemisphere may be that a first end of the spinal portion is directed North. For operation in the Southern Hemisphere, the assumption may be changed to reflect that the first end of the spinal portion is directed South.

The calibration step (410) may additionally or alternatively include homing the first and second actuation assemblies. Homing an actuation assembly may include operating the motor, such as a stepper motor, to one end of travel until the motor reaches a limit switch, such as an electromechanical limit switch, defining a limit of travel for the linear actuator. The tracking device may register the point of the limit switch as a zero point of motion of the actuation assembly. Positioning of the device may then be determined based on the zero points of motion for each actuation assembly. This may allow the control module to more accurately determine the relationship between the motor operation and the positioning of the spine portion and/or payload. In some embodiments, once the calibration step is completed, the tracking device may be able to power off and on without the need for recalibration. In some embodiments, the tracking device may know its position each time it turns on after calibration because the actuation assemblies may have a zero back drive. That is, in some embodiments, each actuation assembly may have sufficient forces preventing the linear actuator and/or drive screw or lead screw from moving without the motor drive enabled. In some embodiments, where for example the motors are stepper motors, the motors may additionally or alternatively help to prevent the linear actuators and/or drive screws or lead screws from moving during shut off. Further, in some embodiments, the gearbox may additionally or alternatively help to prevent the linear actuators and/or drive screws or lead screws from moving during shut off.

In some embodiments, a device such as a rotary encoder or linear absolute encoder may be used to determine a position of the linear actuator with respect to the motor operation. In some embodiments, a linear absolute encoder or other similar device may provide a location of the linear actuator to the tracking device, such that the tracking device may know the position of the linear actuator with respect to the motor. In this way, the linear absolute encoder may, at least in part, reduce or obviate the need for homing an actuation assembly. For example, the linear absolute encoder may provide a position of a linear actuator when the tracking device powers on, when the device begins a tracking routine, at the request of the tracking device or a user, and/or at any other suitable time. Each actuation assembly may operate using a linear absolute encoder in some embodiments. The use of one or more linear absolute encoders or similar device may allow the tracking device to correct for any intentional or unintentional movement of the actuation assemblies that may occur during power shut offs or between tracking routines, for example.

As shown in FIG. 23, the tracking device may receive GPS information (420). In some embodiments, the GPS information may be received at the tracking device from a source. For example, the GPS information may be sent to the tracking device over a wired or wireless network. In other embodiments, the device may have GPS hardware and/or software, as discussed above, and may determine the GPS information internally using, for example, data transmitted by a GPS satellite constellation and received by onboard GPS antenna and hardware. GPS information may include location information such as triangulated coordinates, date, and time, each related to the tracking device's current location. Using the GPS information, the tracking device may determine its exact or approximate location on the surface of the earth.

Figure 24A:
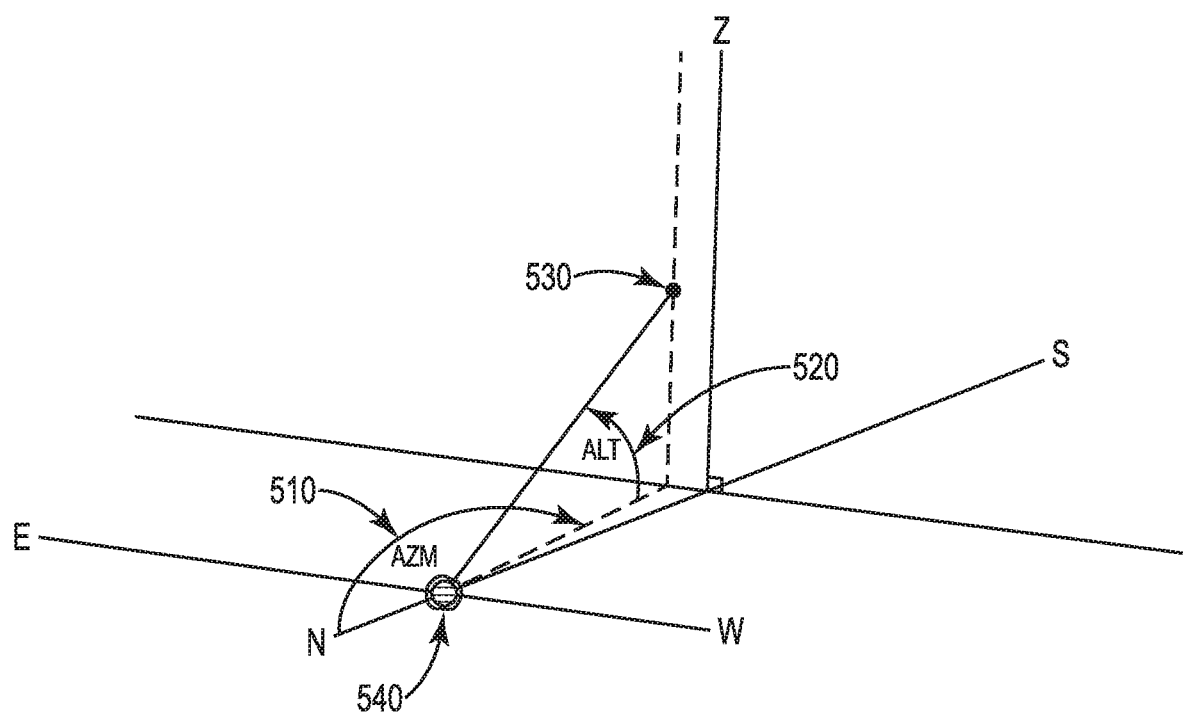
FIG. 24A is a graphical representation of an azimuth and altitude of an object in relation to a tracking device, according to one or more embodiments.
Figure 24B:
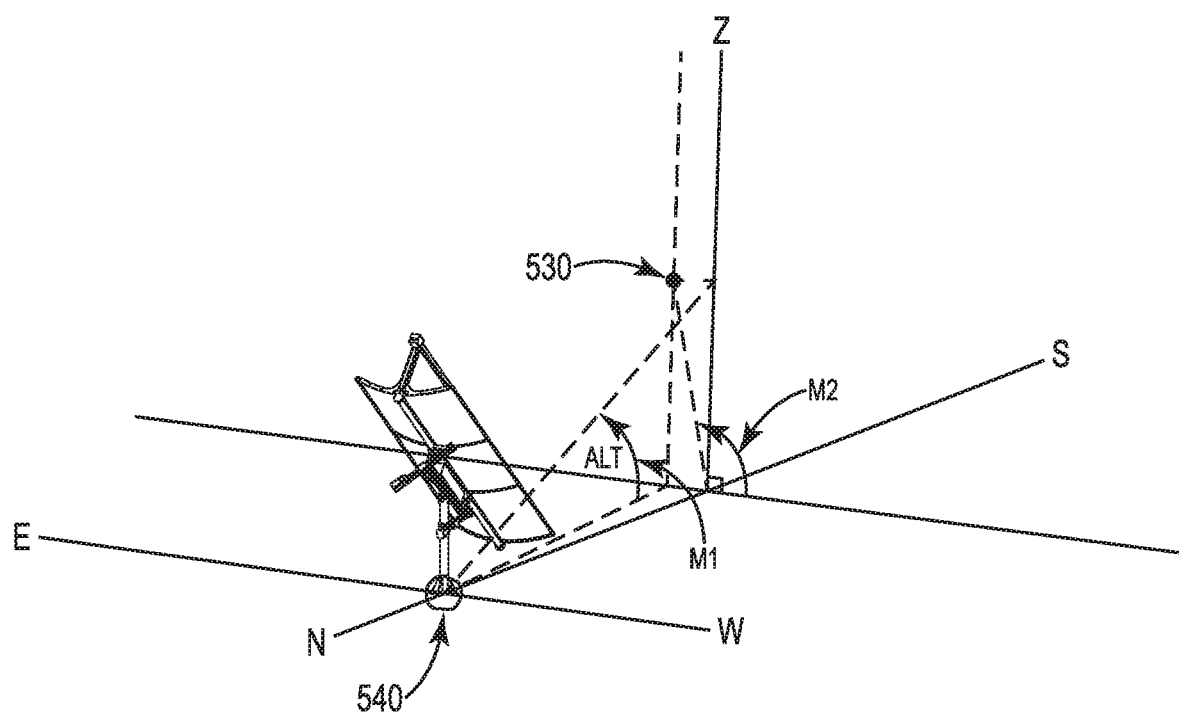
FIG. 24B is a graphical representation of first and second motion paths of a tracking device, based on the azimuth and altitude of FIG. 24A, according to one or more embodiments.
Figure 25:
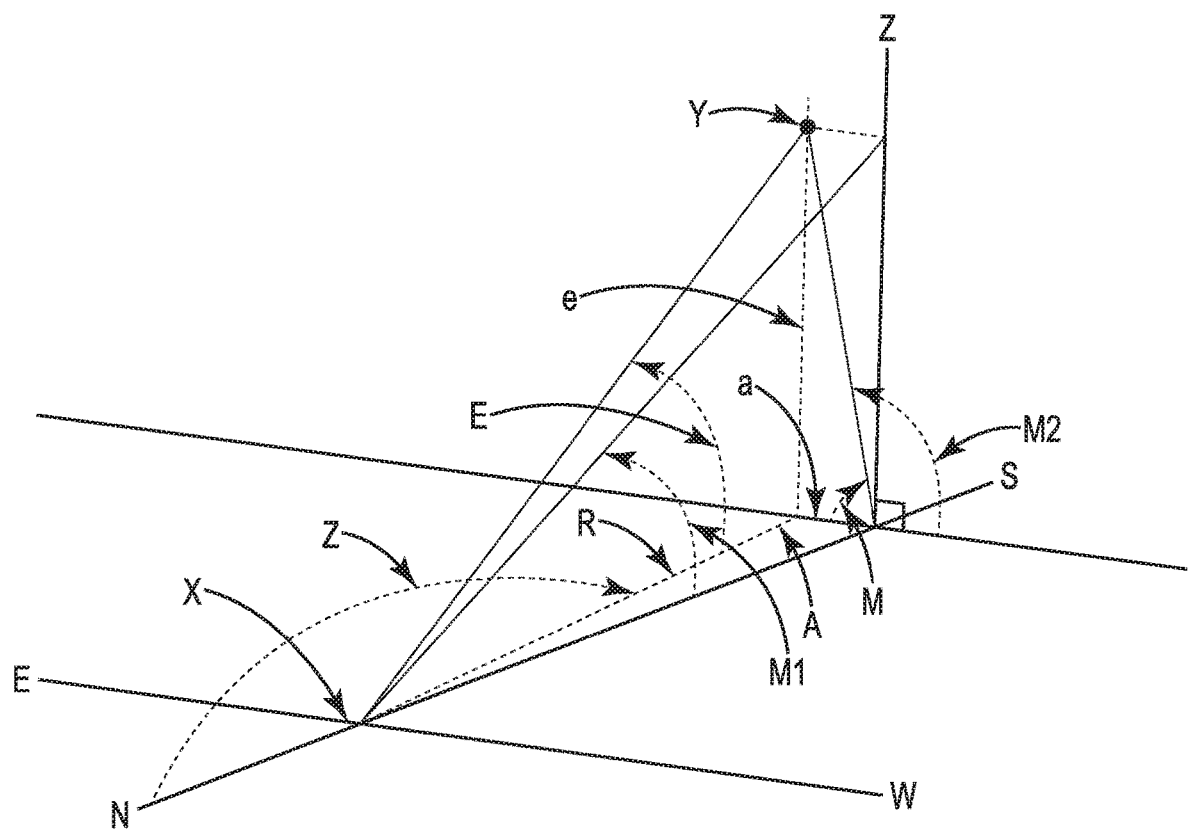
FIG. 25 is a graphical representation of the calculation of the first motion path and the second motion path, according to one or more embodiments.

Based on the received GPS information, the tracking device may determine the location of a moving object in space, such as the sun (430). For example, the tracking device may determine an azimuth and altitude of an object in relation to the device's position. Where the moving object is the sun, the azimuth and altitude may be calculated from the GPS information based on a Solar Position Algorithm, provided by the U.S. Department of Energy, for example. In other embodiments, other calculations or methods may be used to determine the azimuth and altitude of an object or other location information. FIG. 24A graphically illustrates the location of an azimuth 510 and altitude 520 in relation to a location 530 of an object in space, such as the sun, and the location 540 of the tracking device 50. Both locations 530, 540 are shown in relation to North, South, East, and West directions and in relation to a vertical Z axis. The azimuth 510 and altitude 520 combine to provide the location vector 530 of the sun or other object. FIG. 24B graphically illustrates the angle of the first motion path M1, related to the first actuation assembly 250, and the angle of the second motion path M2, related to the second actuation assembly 260. FIG. 25 graphically illustrates the variables used to calculate the angles of the first motion path M1 and the second motion path M2, according to some embodiments. In some embodiments, the angles of the motion paths M1, M2 may be calculated by the following:

$A = 180 - \text{Azimuth}$ $a = |\tan(A)|$ $R = \sqrt{1^2 + a^2}$ $e = R \tan(\text{Altitude})$ $M = \tan^{-1} e/a$ $M1 = \tan^{-1}(e)$ $M2 = (\text{if } A > 180 | M | 180 - M)$ In other embodiments, other equations, calculations, or other methods may be used to determine the angles of the motion paths M1, M2. For example, in some embodiments, the calculation of M2 (i.e., the day axis angle) may be adjusted to accommodate the reference angle established by M1 (i.e., the season axis angle). In some embodiments, this may be performed by transforming the M2 back to an offset cylindrical coordinate system based on M1. This transform would allow for higher accuracy at higher latitudes. Accordingly, by using a trigonometric transform to transform M2 back to an offset cylindrical coordinate system based on M1 and then calculating the M2 angle, the effect on M2 results in higher accuracy across a range of latitudes and seasons.

Figure 26A:
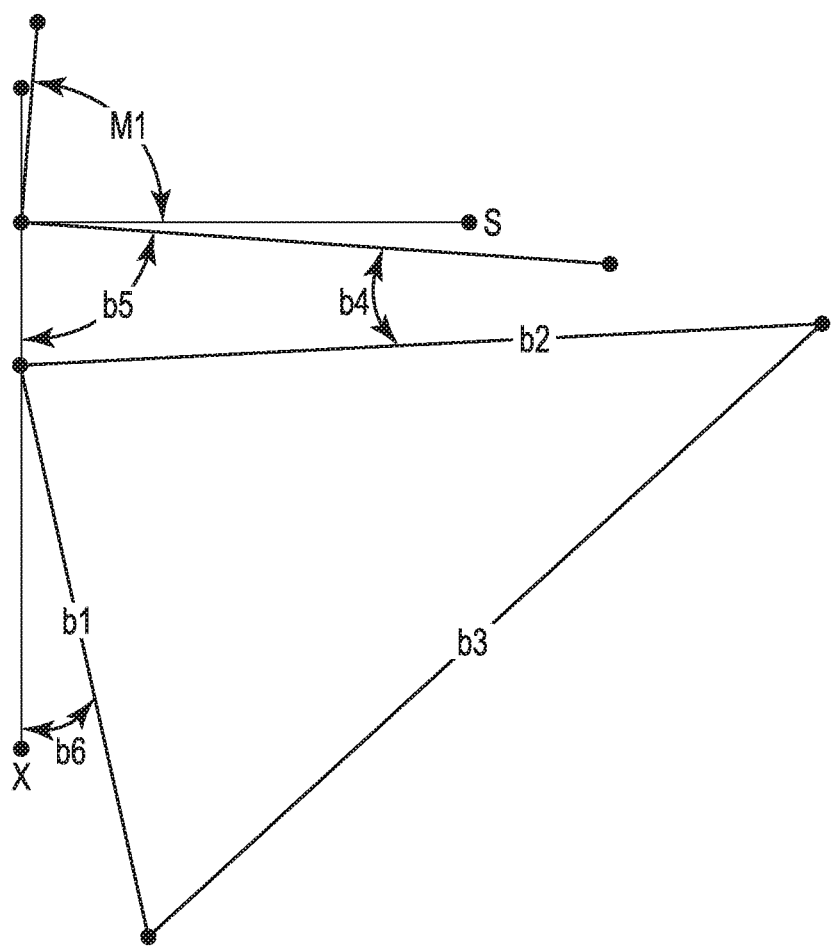
FIG. 26A is a graphical representation of the calculation of the first linear motion, according to one or more embodiments.
Figure 26B:
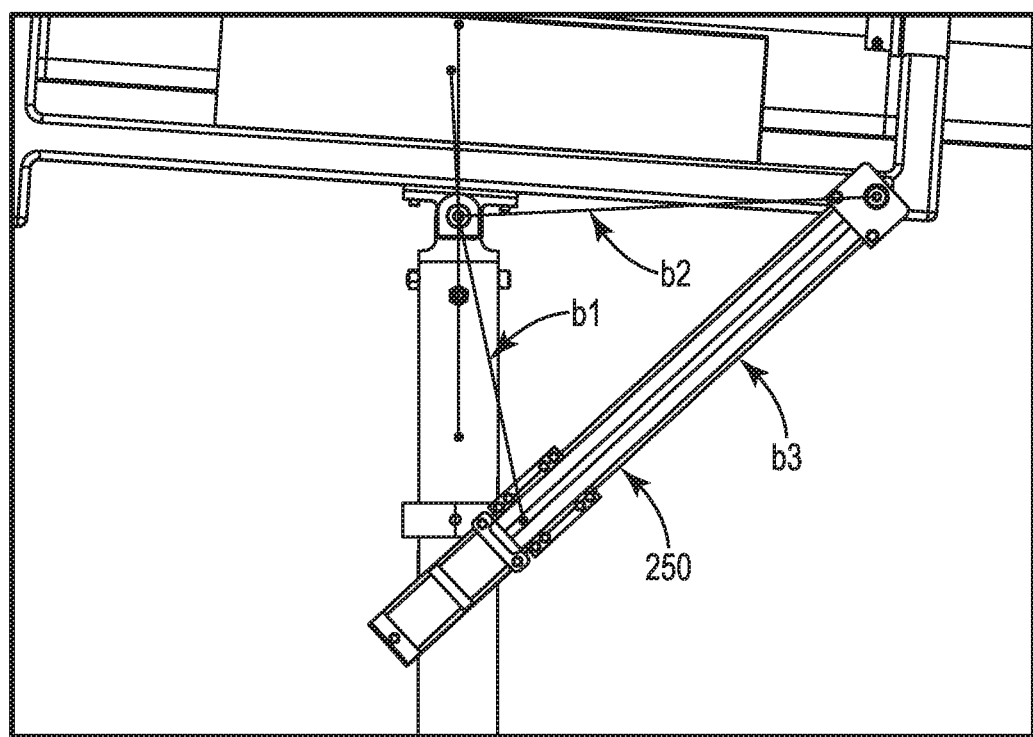
FIG. 26B is an illustration of the location of the variables used to calculate the first linear motion with respect to the first actuation assembly, according to one or more embodiments.

With continued reference to FIG. 23, from the angles of the motion paths M1, M2, the tracking device may determine where to direct the spine portion and/or payload, such that they are directed toward the object (440). For example, in some embodiments, the tracking device may determine a linear distance for each actuation assembly 250, 260 to direct the spine portion and/or payload toward the object. FIG. 26A graphically illustrates the variables used to calculate the first linear motion b3, according to some embodiments. In some embodiments, the first linear motion b3 may be calculated by the following:

$b2 = \text{Length Torque Arm}$ $b1 = \text{Length Pivot Support}$ $b4 = M1 - (b6 - b4)$ $b3 = \sqrt{(b1^2 + b2^2 - 2 \ast b1 \ast b2)}$ $b3 = \text{First Linear Motion}$ FIG. 26B illustrates the locations of the torque arm length b2 and the pivot support length b1 in relation to the first actuation assembly 250. In other embodiments, the first linear motion b3 may be determined using other equations, calculations, or method.

Figure 27A:
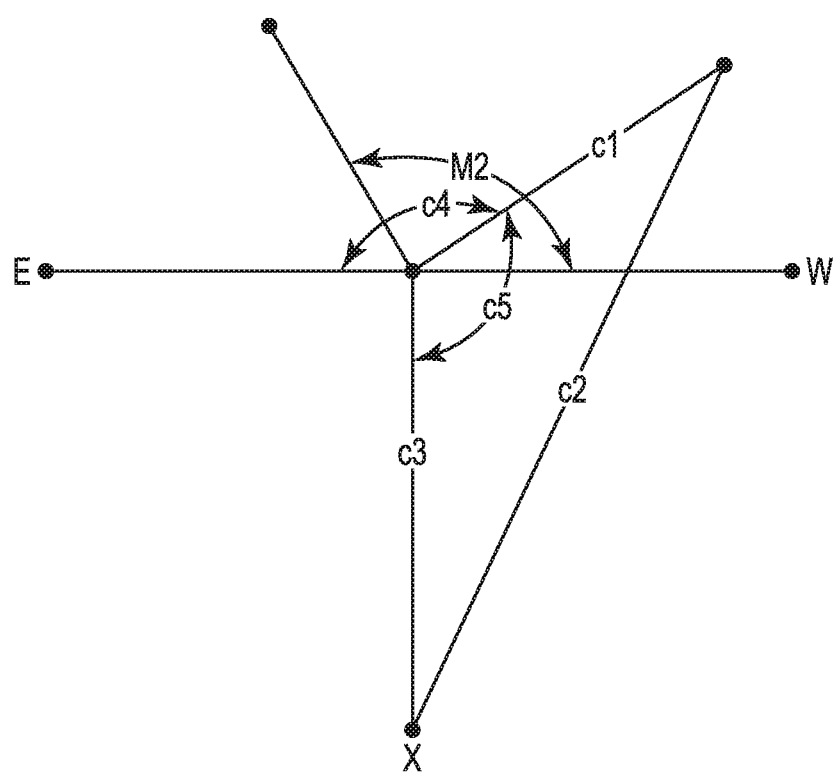
FIG. 27A is a graphical representation of the calculation of the second linear motion, according to one or more embodiments.
Figure 27B:
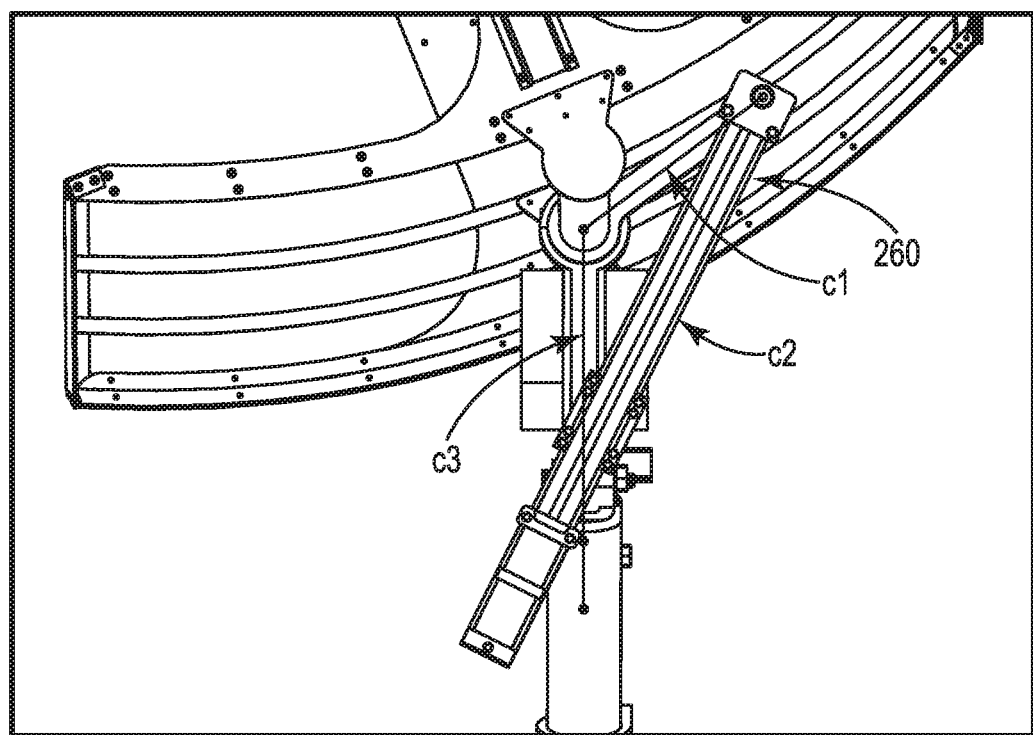
FIG. 27B is an illustration of the location of the variables used to calculate the second linear motion with respect to the second actuation assembly, according to one or more embodiments.

FIG. 27A. Graphically illustrates the variables used to calculate the second linear motion c2, according to some embodiments. In some embodiments, the second linear motion c2 may be calculated by the following:

$c1 = \text{Length Torque Arm}$ $c3 = \text{Length Pivot Support}$ $c5 = M1 + 90$ $c2 = \sqrt{(c1^2 + c3^2 - 2 \ast c1 \ast c3)}$ $c2 = \text{Second Linear Motion}$ FIG. 27B illustrates the locations of the torque arm length c1 and the pivot support length c3 in relation to the second actuation assembly 260. In other embodiments, the second linear motion c2 may be determined using other equations, calculations, or methods. It may be appreciated that in other embodiments, the tracking device 50 may determine a direction for the payload by means other than linear motion. For example, the tracking device may angle the spine portion and/or payload from the ground surface, based on the first and second motion paths M1, M2.

It may be appreciated that the tracking device may be configured to direct its payload at an angle relative to the object moving across the sky. For example, in some embodiments, the payload may be a heliostat or similar device having a mirror or other reflective surface. The mirror or other reflective surface may be directed at an angle relative to the sun's location, such that it may reflect the sunlight toward another point which may be a stationary point. In such embodiments, the first and second linear motions may be calculated differently than above. That is, after determining the sun's azimuth and altitude, the tracking device may determine the first and second linear motions based on the location of the sun in the sky and an angle between the sun's location and the location of the point onto which the sunlight is to be reflected. Generally, the tracking device may be configured to direct its payload at any angle relative to the moving object's location. In this way, it may be appreciated that the tracking device may receive instructions to direct the payload toward generally any vector which may or may not depend on the location of the object being tracked. The instructions may be received locally or remotely over a wired or wireless network. It some embodiments, the positioning of the tracking device may be fully controlled remotely.

With the first and second linear motions b3, c2, the tracking device may instruct the motors to position the actuation assemblies so as to direct the payload toward the moving object or toward a different position (450). Where the motors are stepper motors, for example, the tracking device may determine a number of steps to operate on each motor, so as rotate the payload about the first and second axes of rotation 252, 262 to a desired position.

In some embodiments, the tracking device may repeat steps 420 through 450 intermittently or continuously. For example, in some embodiments, the tracking device may operate continuously to determine the location of the object in space and continuously update the device's positioning. In other embodiments, the tracking device may determine the object's location and reposition the device at intervals. For example, the tracking device may recalculate location and position every hour in some embodiments. In other embodiments, the tracking device may recalculate location and position every 15-45 minutes. In still other embodiments, the tracking device may recalculate location and position every 1-15 minutes in some embodiments. Particularly, the tracking device may recalculate location and position every 2-5 minutes in some embodiments. In this way, the device may take advantage of an object's relatively slow movement across the sky during the course of a day or night. For example, the location of the sun, may not move very far relative to the device over the course of a 2-5 minute interval. In other embodiments, the system may update location and position at different intervals. In this way, for example where the device is directing a payload of solar panels at the sun, the device may be able to recalculate intermittently without substantial solar collection efficiency loss. In addition, the ability to operate intermittently may allow the device to operate with relatively low power consumption. In some embodiments, a low power timer may operate to power the device on at intervals and then the device may power off after adjusting. The process of determining the sun's location and repositioning the device may be a relatively fast process, such that the device does not require much power when it powers on at intervals. For example, in some embodiments, over a twelve hour period of tracking the sun across the sky, the device may be powered off approximately 98% of the time.

In some embodiments, the tracking device may reference a calibration lookup table automatically or manually for purposes of error correction. A calibration lookup table may include a plurality of angles or motion paths relating to directing the payload and corresponding correction angles or correction paths, for example. That is, the lookup table may include error corrections to be performed by the first and/or second actuation assemblies for various calculated motion paths, angles, or object locations. The error corrections of the lookup table may allow the device to correct for various sources of error inherent in or otherwise found in the device. For example, error may be introduced by small inconsistencies in machining, motion of the linear actuator in response to each motor step, small calculation inaccuracies, which may relate to index of refraction of the atmosphere or other atmospheric conditions for example, and/or other sources of error. The lookup table may include a plurality of calculated positions or other calculations as performed by the tracking device, along with corresponding error corrections. In some embodiments, the lookup table may be determined based on actual device calculations performed over time, such as over the course of a day, month, or year, for example. The corresponding error corrections may be determined automatically or manually in some embodiments. Likewise, the lookup table may be populated automatically or manually. In some embodiments, the error corrections may be determined and/or populated in the lookup table using an application such as a mobile phone application. In some embodiments, error corrections may be determined for a limited number of location or position calculations, or for a period of time such as a day, for example, and additional error corrections may be extrapolated. In some embodiments, such calculations and extrapolations may be performed remotely using an application, such as a mobile phone or computer application. In some embodiments, an error correction lookup table or a portion thereof may be directly sent or supplied to the tracking device. In some embodiments, the tracking device may be automatically or manually directed to reference the lookup table periodically, such as after each location and position recalculation. In some embodiments, where a required error correction is not found on the lookup table for a particular calculated location, direction, or motion, bicubic interpolation or another interpolation method may be used to interpolate the needed error correction between two similar correction errors found in the lookup table.

Figure 29:
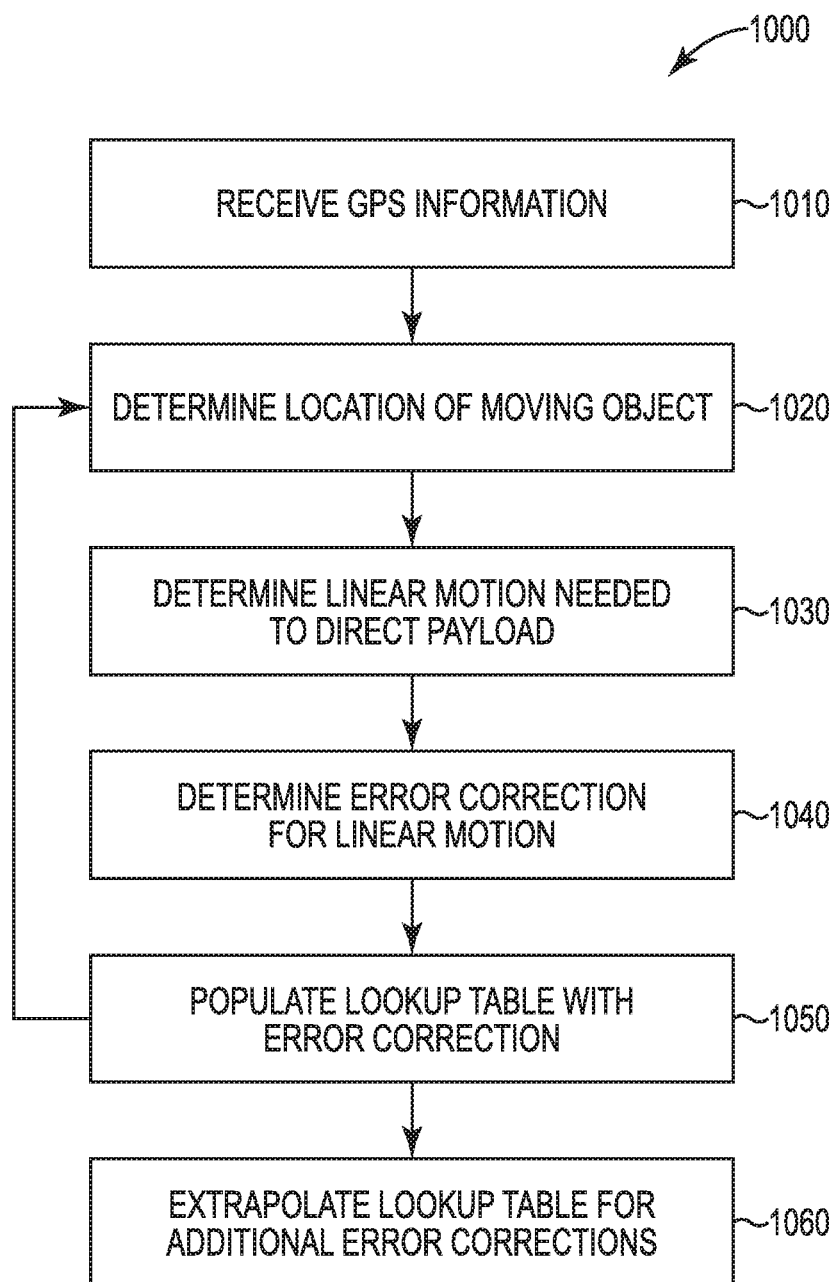
FIG. 29 is a flow diagram depicting a method of populating an error correction lookup table, according to some embodiments.

FIG. 29 illustrates a method 1000 for populating a lookup table with error corrections. As shown, the tracking device may receive GPS information (1010), determine a location of the moving object (1020), and determine a linear motion needed to direct the payload (1030), as described above with respect to method 400. Additionally, in some embodiments, an error correction for the linear motion may be determined (1040). The error correction may be determined automatically or manually, such as through the use of a mobile phone application or other application, locally or remotely. A lookup table may be populated with the determined error correction (1050). In some embodiments, steps 1020 through 1050 may be repeated until a plurality of data points are populated in the lookup table. In some embodiments, additional error corrections may be extrapolated to expand the lookup table (1060). Various extrapolation methods may be used in different embodiments.

Figure 30:
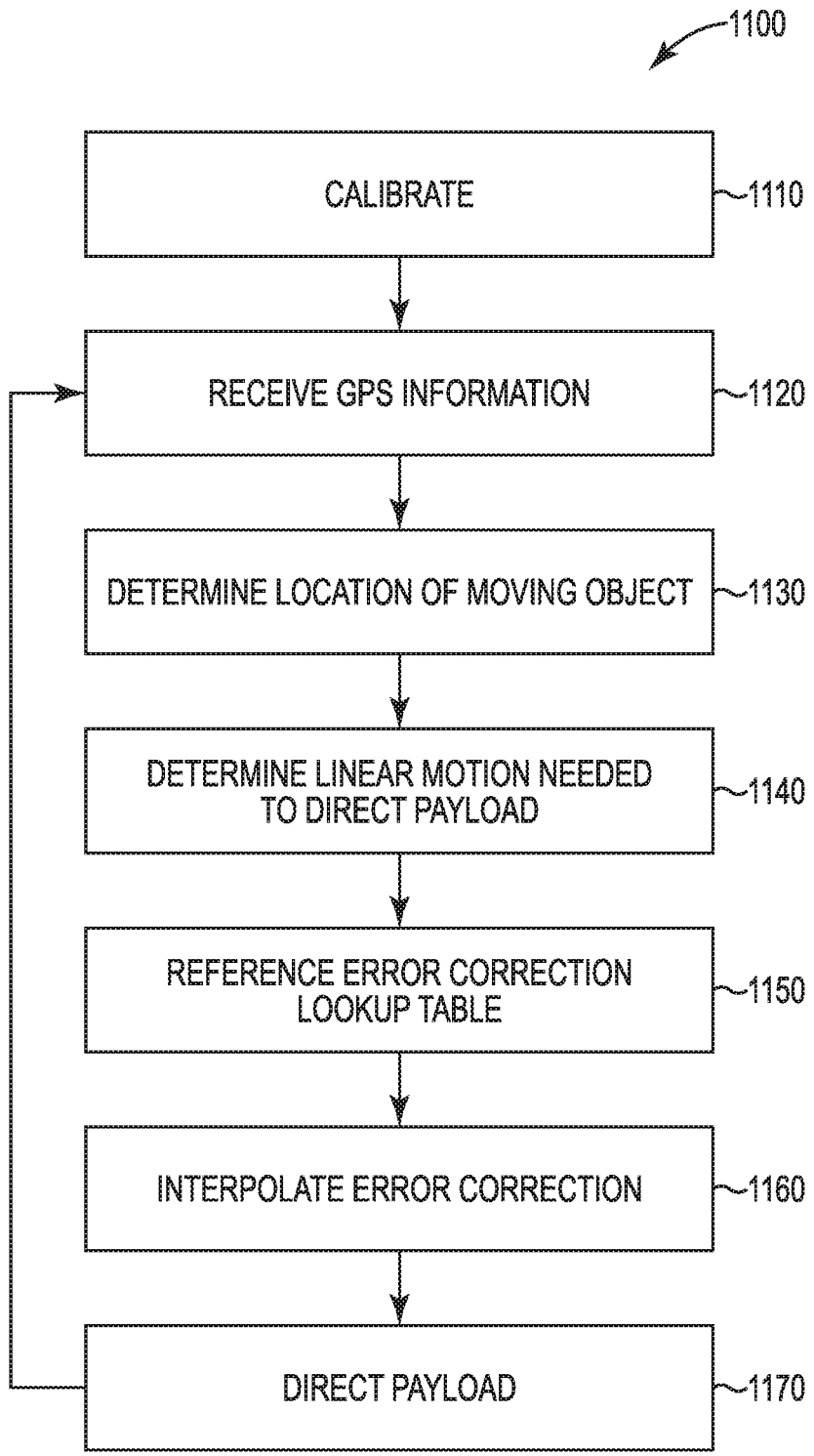
FIG. 30 is a flow diagram depicting a method of tracking a moving object and directing a payload toward the object, according to some embodiments.

FIG. 30 illustrates a method 1100 that the tracking device may perform in some embodiments in order to position the payload with consideration of the lookup table error corrections. As shown, the method 1300 may include a calibration step (1110), receiving GPS information (1120), determining a location of a moving object (1130), and determining a linear motion needed to direct the payload (1140), as described above with respect to method 400. Additionally, the method 1100 may include referencing an error correction lookup table (1150). The tracking device may be directed automatically or manually to reference the lookup table. Additionally, where needed in some embodiments, for example if the particular location or positioning does not fall within the error correction lookup table, the tracking device may interpolate an error correction (1160). Generally, any suitable interpolation method may be used, and in some embodiments, bicubic interpolation may be employed. Taking into account the error correction, the tracking device may direct its payload (1170) using one or more actuation assemblies. In some embodiments, steps 1120 through 1170 may be repeated intermittently or continuously, as described above in order to recalculate location of the tracked object and positioning of the tracking device.

It may be appreciated that the first and second actuation assemblies may relate generally to a season axis and a day axis in some embodiments. That is, the first actuation assembly, first axis of rotation, and first linear motion may be related to a seasonal position of the object being tracked. For example where the object being tracked is the sun, the sun's location may depend in part on the time of year. The positioning of the first actuation assembly may correlate with the sun's location during a particular time of year in some embodiments. Similarly, it may be appreciated that the second actuation assembly, second axis of rotation, and second linear motion may be related to a daily position of the object being tracked. For example where the object being tracked is the sun, the sun's location may depend in part on the time of day. The positioning of the second actuation assembly may correlate with the sun's location at a particular time of day in some embodiments. It may additionally be understood that while the first and second actuation assemblies may correlate generally with time of year and time of day, both actuation assemblies and axes of rotation may be used to direct the payload at any time of day or year. For example, although the first actuation assembly may generally correspond with seasonal location, the first actuation assembly may additionally rotate the payload about the first axis of rotation to track the object based on the time of day. That is, both actuation assemblies may be used to track the object's movement across the sky during the course of a day, for example.

In various embodiments, a tracking device of the present disclosure may be mounted to or generally located on a ground surface, a platform surface, or a tower surface or other structure, such as a cell phone or other communication tower or a solar power tower. For example, where the tracking device is mounted on a cell phone or other communication tower, the tracking device may track the location of a satellite and/or may direct its payload toward the satellite. In other embodiments, the tracking device may be located on a solar power tower, where the device may track the location of the sun and/or may direct its payload, such as mirror or other reflective surface, at an angle relative to the sun such that sunlight may be reflected toward a power collector or other device on the power tower. In such tower embodiments, the tracking device may be controlled or directed automatically and/or remotely, in some embodiments.

In some embodiments, the tracking device may operate, at least in part, over a wired or wireless network. A wireless connection may be, for example, an internet, Wi-Fi, Bluetooth, or other wireless connection. In some embodiments, the device may have a digital radio such as a Zigbee radio, which may allow the tracking device to communicate with one or more additional tracking devices or other communication devices over a wireless network. In this way, one or more tracking devices may be configured to share information, such as GPS information, tracking and positioning information, power consumption information, efficiency information, and/or other information over a wireless network. In some embodiments, the network and communication link may be maintained during power shut offs.

In some embodiments, the tracking device may receive an instruction to turn away from the object being tracked across the sky or otherwise away from its point of direction. For example, where the tracking device is tracking the sun to collect solar light or radiation, if the tracking device reaches some input or output limit or it is otherwise determined that solar light or radiation need not be collected for a period of time, the tracking device may be configured to receive an instruction to direct the payload away from the sun. Such an instruction may be received locally or remotely over a wired or wireless connection. For example, the instruction may be received from a device having a Zigbee radio. In some embodiments, the instruction may be received automatically when a sensor, for example, determines that the tracking device should stop collecting solar light or radiation. In other embodiments, the instruction may be input into the tracking device manually or may be received based on some user input.

In some embodiments, one tracking device may operate as a node to control one or more additional tracking devices. For example, one tracking device may aggregate the information received from multiple tracking devices. The single tracking device may direct and control positioning of the additional tracking devices, in some embodiments.

In some embodiments, a software application may allow a computing device to communicate with one or more tracking devices. A computing device may be a desktop or laptop computer, tablet, or mobile phone, for example. The software application may be used to communicate with one or more tracking devices over a wired or wireless network. The software application, such as a mobile device application for example, may allow a user to calibrate the tracking device locally or remotely. The application may further allow a user to collect data and/or provide user inputs locally or remotely.

In the foregoing description, a tracking device has been described. The tracking device may be configured to track an object in space, such as the sun, as the object moves across the sky. The tracking device may further be configured to direct a payload toward the object in space or toward an angle relative to the object in space. The tracking device may continuously or intermittently determine the location of the moving object, and adjust the position of the payload accordingly. The tracking device may calculate the position of the moving object based on GPS information, such as triangulated coordinates of the tracking device, date, and time. Generally, the tracking device may be capable of tracking an object such as the sun from anywhere on the earth's surface. The tracking device may employ one or more actuation assemblies to position the payload toward or relative to the moving object. The one or more actuation assemblies may operate through linear motion, in some embodiments. Moreover, the tracking device may operate with relatively low power consumption. The tracking device may communicate with one or more additional tracking devices or other communication devices over a wired or wireless network.

System Operation

In use, the system may be set up by providing the several elements and arranging them so as to be exposed to sunlight and such that water may be supplied. In some embodiments, the support structure of the system may be arranged on a relatively flat surface in a manner such that the spine of the support structure is arranged along a North/South axis on the surface of the earth. Where the device is positioned north of the equator, the upper end of the fluid control system (i.e., the end having the control valve and the pressure relief device) may be arranged on the north end of the system. In contrast, where the device is positioned south of the equator, the upper end of the fluid control system may be arranged on the south end of the system. The control electronics may be turned on allowing the GPS system in the controls to identify the location of the device on the surface of the earth and also identify the date and time. With this information, the control electronics may be able to identify the position of the sun relative to the device. The system may then automatically actuate the seasonal actuation assembly and the daily actuation assembly to tip the solar collector to a position facing the sun.

In addition, portions of the fluid control system may be arranged. For example, the collection reservoir may be arranged in a position to collect water and may be positioned at an elevated position relative to the remaining parts of the system. In some embodiments, the collection reservoir may be placed on a hill or on a stand, tower, or other device for elevating the collection reservoir. The feed line may be secured to the collection reservoir and the preheat heat exchanger. In addition, the effluent line may be connected to the preheat heat exchanger and to the treated fluid collection reservoir. The treated fluid collection reservoir may be arranged at a non-elevated position relative to the system such that the collection reservoir may receive water from the system based on a gravity flow, for example. In some embodiments, the return line, the preheat heat exchanger, the effluent line, and the treated fluid collection tank may be sanitized so as to avoid a situation where treated fluid is run through a contaminated line or device or placed into a contaminated container.

Water from the elevated collection reservoir may be allowed to flow into the system. The degassing valve may allow air or gas in the system to be released as water or fluid flows into the system. In some embodiments, to avoid overheating and damage to the system, water may be provided to the system prior to having the system face the sun. For example, were the system to heat up prior to allowing water or fluid to enter, the water may boil as it enters creating high pressures that may damage the system.

Figure 31:
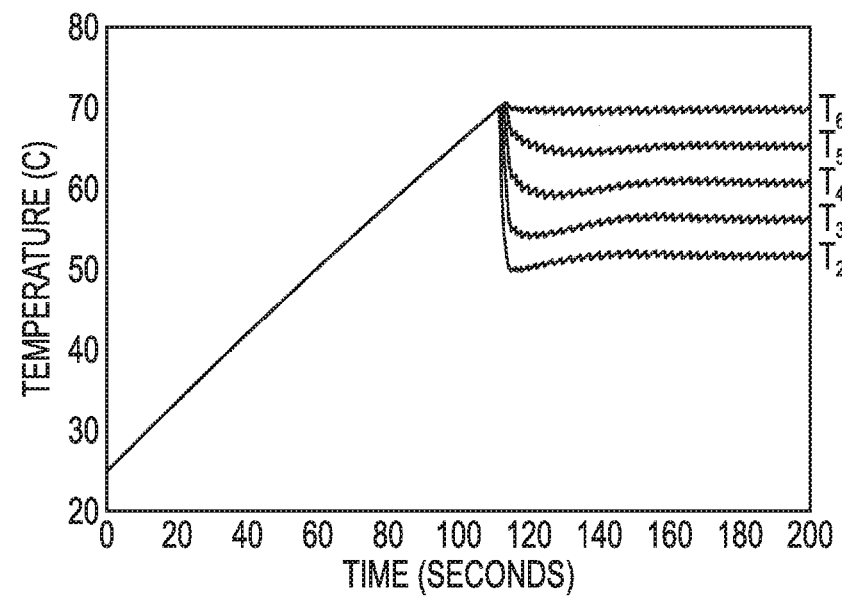
FIG. 31 is a graphical representation of the temperature of fluid in the fluid heating system at particular locations over time, according to one or more embodiments.

With the system primed, gases removed, and having the system facing the sun, the system may begin heating the water or fluid in the elongated flow element of the fluid heating portion. As shown in FIG. 31, the temperature of the water or fluid in the elongated flow element may generally increase substantially uniformly until the fluid in the control valve assembly reaches a thermal temperature causing one or more portions of the valve to open. As the valve opens, fluid or water in the elongated flow element may begin to flow. Accordingly, a temperature gradient across the elongated flow element may begin to develop because cool or slightly preheated water may enter the inlet end of the elongated flow element and it may continue to get warmer as the water flows through the elongated flow element and is continually exposed to additional heat. As shown in FIG. 31, the system may reach a state of quasi equilibrium as the valve opens and closes periodically and begins to allow water or fluid to pulse through the elongated flow element. The control valve assembly may be particularly designed, constructed and calibrated to ensure that the water or fluid in the elongated flow element is exposed to sufficient temperatures for sufficient lengths of time such that all relevant pathogens are inactivated. As the control valve opens and closes, pasteurized water may flow through the control valve assembly and into the return line. The water or fluid may then flow through the return line and into the preheat heat exchanger. As the pasteurized water flow through the preheat heat exchanger, heat from this pasteurized water may be transferred to the incoming water from the feed line allowing this water to increase in temperature before entering the elongated flow element. The pasteurized water may then pass into the effluent line and into the treated water collection reservoir where it may be available for use.

As mentioned, the control valve assembly may be particularly designed, constructed, and calibrated to ensure that the water or fluid passing through the control valve assembly is fully pasteurized. That is, the use of thermally activated valves inherently results in a pulsing type flow, where, when the valve opens water flows, which allows cooler water to reach the valve causing the valve to close. When the valve is closed, the standing water near the valve then increases in temperature due to remaining exposed to the heat source. As such, the valve then opens once again. During the process of water flowing through the valve and the time it takes for the valve to react to the cooler temperatures, a risk exists that non-pasteurized water may escape through the valve unless the valve is properly designed. Accordingly, the valve may be designed and calibrated to make sure that the temperatures at which it opens and closes are such that no unpasteurized water escapes. At the same time, substantially continuous flow or quasi continuous pulsing flow of fluid may be desired so as to efficiently utilize the heat source and efficiently create pasteurized water.

Pathogen Inactivation

In order to discuss how to analyze pathogen inactivation for pulsing flow fluid, an initial discussion of pathogen inactivation may be helpful. Two related methods of pathogen inactivation may be provided. In some embodiments, a decimal reduction time may be used which may be the time required for 1-log reduction in pathogens. Mathematically, this may be expressed as:

$$\log\left(\frac{N_t}{N_0}\right) = \frac{-t}{D} \qquad \text{Eq. 1}$$

In this equation, $N_0$ may be initial pathogen population and $N_t$ may be the population at a later time t. The value of D (i.e., the decimal reduction time) may depend on the exposure temperature and the type of pathogen. The value of D may decrease relatively quickly as temperature increases. Values of D at other temperatures can be found from:

$$\log\left(\frac{D}{D_r}\right) = \frac{-(T - T_r)}{z} \qquad \text{Eq. 2}$$

where the term $D_r$ is the decimal reduction time known at some reference temperature $T_r$. On the other hand, D is the desired reduction time at a different temperature T. The symbol z has units of ° C. The information presented in the Equations 1 and 2 may be useful particularly for isothermal exposures. However, it is often more convenient to calculate instantaneous rates of pathogen destruction through a first-order rate model which can be expressed as $$\frac{dN}{dt} = -kN \qquad \text{Eq. 3}$$

For isothermal exposures, Equation 3 can be integrated in time, to give $$\ln\left(\frac{N_t}{N_0}\right) = -kT \qquad \text{Eq. 4}$$

and a comparison of Equations (1) and (4) may allow a relationship between k and D such as:

$$k = \frac{2.303}{D} \qquad \text{Eq. 5}$$

For time-varying situations, such as the fluid system in the present application, the integration of Equation (3) may be carried out numerically so that $$\frac{dN}{dt} = \frac{(N_{t+\Delta t} - N_t)}{\Delta t} = -kN_t = \frac{2.303}{D_r} \cdot 10^{\frac{(T - T_r)}{z}} \cdot N_t \qquad \text{Eq. 6}$$

which will be solved using a forward-stepping integration scheme. With values of D (at a reference temperature) and z for various pathogens solutions may be determined. Alternatively, values of D at two separate temperatures can be used.

Figure 32:
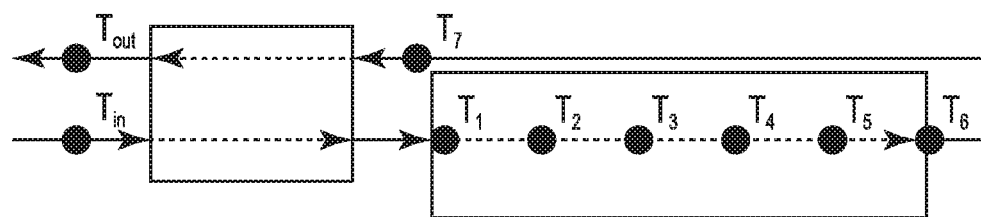
FIG. 32 is a schematic diagram of the temperature locations of FIG. 20, according to one or more embodiments.

This microbiologic model may be applied to described fluid heating system. That is, with knowledge of the parameters of the system described, temperatures of the flowing fluid in the elongated flow element may be calculated and analysis of the related effect on pathogen inactivation may be determined. For purposes of the analysis, several temperatures at several locations within the system may be identified. For example, $T_{in}$ may be the incoming temperature of the fluid coming into the heat exchanger (i.e., the fluid temperature in the feed line). Additional temperatures $T_1$-$T_6$ may be calculated along the length of the elongated flow element. That is, as shown in FIG. 32, T1 may be the temperature as the fluid enters the elongated flow element (i.e., the temperature after passing through the preheat heat exchanger). Temperatures $T_2$, $T_3$, $T_4$, $T_5$ and $T_6$ may be temperatures calculated at equal distances along the length of the elongated flow element with $T_6$ being the exit temperature and/or the activation temperature for the control valve assembly. The volumes of fluid between each of these temperature locations may constitute control volumes where the temperature rise across each control volume may be determined from an energy balance as described below. In addition to the above-mentioned temperatures, an additional temperature $T_7$ where the return tube enters the preheat heat exchanger may be calculated. In some embodiments, adequate insulation of the return tube may be assumed such that $T_6$ is equal to $T_7$. $T_{out}$ may be the temperature of the fluid as it exits the preheat heat exchanger and heads toward the treated water collection reservoir.

With focus on the solar collector or other heat source, the time wise evolution of temperature may be based on an unsteady energy balance as follows:

$$\Delta q = \dot{m} \cdot c_{p,fluid}(T_{n+1} - T_n) + \left[(m \cdot c_p)_{fluid} + (m \cdot c_p)_{pipe}\right]_n \frac{dT_n}{dt} \quad \text{Eq. 7}$$

where the symbol $\Delta$ may reflect that the energy balance is performed over a small region (i.e., one of the control volumes along the elongated flow element). The symbol $\dot{m}$ may be the mass flow rate and $c_p$ may be the specific heat of either the fluid or the pipe wall as respectively called for. The symbols $T_n$ and $T_{n+1}$ represent the temperatures at the inlet and the exit of a particular control volume. The first term on the right hand side may be the heat that is used raising the temperature of the flowing fluid. The second term on the right may be the energy used to raise the temperature of the pipe and the fluid within the pipe. It may be assumed that the fluid and the pipe in any control volume are at equal temperatures; axial conduction may be neglected.

The net influx of heat, $\Delta q$, may include energy gain by thermal radiation as well as energy lost by both convective and infrared heat loss. For example, $\Delta q$, may be found from:

$$\Delta q = (\Delta q)_{solar} - (\Delta q)_{convection} - (\Delta q)_{IR} \quad \text{Eq. 8}$$

where $$(\Delta q)_{solar} = I_{solar} \cdot \Delta A_{collector} \cdot F \quad \text{Eq. 9}$$

is the solar influx of heat. The symbol $I_{solar}$ may be the insolation flux at the ground, $\Delta A_{collector}$ is the parabolic solar collection area for the control volume under consideration. The term F represents losses from incomplete reflection at the mirror surface or absorption at the pipe which resides along the focal axis and any imperfect alignment of the pipe along the focal line. This number is expected to be very close to 1 for high-quality parabolic systems.

The convective losses may be calculated from $$(\Delta q)_{convection} = \bar{h} \Delta A_{surf}\left(\frac{(T_{n+1} + T_n)}{2} - T_{amb}\right) \quad \text{Eq. 10}$$

where the symbol h is the average convective coefficient on the control volume under consideration. This value depends on both local wind as well as the temperature of the pipe if buoyant flow makes an impact. Correlations are available for convective calculations in many resources. Calculations show that final temperatures are nearly independent of the convective coefficient so long as a reasonable value is assigned.

In a similar manner, the heat loss by infrared radiation may be calculated from $$(\Delta q)_{IR} = \epsilon \sigma \Delta A_{surf}\left(\left(\frac{(T_{n+1} + T_n)}{2}\right)^4\right) \quad \text{Eq. 11}$$

where $\epsilon$ and $\sigma$ are the emissivity and Stefan-Botzmann constant, respectively. The control volume temperature in Equation 11 may be expressed in absolute units. In Equation 11, no account has been made for incoming infrared radiation from above the pipe. However, this component is expected to be much smaller than other components.

For high-performance solar concentrators, a surrounding tube or housing may be used to provide thermal insulation. The presence of such a tube may be incorporated into the present analysis through the inclusion of a series of thermal resistance which may be applied to the heat loss. On the other hand, for low-cost solar pasteurization systems designed for rugged environments and the developing world, such high-cost insulating tubes may be difficult to justify.

When terms from Equations 8-11 are evaluated at timestep i, temperature at the following time i+1 may be found by numerically integrating Equation 7 as $$T_{n+1}^{i+1} = T_{n+1}^i + \Delta t \left[\frac{\Delta q - \dot{m} \cdot c_{p,fluid}(T_{n+1} - T_n)}{\left[(m \cdot c_p)_{fluid} + (m \cdot c_p)_{pipe}\right]_n}\right]^i, n = 1, 2, \ldots \quad \text{Eq. 12}$$

In FIG. X, temperatures T7=T6. The final unknown is the temperature T1. This value may be determined using an effectiveness-NTU heat exchanger analysis method which gives $$T_1^{i+1} = T_{in} + e(T_7 - T_{in})^i \quad \text{Eq. 13}$$

where e is the heat exchanger effectiveness.

If a thermal valve is used to control flow when temperatures are below a threshold, then $\dot{m}=0$ when the valve is closed (i.e., the water is not flowing). The valve remains closed when the temperature at the valve (typically at the exit of the elongated flow element) is less than valve operation temperature. If the valve has opened, then the mass flow rate may be determined by considering a fluid mechanical-energy equation, $$\rho g h_{tank} = \frac{\rho V^2}{2} + f\frac{L}{d}\frac{\rho V^2}{2} + \Delta P_{minor} \quad \text{Eq. 14}$$

Here, $\Delta P_{minor}$ are the contributions to pressure loss other than friction. Equation 14 allows calculation of the fluid velocity within the pipe, V from $$V = \sqrt{\frac{2gh}{\left(f\frac{L}{d} + K_{inlet} + K_{valve}\right)}} \qquad \text{Eq. 15}$$

Here, the $K_{inlet}$ and $K_{valve}$ are minor loss coefficients at the pipe inlet and at the valve. If there are other minor losses within the system, their loss coefficients may be added in the denominator. The symbol f is the friction factor which may be determined based on the flowrate and Reynolds number at the prior time step. With the fluid velocity, and consequently mass flow rate now known, the entire calculation algorithm can be articulated.

At time step t=0, all temperatures may be initialized to a starting value equal to the water temperature in the storage container. At later time steps, Step 1: $T_{in}$—temperature of water in the storage tank
Step 2: $T_1$ is solved from Equation 13 to account for preheat at the heat exchanger
Step 3: $T_2, T_3, \ldots T_6$ may be found from Equation 12
Step 4: $T_7$–$T_6$
Step 5: Compare $T_6$ to a valve operation temperature, updated mass flow rate Equation 15, repeat step 1.

Figures 33, 34:
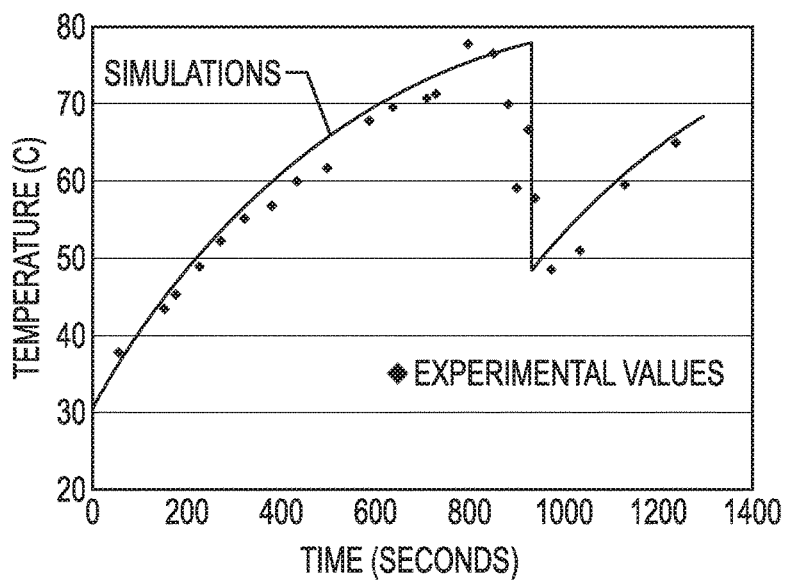
FIG. 33 is a table showing parameter data for calculating the temperature of the fluid in the fluid heating system, according to one or more embodiments.
FIG. 34 is a graphical representation showing correspondence between calculated temperatures and experimental temperatures.

Results of the temperature calculation can be seen in FIG. 31 for a particular set of input parameters. In the image, five of the temperatures are shown which represents temperatures along the elongated flow element. The settings for the calculation are shown in FIG. 33. The kinematic viscosity of water may be calculated at each time step by the following interpolating function $$v(T) = 1.10 \times 10^{-10} \cdot T^2 - 2.17 \times 10^{-8} \cdot T + 1.37 \times 10^{-6} (m^2/s) \qquad \text{Eq. 16}$$

with temperatures in degrees C. to account for the impact of temperature on viscosity.

The image shows that an initial unsteady period may exist when the temperature of the fluid in the elongated flow element rises substantially uniformly. That is, the temperature remains below the valve operation temperature and, as such, all of the temperatures rise as the temperature of the pipe increases. As shown, at approximately 110 seconds, the valve activation temperature is reached and the valve begins to operate allowing water to flow through the system. As a result, with incoming water from reservoir being relatively cool, temperatures at the upstream locations in the elongated flow element are reduced and a quasi-steady state of temperatures may be reach. It is to be appreciated that, as shown, the temperatures at each location oscillate as the valve opens and closes regularly. Moreover, the quasi-steady state temperatures at each location may drop to a particular temperature and now that water is flowing, temperatures $T_2$ may benefit from the effect of the heat exchanger and may rise slightly from about 110 seconds to about 150 seconds.

As shown in FIG. 34, a full scale model of the system showed reasonably good correlation between calculated values of temperature compared to actual measured values.

Figure 35:
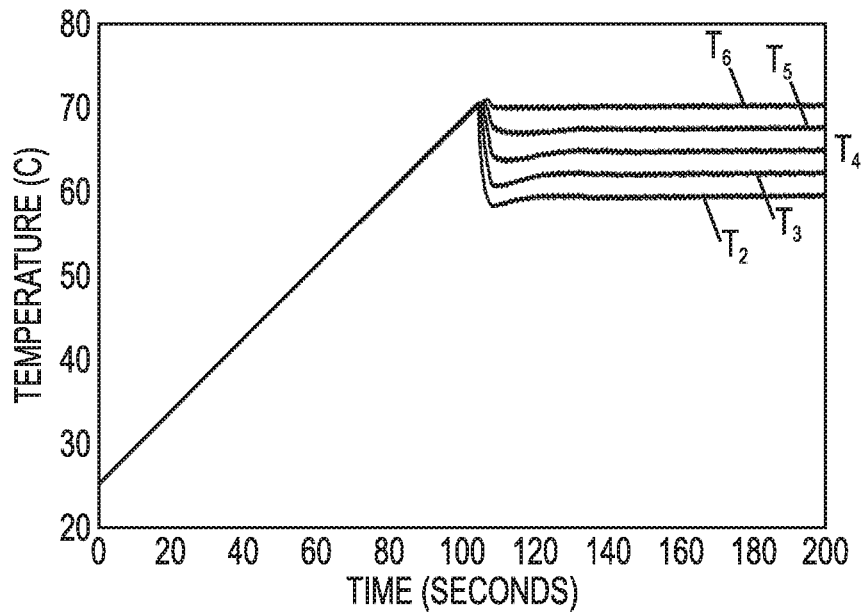
FIG. 35 is a graphical representation of the temperature of fluid in the fluid heating system at particular locations over time, according to one or more embodiments.

The above-described model may allow for assessing the impact of changes in the operating parameters. For example, a higher performance heat exchanger (e=0.7) may increase the recovery heat from the treated stream and raise the inlet temperature of the fluid entering the collector. The result may be seen in FIG. 35. As shown, the temperatures are more tightly bounded because the temperature at $T_2$ is higher as a result of the increased heat exchanger efficiency and the temperature $T_6$ remains controlled by the valve operation temperature.

Figure 36:
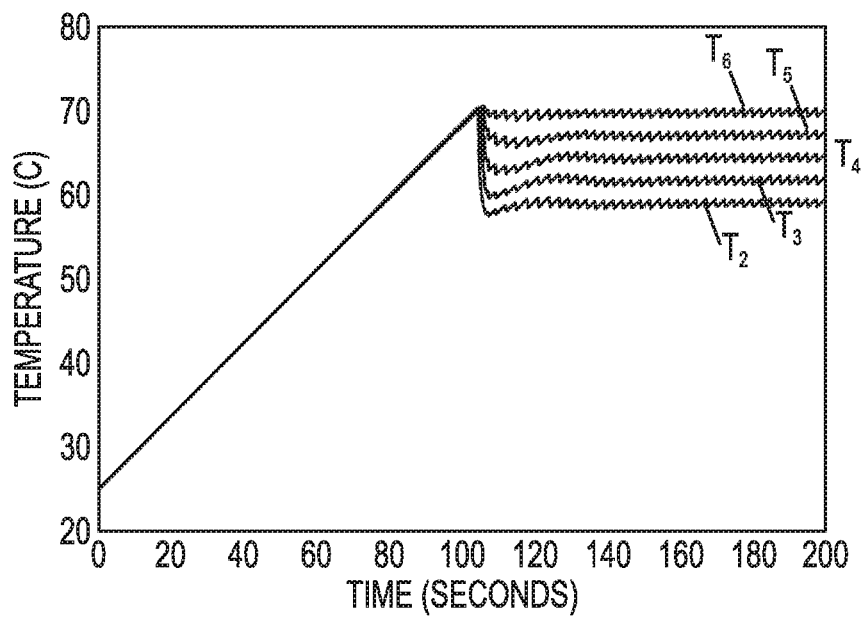
FIG. 36 is a graphical representation of the temperature of fluid in the fluid heating system at particular locations over time, according to one or more embodiments.

The impact of the valve coefficient may be assessed with reference to FIG. 36. There, the valve loss coefficient has been changed from 10 to 2. As a result, the temperature levels are mostly unchanged, but the variation in temperatures at each location has increased.

Figure 37:
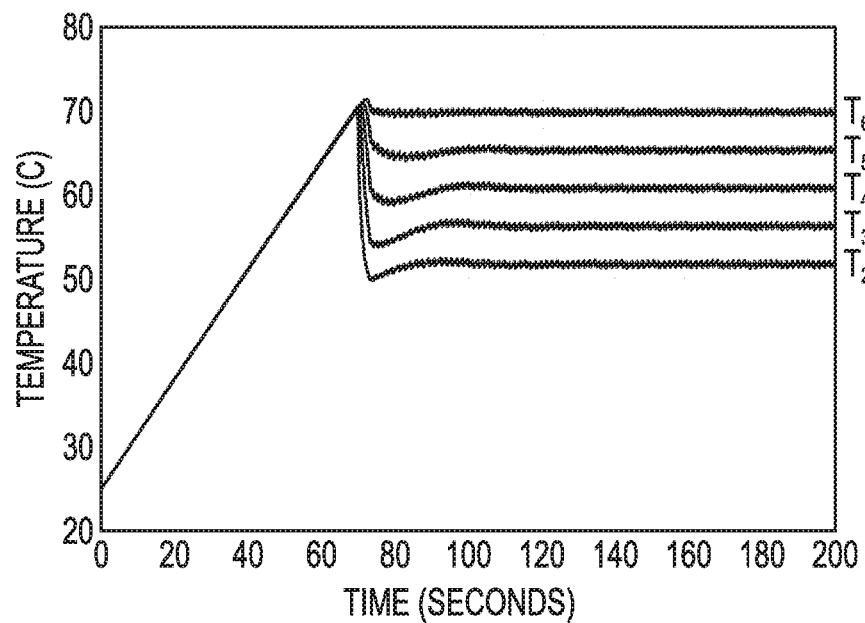
FIG. 37 is a graphical representation of the temperature of fluid in the fluid heating system at particular locations over time, according to one or more embodiments.

Another example relating to the impact of the solar loss factor is shown in FIG. 37. The solar loss factor may be impacted by many items including imperfections in the mirror relating to curvature and surface reflectivity as well as by the absorptivity of the elongated flow element. As shown, the solar loss factor has been increased from 0.5 to 0.75 with the other parameters remaining the same as those shown in FIG. 37. A comparison of FIG. 31 to FIG. 37 demonstrates that while the quasi-steady temperatures are nearly the same, the duration of the transient heating process may be shortened with higher loss factors.

Given the discussion of pathogen inactivation and the discussion of the performance calculations of the solar collector, a further analysis can show results of pathogen inactivation as water flows through the system. For example, *Escherichia Coli* O3:H6 may be considered. D (i.e., the decimal reduction time) has been recorded as 401 seconds at temperatures of 55 degrees C. with a z value of 5.6 degrees C. For these values, and with Equations 2 and 5, k can be found to be $$k = 8.66 \times 10^{-14} \cdot e^{0.411T} (1/\text{seconds}) \qquad \text{Eq. 17}$$

with temperature expressed in degrees C. Calculations carried out with the values listed in FIG. 33 may result in a quasi-steady temperature variation which begins to occur after approximately 100 seconds of heating. A conservative approach may be taken to limit the risk of active pathogens by applying Equation 6 to the water in the elongated flow element without giving credit to any heating prior to entry into the elongated flow element or after it leaves the elongated flow element. That is, any pathogen inactivation between $T_6$ and $T_{out}$ may be ignored.

Figure 38:
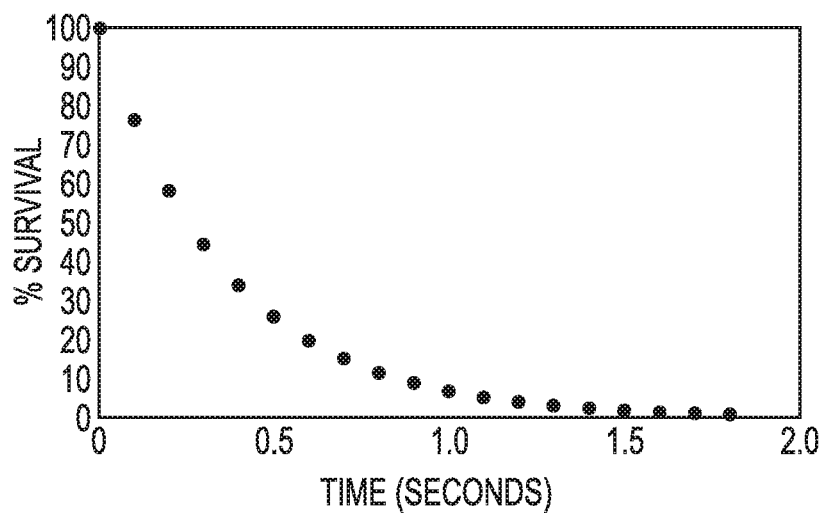
FIG. 38 is a graphical representation of pathogen survival rates over time as they pass through the fluid heating system.

The result of the calculations are shown in FIG. 38. As shown, pathogen inactivation is displayed as a percentage of initial pathogens. The time is displayed as a normalized quantity (normalized by the period of the quasi-steady oscillations). That is, time 0 is when the system gets to a steady-state operation. (recall that before that time, the temperature of the entire elongated flow element reaches the valve operation temperature so harsher conditions for the pathogen exist during that period). To be clear about what is seen in FIG. 38 as a control volume of water enters the elongated flow element and flows across the elongated flow element at the temperatures shown in FIG. 31, the inactivation of *E. Coli* occurs over a two second period.

The calculations which were completed to create the results of FIG. 38 may be replicated with other pathogens as well where inactivation kinetic terms are known. Moreover, the methodology described here may be used to calculate results for a wide range of parameter setting.

It is to be appreciated that while the above model has been shown with respect to a parabolic solar collector other sources of heat may be provided. That is, for example, where the elongated flow element is exposed to an open flame similar calculations may be performed to establish pathogen inactivation based on a the amount of heat being supplied and its effect on the temperatures in the elongated flow element.

EXAMPLES

In one or more embodiments, a fluid heating system may include a solar collection system configured for focusing sunlight on a focal axis, an elongated flow element arranged and configured for transporting fluid along the solar collection system at the focal axis, and a flow-control assembly comprising thermostatic valves configured to control the flow of the fluid in the elongated flow element such that pathogens present in the fluid are substantially inactivated before the fluid exits the fluid heating system. The system may also include a preheat heat exchanger configured to utilize fluid exiting the fluid heating system to heat fluid entering the fluid heating system. The preheat heat exchanger may include a first tortuous pathway and a second tortuous pathway, the first and second tortuous pathways being in substantial alignment with one another such that heat may be exchanged between the pathways. The system may also include a water collecting reservoir configured to collect water to be pasteurized. The solar collection system may include a reflective element including a solar film laminated to a flexible substrate. The solar collection system may also include a frame defining a parabolic shape and the reflective element may be held in shape by the frame.

In one or more embodiments, the system may include a housing arranged about a non-exposed side of the elongated flow element. The housing may include an insulating material. In one or more embodiments, the hood may be configured to resist convective flow of air by the elongated flow element. The system may also include a return line, the return line being positioned in the housing. The return line may be insulated from the elongated flow element. The elongated flow element may be secured to the control valve assembly at a first end and to the preheat heat exchanger at a second end and the elongated flow element may be secured at each end with an expansion joint.

The system may also include a treated fluid collection tank. The system may also include a tracking system configured for directing the solar collection system at the sun. In one or more embodiments, the collection tank may include a fluid level sensor in communication with the tracking system and the tracking system may be configured to direct the solar collection system away from the sun when the fluid level sensor indicates that the treated fluid collection tank is full.

The tracking system may include a dual axis tracking system configured for directing the solar collection system at the sun. The dual axis tracking system may be configured to pivot the solar collection system about two axes. The system may also include a support structure including an upright support member, an arm portion extending laterally from the upright support member, and a spine portion offset from the arm portion and extending substantially parallel to the arm portion. The arm portion may be pivotable about a seasonal axis extending perpendicular to the upright support member and perpendicular to the arm portion. The spine portion may be pivotable about a day axis extending longitudinally along the spine portion. The system may also include two actuation assemblies for pivoting the solar collection system about the seasonal and day axes.

In one or more embodiments, a method of operating a fluid heating system wherein the fluid heating system comprises a parabolic solar collector and a support structure may be provided. The method may include arranging the fluid heating system along a North/South axis on the surface of the earth and directing the parabolic solar collector at a sun. Directing the parabolic solar collector may include activating a control module comprising a GPS communication device, wherein the control module receives GPS data from satellites including coordinate data defining the location of the fluid heating system on the surface of a planet, date data, and time data and automatically directs the solar collector at a sun. Automatically directing the solar collector at the sun may include pivoting the solar collector about a day axis and a seasonal axis. The seasonal axis may be a substantially horizontal axis relative to the surface of the planet. The day axis may be an axis arranged substantially parallel to a longitudinal length of the solar collector.

In one or more embodiments, a control valve assembly for passively controlling flow of fluid may include a housing, an inlet, an outlet, and a plurality of thermostatic control valves biased toward a closed position and arranged within the housing between the inlet and the outlet. The thermostatic control valves may each be associated with separate respective flow paths between the inlet and the outlet and have different operating temperatures. The valves may be configured to open at their respective operating temperatures and remain open unless the fluid falls below their respective operating temperature such that when multiple thermostatic control valves are open the amount of fluid flowing through the control valve is equal to the addition of the amount of fluid flowing through each valve. The plurality of thermostatic control valves may include three valves. The operating temperatures of the thermostatic control valves may be selected to limit the passage of pathogens through the control valve assembly. The flow rates of the thermostatic control valves may be selected to limit passage of pathogens through the control valve assembly. The operating temperatures and the flow rates of the thermostatic control valves may be selected to limit the passage of pathogens through the control valve assembly.

In one or more embodiments, a first valve of the plurality of thermostatic control valves may have a range of flow rates and a valve closing time associated with the amount of time it takes the valve to close and a portion of a first flow path associated with the first valve extends from the chamber to the first valve and has a length selected such that fluid flowing from the chamber through the portion of the first flow path to the valve at the range of flow rates will not reach the valve in a time less than the closing time.

In one or more embodiments, a method of determining pathogen inactivation may include performing an energy balance on a fluid heating system. Performing an energy balance may include calculating temperatures of a fluid at a plurality of locations as the fluid flows through the fluid heating system. The method of determining pathogen inactivation may also include receiving inactivation kinetic data regarding a pathogen present in the fluid and determining pathogen inactivation amounts based on exposure to the temperatures. Performing an energy balance may include receiving a plurality of input parameters relating to the fluid heating system. The plurality of input parameters may relate to a solar collection system and an associated fluid control system. The solar collection system may include a parabolic mirror and the fluid control system includes an elongated flow element arranged along a focal axis of the parabolic mirror. The plurality of locations may include locations along the length of the elongated flow element. In one or more embodiments, the method may include adjusting the input parameters and calculating revised temperatures at the plurality of locations. The method may also include determining revised pathogen inactivation amounts based on exposure to the revised temperatures. The method may also include receiving inactivation kinetic data regarding another pathogen present in the fluid. The method may also include determining pathogen inactivation amounts of the another pathogen based on exposure to the temperatures.

In one or more embodiments, a degassing valve may include a cap secured to a housing over a chamber. The cap may include a gas relief orifice. The valve may also include a float arranged in the chamber and configured to articulate between an open position and a closed position within the chamber. The float may provide a closing force based on its buoyancy when arranged in the closed position. A linkage may be operably connected to the cap and the float. The linkage may have a sealing stopper configured to seal the gas relief orifice when the float is in a closed position. The linkage may further be configured to magnify the closing force of the float such that a sealing force provided on the sealing stopper by the linkage is a multiple of the float force. The multiple of the float force may range from approximately 10 to approximately 30 or from approximately 15 to approximately 25, or from approximately 16 to approximately 20. The linkage may include a bottom linkage bar, a strut, and a top linkage bar. The float may engage the bottom linkage bar at a first end and the bottom linkage bar may be pivotable at a second end about a pivot point having a fixed position relative to the cap and the strut may engage the bottom linkage between the first end and the second end. The strut may engage the bottom linkage bar at a midpoint closer to the second end than the first end. The strut may engage the top linkage bar at a first end and the top linkage bar may be pivotable at a second end about a pivot point having a fixed position relative to the cap and the sealing stopper may be positioned on the top linkage bar between the first end and the second end. The sealing stopper may be arranged on the top linkage bar at a midpoint closer to the second end than the first end.

In one or more embodiments, a tracking device for tracking the location of a moving object may include a spine portion for carrying a payload, a first linear actuation assembly for causing the payload to rotate about a first axis of rotation, a second linear actuation assembly for causing the payload to rotate about a second axis of rotation, and a control module configured to determine a position of a moving object in the sky. The control module may be further configured to operate the first and second linear actuation assemblies to direct the payload relative to the moving object. In one or more embodiments, the first linear actuation assembly and second linear actuation assembly may each include a linear actuator and a motor. In one or more embodiments, the first linear actuation assembly and second linear actuation assembly may include a linear absolute encoder. In one embodiment, the second axis of rotation may align with a longitudinal axis of the spine portion and the first axis of rotation may be orthogonal to the second axis of rotation. In one or more embodiments, the tracking device may also include an upright portion supporting the spine portion, an arm portion between the spine portion and the upright portion, and a single axis support coupling the arm portion to the upright portion. The first actuation assembly may be coupled to the upright portion and pivotably coupled to the arm portion. The second actuation assembly may be coupled to the arm portion and pivotably coupled to the spine portion with a torque arm. The spine portion may remain static with respect to a third axis of rotation defined as a vertical axis aligned with the upright portion. The device may also be configured for wireless communication.

In one or more other embodiments, a solar tracking device for tracking the location of the sun over a period of time may include a spine portion carrying at least one of a solar panel, solar concentrator, and heliostat, a first linear actuation assembly for causing the one or more solar panels to rotate about a first axis of rotation, a second linear actuation assembly for causing the one or more solar panels to rotate about a second axis of rotation, and a control module configured to receive Global Positioning System data comprising the tracking device's location, the time, and the date, determine the location of the sun based on the Global Positioning System data, direct the first and second actuation assemblies to position the one or more solar panels such that the one or more solar panels are directed relative to the sun. The first linear actuation assembly and second linear actuation assembly may include a linear actuator and a motor. The first linear actuation assembly and second linear actuation assembly may each further include a linear absolute encoder. The second axis of rotation may align with a longitudinal axis of the spine portion the first axis of rotation may be orthogonal to the second axis of rotation. The tracking device may also include an upright portion supporting the spine portion, an arm portion between the spine portion and the upright portion, and a single axis support coupling the arm portion to the upright portion. The first actuation assembly may be coupled to the upright portion and pivotably coupled to the arm portion. The second actuation assembly may be coupled to the arm portion and pivotably coupled to the spine portion with a torque arm. The spine portion may include a first end and a second end and the first end may be directed North and the second end may be directed South. The device may be configured for wireless communication. The first and second actuation assemblies may include referencing an error correction lookup table.

In one or more embodiments, a method for directing a payload relative to a moving object may include receiving Global Positioning System data related to the time, date, and location of a tracking device, determining an azimuth and altitude of the moving object with respect to the tracking device, calculating a first angular motion path corresponding to a first axis of rotation of the payload and a second angular motion path corresponding to a second axis of rotation of the payload, calculating a first linear motion path and a second linear motion path from the first and second angular motion paths, and directing the device to rotate the payload in accordance with the first and second linear motion paths. The method may also include repeating the method at timed intervals over the course of a day. The method may also include calculating an error correction for the first linear motion path and second linear motion path. The error correction may be determined by referencing an error correction lookup table and using bicubic interpolation to interpolate an error correction.

In one or more embodiments, a tower structure may include a tracking device for tracking the location of a moving object. The tracking device may include a spine portion for carrying a payload, a first linear actuation assembly causing the payload to rotate about a first axis of rotation, a second linear actuation assembly causing the payload to rotate about a second axis of rotation, and a control module configured to determine a position of a moving object in the sky, the control module further configured to operate the first and second linear actuation assemblies to direct the payload relative to the moving object. The tower structure may include a communication tower. The tower structure may include a solar power tower. The payload may include a heliostat.

For purposes of this disclosure, any system described herein may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, a system or any portion thereof may be a personal computer (e.g., desktop or laptop), tablet computer, mobile device (e.g., personal digital assistant (PDA) or smart phone), server (e.g., blade server or rack server), a network storage device, or any other suitable device or combination of devices and may vary in size, shape, performance, functionality, and price. A system may include random access memory (RAM), one or more processing resources such as a central processing unit (CPU) or hardware or software control logic, ROM, and/or other types of nonvolatile memory. Additional components of a system may include one or more disk drives or one or more mass storage devices, one or more network ports for communicating with external devices as well as various input and output (I/O) devices, such as a keyboard, a mouse, touchscreen and/or a video display. Mass storage devices may include, but are not limited to, a hard disk drive, floppy disk drive, CD-ROM drive, smart drive, flash drive, or other types of non-volatile data storage, a plurality of storage devices, or any combination of storage devices. A system may include what is referred to as a user interface, which may generally include a display, mouse or other cursor control device, keyboard, button, touchpad, touch screen, microphone, camera, video recorder, speaker, LED, light, joystick, switch, buzzer, bell, and/or other user input/output device for communicating with one or more users or for entering information into the system. Output devices may include any type of device for presenting information to a user, including but not limited to, a computer monitor, flat-screen display, or other visual display, a printer, and/or speakers or any other device for providing information in audio form, such as a telephone, a plurality of output devices, or any combination of output devices. A system may also include one or more buses operable to transmit communications between the various hardware components.

One or more programs or applications, such as a web browser, and/or other applications may be stored in one or more of the system data storage devices. Programs or applications may be loaded in part or in whole into a main memory or processor during execution by the processor. One or more processors may execute applications or programs to run systems or methods of the present disclosure, or portions thereof, stored as executable programs or program code in the memory, or received from the Internet or other network. Any commercial or freeware web browser or other application capable of retrieving content from a network and displaying pages or screens may be used. In some embodiments, a customized application may be used to access, display, and update information.

Hardware and software components of the present disclosure, as discussed herein, may be integral portions of a single computer or server or may be connected parts of a computer network. The hardware and software components may be located within a single location or, in other embodiments, portions of the hardware and software components may be divided among a plurality of locations and connected directly or through a global computer information network, such as the Internet.

As will be appreciated by one of skill in the art, the various embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present disclosure may take the form of an entirely hardware embodiment, an entirely software embodiment (including firmware, middleware, microcode, hardware description languages, etc.), or an embodiment combining software and hardware aspects. Furthermore, embodiments of the present disclosure may take the form of a computer program product on a computer-readable medium or computer-readable storage medium, having computer-executable program code embodied in the medium, that define processes or methods described herein. A processor or processors may perform the necessary tasks defined by the computer-executable program code. Computer-executable program code for carrying out operations of embodiments of the present disclosure may be written in an object oriented, scripted or unscripted programming language such as Java, Perl, PHP, Visual Basic, Smalltalk, C++, or the like. However, the computer program code for carrying out operations of embodiments of the present disclosure may also be written in conventional procedural programming languages, such as the C programming language or similar programming languages. A code segment may represent a procedure, a function, a subprogram, a program, a routine, a subroutine, a module, an object, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In the context of this document, a computer readable medium may be any medium that can contain, store, communicate, or transport the program for use by or in connection with the systems disclosed herein. The computer-executable program code may be transmitted using any appropriate medium, including but not limited to the Internet, optical fiber cable, radio frequency (RF) signals or other wireless signals, or other mediums. The computer readable medium may be, for example but is not limited to, an electronic, magnetic, optical, electromagnetic, infrared, or semiconductor system, apparatus, or device. More specific examples of suitable computer readable medium include, but are not limited to, an electrical connection having one or more wires or a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device. Computer-readable media includes, but is not to be confused with, computer-readable storage medium, which is intended to cover all physical, non-transitory, or similar embodiments of computer-readable media.

Various embodiments of the present disclosure may be described herein with reference to flowchart illustrations and/or block diagrams of methods, apparatus (systems), and computer program products. It is understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks. Alternatively, computer program implemented steps or acts may be combined with operator or human implemented steps or acts in order to carry out an embodiment of the invention.

Additionally, although a flowchart may illustrate a method as a sequential process, many of the operations in the flowcharts illustrated herein can be performed in parallel or concurrently. In addition, the order of the method steps illustrated in a flowchart may be rearranged for some embodiments. Similarly, a method illustrated in a flow chart could have additional steps not included therein or fewer steps than those shown. A method step may correspond to a method, a function, a procedure, a subroutine, a subprogram, etc.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A method of setting a fluid heating system, the fluid heating system having a solar collector configured for focusing sunlight on a focal axis, an elongated flow element arranged and configured for heating and transporting liquid water along the solar collection system at the focal axis in a fixed configuration with the solar collector, and a flow-control assembly configured to control the flow of liquid water in the elongated flow element to control heating of the liquid water below a boiling temperature and to establish a mass flow rate of the liquid water, the method comprising:

receiving a desired pathogen reduction in the liquid water in the fluid heating system at the flow-control assembly;

receiving a series of time-varying temperatures of the liquid water as it flows through the elongated flow element, the series of time-varying temperatures defining a quasi-steady state of temperatures at different points along the elongated flow element and that oscillate due to pulsed flow that occurs as the flow-control assembly opens and closes;

calculating a calculated pathogen reduction at the flow-control assembly using a decimal reduction model that accounts for the dynamically changing water temperatures as the liquid water flows along the elongated flow element by accumulating pathogen reductions due to each of the temperatures of the flowing water at the different points and the amount of time the liquid water is at each temperature based on the mass flow rate and the pulsed flow;

comparing the calculated pathogen reduction to the desired pathogen reduction;

setting a temperature to control the flow-control assembly based on the comparing of the calculated pathogen reduction to the desired pathogen reduction; and controlling the mass flow rate of the liquid water using the flow-control assembly based on the set temperature to provide the desired pathogen reduction.

2. The method of claim 1, wherein the decimal reduction model for pathogen inactivation is a first-order rate model.

3. The method of claim 1, wherein the decimal reduction model for pathogen inactivation is solved using a forward-stepping integration scheme.

4. The method of claim 1, wherein the series of time-varying temperatures comprises discrete and increasing temperatures of the liquid water as the liquid water flows through the elongated flow element.

5. The method of claim 4, wherein the discrete and increasing temperatures are based on an operating temperature of the flow-control assembly.

6. The method of claim 5, wherein receiving a series of time-varying temperatures of the liquid water comprises calculating the series of time-varying temperatures using an energy balance of the fluid heating system at the operating temperature.

7. The method of claim 1, wherein the flow-control assembly comprises a single control valve to control the flow of liquid water in the elongated flow element and the return line and to establish the mass flow rate of the liquid water.

8. The method of claim 1, comprising:

receiving the desired pathogen reduction from a user.

9. The method of claim 1, wherein the temperature to control the flow-control assembly is lower than a corresponding temperature required to achieve the desired pathogen reduction without accounting for the accumulated pathogen reductions from the series of time-varying temperatures of the liquid water in the elongated flow element calculated using the decimal reduction model.

10. A method of controlling a fluid heating system, the fluid heating system having a solar collector configured for focusing sunlight on a focal axis, an elongated flow element arranged and configured for heating and transporting liquid water along the solar collection system at the focal axis in a fixed configuration with the solar collector, and a flow-control assembly configured to control the flow of liquid water in the elongated flow element to control heating of the liquid water below a boiling temperature and to establish a mass flow rate of the liquid water, the method comprising:

receiving a desired pathogen reduction in the liquid water in the fluid heating system flow-control assembly;

receiving a series of time-varying temperatures of the liquid water as it flows through the elongated flow element, the series of time-varying temperatures defining a quasi-steady state of temperatures at different points along the elongated flow element and that oscillate due to pulsed flow that occurs as the flow-control assembly opens and closes;

calculating a calculated pathogen reduction at the flow-control assembly using a decimal reduction model that accounts for the dynamically changing water temperatures as the liquid water flows along the elongated flow element by accumulating pathogen reductions due to each of the temperatures of the flowing water at different points and the amount of time the liquid water is at each temperature based on the mass flow rate and the pulsed flow; and controlling the mass flow rate of the liquid water through the flow-control assembly using the calculated pathogen reduction to provide the desired pathogen reduction.

11. The method of claim 10, wherein the flow-control assembly comprises a single control valve to control the flow of liquid water in the elongated flow element and the return line and to establish the mass flow rate of the liquid water.

12. The method of claim 10, comprising:
receiving the desired pathogen reduction from a user.

13. The method of claim 10, wherein the temperature to control the flow-control assembly is lower than a corresponding temperature required to achieve the desired pathogen reduction without accounting for the accumulated pathogen reductions from the series of time-varying temperatures of the liquid water in the elongated flow element calculated using the decimal reduction model.

* * * * *

UNITED STATES PATENT AND TRADEMARK OFFICE
CERTIFICATE OF CORRECTION

| | | |
|---|---|---|
| PATENT NO. | : 11,946,886 B2 | Page 1 of 1 |
| APPLICATION NO. | : 14/954292 | |
| DATED | : April 2, 2024 | |
| INVENTOR(S) | : Plourde et al. | |

It is certified that error appears in the above-identified patent and that said Letters Patent is hereby corrected as shown below:

In the Claims

In Column 49, Line 2, in Claim 10, after "system", insert --at the--

Signed and Sealed this
Third Day of June, 2025

Coke Morgan Stewart
*Acting Director of the United States Patent and Trademark Office*